United States Patent
Nishio et al.

(10) Patent No.: US 10,802,399 B2
(45) Date of Patent: Oct. 13, 2020

(54) ACTINIC RAY-SENSITIVE OR RADIATION-SENSITIVE RESIN COMPOSITION, RESIST FILM, PATTERN FORMING METHOD, AND METHOD FOR MANUFACTURING ELECTRONIC DEVICE

(71) Applicant: FUJIFILM Corporation, Tokyo (JP)

(72) Inventors: Ryo Nishio, Shizuoka (JP); Masafumi Kojima, Shizuoka (JP); Akiyoshi Goto, Shizuoka (JP); Tomotaka Tsuchimura, Shizuoka (JP); Michihiro Shirakawa, Shizuoka (JP); Keita Kato, Shizuoka (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 16/110,394

(22) Filed: Aug. 23, 2018

(65) Prior Publication Data

US 2018/0364571 A1     Dec. 20, 2018

Related U.S. Application Data

(63) Continuation of application No. PCT/JP2017/000986, filed on Jan. 13, 2017.

(30) Foreign Application Priority Data

Mar. 7, 2016  (JP) .................................. 2016-043586

(51) Int. Cl.

| | |
|---|---|
| G03F 7/004 | (2006.01) |
| G03F 7/039 | (2006.01) |
| G03F 7/038 | (2006.01) |
| G03F 7/16 | (2006.01) |
| G03F 7/20 | (2006.01) |
| G03F 7/32 | (2006.01) |
| G03F 7/38 | (2006.01) |

(Continued)

(52) U.S. Cl.
CPC .......... *G03F 7/0045* (2013.01); *C07C 309/12* (2013.01); *C07C 309/15* (2013.01); *C07C 309/17* (2013.01); *C07C 321/28* (2013.01); *C07C 381/12* (2013.01); *C07D 213/70* (2013.01); *C07D 217/08* (2013.01); *C07D 327/08* (2013.01); *C07D 333/46* (2013.01); *C07D 335/16* (2013.01); *G03F 7/038* (2013.01); *G03F 7/039* (2013.01); *G03F 7/0392* (2013.01); *G03F 7/16* (2013.01); *G03F 7/168* (2013.01); *G03F 7/2006* (2013.01); *G03F 7/2041* (2013.01); *G03F 7/32* (2013.01); *G03F 7/38* (2013.01); *C07C 2603/74* (2017.05); *C07J 9/005* (2013.01); *C07J 31/006* (2013.01); *C07J 43/003* (2013.01)

(58) Field of Classification Search
CPC ... C07C 309/15; C07C 321/28; C07C 309/17; C07C 309/12; C07C 381/12; C07C 2603/74; C07D 213/70; C07D 217/08; C07D 327/08; C07D 333/46; C07D 335/16; C07J 9/005; C07J 31/006; C07J 43/003; G03F 7/0045; G03F 7/0392; G03F 7/168; G03F 7/16; G03F 7/2006; G03F 7/2041; G03F 7/32; G03F 7/38; G03F 7/039; G03F 7/038
See application file for complete search history.

(56) References Cited

U.S. PATENT DOCUMENTS 6,479,211 B1 * 11/2002 Sato ...................... G03F 7/0048
                                                            430/270.1
6,723,483 B1 *  4/2004 Oono .................... C07C 381/12
                                                            430/170

(Continued)

FOREIGN PATENT DOCUMENTS

| JP | 05255240 A | * 10/1993 |
|---|---|---|
| JP | 2008120700 A | 5/2008 |

(Continued)

OTHER PUBLICATIONS

English Translation of JP 2014-066925 A from J-PlatPat[JPP] Publication of JP doc generated Jul. 2019, publication on Apr. 17, 2014, copyright JPO and INPIT, 75 pages. (Year: 2014).*

(Continued)

*Primary Examiner* — Cynthia Hamilton
(74) *Attorney, Agent, or Firm* — Sughrue Mion, PLLC

(57) ABSTRACT

The present invention provides an actinic ray-sensitive or radiation-sensitive resin composition which is capable of forming a pattern having a low LWR and is further suppressed in the collapse of the formed pattern, a resist film, a pattern forming method, and a method for manufacturing an electronic device. The actinic ray-sensitive or radiation-sensitive resin composition of the present invention contains a photoacid generator represented by General Formula (1) or a resin having a residue obtained by removing one hydrogen atom from the photoacid generator represented by General Formula (1).

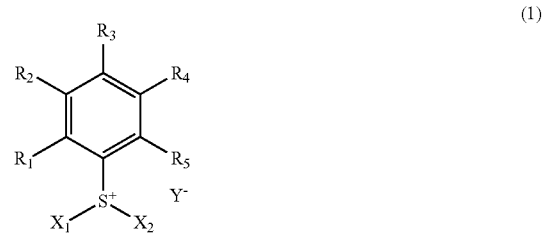

(1)

20 Claims, No Drawings

(51) Int. Cl.
  *C07C 309/12* (2006.01)
  *C07C 309/17* (2006.01)
  *C07C 381/12* (2006.01)
  *C07C 309/15* (2006.01)
  *C07C 321/28* (2006.01)
  *C07D 213/70* (2006.01)
  *C07D 217/08* (2006.01)
  *C07D 327/08* (2006.01)
  *C07D 333/46* (2006.01)
  *C07D 335/16* (2006.01)
  *C07J 31/00* (2006.01)
  *C07J 9/00* (2006.01)
  *C07J 43/00* (2006.01)

(56) References Cited

U.S. PATENT DOCUMENTS

| | | | | |
|---|---|---|---|---|
| 2002/0090569 | A1* | 7/2002 | Suzuki | G03F 7/0045 430/270.1 |
| 2011/0189609 | A1* | 8/2011 | Kawabata | C07D 327/08 430/270.1 |
| 2011/0293900 | A1 | 12/2011 | Tomeba et al. | |
| 2012/0273924 | A1 | 11/2012 | Matsuda et al. | |
| 2014/0080059 | A1 | 3/2014 | LaBeaume et al. | |
| 2015/0086911 | A1 | 3/2015 | Tsuruta et al. | |
| 2015/0086912 | A1* | 3/2015 | Kawabata | C08F 12/20 430/18 |
| 2015/0118628 | A1 | 4/2015 | Kawabata et al. | |

FOREIGN PATENT DOCUMENTS

| | | |
|---|---|---|
| JP | 2010-134279 A | 6/2010 |
| JP | 2011253017 A | 12/2011 |
| JP | 2012-133053 A | 7/2012 |
| JP | 2013064970 A | 4/2013 |
| JP | 2013-156416 A | 8/2013 |
| JP | 2013234320 A | 11/2013 |
| JP | 2014006503 A | 1/2014 |
| JP | 2014016478 A | 1/2014 |
| JP | 2014029481 A | 2/2014 |
| JP | 2014-63160 A | 4/2014 |
| JP | 2014-66925 A | 4/2014 |
| WO | 2014033967 A1 | 3/2014 |

OTHER PUBLICATIONS

English Translation of JP 2012-133053 A from J-PlatPat[JPP] generated Jul. 2019, publication of JP doc on Jul. 12, 2012, copyright JPO and INPIT, 169 pages. (Year: 2012).*
English Translation of JP 2013-156416 A from J-PlatPat[JPP] generated Jul. 2019, publication of JP doc on Aug. 15, 2013, copyright JPO and INPIT, 132 pages. (Year: 2013).*
English Translation of JP 05-255240 A from J-PlatPat[JPP] generated Jul. 2019, publication of JP doc on Oct. 5, 1993, copyright JPO and INPIT, 11 pages. (Year: 1993).*
"Organic compound" from Britanica Online Encclopedia, date published Mar. 7, 2019 accessed Jul. 18, 2019, one page dated Oct. 30, 2017. (Year: 2019).*
ACSH Explains: What does "Organic" Really Mean?/ american Council Science and Health, 2 pages, (Year: 2017).*
Communication dated Jan. 8, 2019 from the Japanese Patent Office in application No. 2018-504025.
Written Opinion, dated Apr. 18, 2017 from the International Bureau in counterpart International application No. PCT/JP2017/000986.
International Preliminary Report on Patentability and Translation of Written Opinion, dated Sep. 11, 2018 from the International Bureau in counterpart International application No. PCT/JP2017/000986.
International Search Report for PCT/JP2017/000986 dated Apr. 18, 2017.
Notice of Reasons for Refusal dated Jul. 9, 2019 from the Japanese Patent Office in application No. 2018-504025.
Notification of Reason for Refusal dated Dec. 18, 2019 from the Korean Intellectual Property Office in Korean application No. 10-2018-7022319.
Office Action dated Jun. 24, 2020 by the Korean Patent Office in Korean application No. 10-2018-7022319.
Office Action dated Aug. 24, 2020 by the Korean Patent Office in corresponding Korean application No. 10-2018-7022319.

* cited by examiner

ACTINIC RAY-SENSITIVE OR RADIATION-SENSITIVE RESIN COMPOSITION, RESIST FILM, PATTERN FORMING METHOD, AND METHOD FOR MANUFACTURING ELECTRONIC DEVICE

CROSS-REFERENCE TO RELATED APPLICATIONS

This application is a Continuation of PCT International Application No. PCT/JP2017/000986 filed on Jan. 13, 2017, which claims priority under 35 U.S.C. § 119(a) to Japanese Patent Application No. 2016-043586 filed on Mar. 7, 2016. The above application is hereby expressly incorporated by reference, in its entirety, into the present application.

BACKGROUND OF THE INVENTION

1. Field of the Invention

The present invention relates to an actinic ray-sensitive or radiation-sensitive resin composition, a resist film, a pattern forming method, and a method for manufacturing an electronic device.

More specifically, the present invention relates to an actinic ray-sensitive or radiation-sensitive resin composition which is suitable for a process for manufacturing a semiconductor such as an integrated circuit (IC), a process for manufacturing a circuit board for a liquid crystal, a thermal head, or the like, and other lithographic processes of photofabrication, a resist film, a pattern forming method, and a method for manufacturing an electronic device.

2. Description of the Related Art

In the related art, in processes for manufacturing a semiconductor device such as an IC, fine processing by lithography using an actinic ray-sensitive or radiation-sensitive resin composition which is a photoresist composition has been carried out.

The actinic ray-sensitive or radiation-sensitive resin composition is a pattern forming material that generates an acid in an exposed area upon irradiation with actinic radiation or electron beams, and changes a solubility in a developer between an area irradiated or not irradiated with actinic radiation or electron beams by the reaction using the acid as a catalyst, thereby forming a pattern on a substrate.

For a photoacid generator which is a main constituent of the actinic ray-sensitive or radiation-sensitive resin composition, various compounds are developed. For example, in JP2010-134279A, a triphenylsulfonium-type photoacid generator is used.

SUMMARY OF THE INVENTION

On the other hand, in recent years, characteristics required for a pattern formed by the actinic ray-sensitive or radiation-sensitive resin composition have been increasingly enhanced, and in particular, further reduction in line width roughness (LWR) and more difficulty in occurrence of pattern collapse even with a finer pattern (suppression of pattern collapse) have been required.

The present inventors have formed a pattern using an actinic ray-sensitive or radiation-sensitive resin composition including the triphenylsulfonium-type photoacid generator described in JP2010-134279A, and as a result, it was not necessarily sufficient in satisfying both of reduction in LWR and suppression of pattern collapse, and thus, it was necessary to satisfy them at a higher level.

Taking such circumstances into consideration, an object of the present invention is to provide an actinic ray-sensitive or radiation-sensitive resin composition which is capable of forming a pattern having a low LWR and is further suppressed in the collapse of the formed pattern.

Furthermore, another object of the present invention is to provide a resist film formed using the actinic ray-sensitive or radiation-sensitive resin composition, a pattern forming method, and a method for manufacturing an electronic device.

The present inventors have conducted extensive studies on the problem, and as a result, they have found that the objects can be accomplished by using a photoacid generator having a predetermined structure, thereby leading to the present invention.

That is, the present inventors have found that the objects can be accomplished by the following configuration.

(1) An actinic ray-sensitive or radiation-sensitive resin composition comprising a photoacid generator represented by General Formula (1) which will be described later, or a resin having a residue obtained by removing one hydrogen atom from the photoacid generator represented by General Formula (1) which will be described later.

(2) The actinic ray-sensitive or radiation-sensitive resin composition as described in (1),
in which the photoacid generator represented by General Formula (1) is a photoacid generator represented by General Formula (1-A) which will be described later.

(3) The actinic ray-sensitive or radiation-sensitive resin composition as described in (1) or (2),
in which the photoacid generator represented by General Formula (1) is a photoacid generator represented by General Formula (1-B) which will be described later.

(4) The actinic ray-sensitive or radiation-sensitive resin composition as described in any one of (1) to (3),
in which $R_1$ represents an alkoxy group, an alkylthio group, a halogen atom, or a cyano group.

(5) The actinic ray-sensitive or radiation-sensitive resin composition as described in any one of (1) to (4),
in which $Y^-$ is an anion represented by General Formula (2) which will be described later.

(6) The actinic ray-sensitive or radiation-sensitive resin composition as described in any one of (1) to (5), further comprising a resin including a repeating unit having a group that decomposes by the action of an acid to generate an alkali-soluble group.

(7) The actinic ray-sensitive or radiation-sensitive resin composition as described in any one of (1) to (6), further comprising an acid diffusion control agent.

(8) A resist film formed using the actinic ray-sensitive or radiation-sensitive resin composition as described in any one of (1) to (7).

(9) A pattern forming method comprising:
a step of exposing the resist film as described in (8); and
a step of developing the exposed resist film.

(10) The pattern forming method as described in (9),
in which the exposure is liquid immersion exposure.

(11) A method for manufacturing an electronic device, comprising the pattern forming method as described in (9) or (10).

According to the present invention, it is possible to provide an actinic ray-sensitive or radiation-sensitive resin composition which is capable of forming a pattern having a low LWR and is further suppressed in the collapse of the formed pattern.

Furthermore, according to the present invention, it is also possible to provide a resist film formed using the actinic ray-sensitive or radiation-sensitive resin composition, a pattern forming method, and a method for manufacturing an electronic device.

DESCRIPTION OF THE PREFERRED EMBODIMENTS

Hereinafter, suitable aspects of the present invention will be described in detail.

In citations for a group and an atomic group in the present specification, in a case where the group or the atomic group is denoted without specifying whether it is substituted or unsubstituted, the group or the atomic group includes both a group and an atomic group not having a substituent, and a group and an atomic group having a substituent. For example, an "alkyl group" which is not denoted about whether it is substituted or unsubstituted encompasses not only an alkyl group not having a substituent (unsubstituted alkyl group), but also an alkyl group having a substituent (substituted alkyl group).

Furthermore, in the present invention, "actinic rays" or "radiation" means, for example, a bright line spectrum of a mercury lamp, far ultraviolet rays typified by an excimer laser, extreme ultraviolet rays (EUV light), X-rays, particle rays such as electron beams and ion beams, or the like. In addition, in the present invention, "light" means actinic rays or radiation.

Furthermore, "exposure" in the present specification encompasses, unless otherwise specified, not only exposure by a mercury lamp, far ultraviolet rays typified by an excimer laser, X-rays, extreme ultraviolet rays (EUV light), or the like, but also lithography by particle rays such as electron beams and ion beams.

In the present specification, "(meth)acrylate" means "at least one of acrylate or methacrylate". Further, "(meth)acrylic acid" means "at least one of acrylic acid or methacrylic acid".

In the present specification, a numerical range expressed using "to" means a range that includes the preceding and succeeding numerical values of "to" as the lower limit value and the upper limit value, respectively.

<Actinic Ray-Sensitive or Radiation-Sensitive Resin Composition>

First, the actinic ray-sensitive or radiation-sensitive resin composition (hereinafter also referred to as "the composition") according to the present invention will be described. This composition may be used for negative tone development, or may also be used for positive tone development. That is, this composition may be used for development using a developer including an organic solvent, or may also be used for development using an alkali developer.

The composition contains a photoacid generator represented by General Formula (1) or a resin having a residue obtained by removing one hydrogen atom from the photoacid generator represented by General Formula (1).

Hereinafter, a mechanism for obtaining a desired effect using the composition of the present invention will be described.

First, examples of a method for improving the LWR of the pattern include a method for increasing the amount of a photoacid generator to be used. However, a triphenylsulfonium-type photoacid generator in the related art has a high absorbance (in other words, a low transmittance) at an exposure wavelength (for example, ArF light (wavelength: 193 nm)). Thus, in a case where the content of the photoacid generator in the composition increases, light does not sufficiently reach the inside of the resist film, and thus, pattern collapse due to deterioration of the pattern shape occurs.

In contrast, the present inventors have found that the introduction of a group (sterically hindered group) that can be sterically hindered at an ortho-position on the phenyl group of triphenylsulfonium introduced in a photoacid generator is effective in reduction in the absorbance $\varepsilon$ of the photoacid generator. It is presumed that the introduction of a sterically hindered group into a phenyl group increases a twisting degree of a triphenylsulfonium structure, which leads to conjugation cut in the triphenylsulfonium structure (reduction in the double bonding properties), and as a result, the absorbance E of the photoacid generator is reduced. In addition, it became clear that the introduction of a sterically hindered group also contributes to improvement of the decomposition rate of the photoacid generator. This is presumed to be due to a fact that the twisting degree of the triphenylsulfonium structure increases, leading to an increase in the bond length (reduction in the binding energy) between the S atom in the center and the phenyl group. As a result, the photoacid generator having a predetermined structure has a low transmittance and high decomposability. Therefore, light easily reaches the inside of the resist film containing the photoacid generator, the photoacid generator is easily degraded, and as a result, it is possible to satisfy both of reduction in LWR and suppression of pattern collapse at higher levels.

Moreover, it became clear that introduction of a sterically hindered group also contributes to the storage stability of the photoacid generator. Currently, the reason therefor is unclear, but it is thought that there is a possibility of suppression of the reaction of the inside of the triphenylsulfonium structure with impurities in a liquid or atmosphere by the sterically hindered group.

Hereinafter, the components contained in the composition of the present invention will be described in detail, and then a pattern forming method using the composition of the present invention will be described in detail.

[1] Photoacid generator Represented by General Formula (1) or Resin Having Residue Obtained by Removing One Hydrogen Atom from Photoacid generator Represented by General Formula (1) (hereinafter also collectively referred to as a "specific photoacid generator")

The composition of the present invention contains a photoacid generator represented by General Formula (1) or a resin having a residue obtained by removing one hydrogen atom from the photoacid generator represented by General Formula (1).

Hereinafter, first, the photoacid generator represented by General Formula (1) will be described in detail.

(Photoacid Generator Represented by General Formula (1))

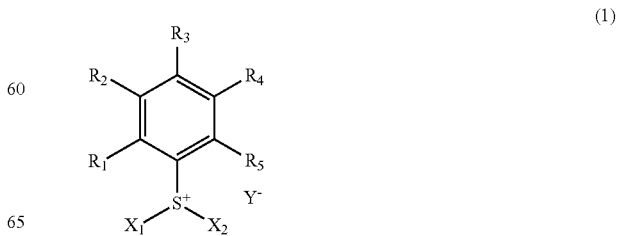

In General Formula (1), $R_1$ represents an alkyl group, an alkoxy group, an alkylthio group, a halogen atom, or a cyano group. Among those, in a view that a pattern having a lower LWR can be formed and/or a collapse of the formed pattern can be further suppressed (hereinafter simply also referred to as "superior effects of the present invention"), the alkoxy group, the alkylthio group, the halogen atom, or the cyano group is preferable, and the alkoxy group or the halogen atom is more preferable.

The alkyl group may be linear or branched. The number of carbon atoms of the alkyl group is not particularly limited, but is preferably 1 to 10, more preferably 1 to 5, and still more preferably 1 to 3.

Suitable ranges of the number of carbon atoms of the alkyl group included in the alkoxy group and the number of carbon atoms of the alkyl group included in the alkylthio group are each the same as the suitable range of the number of carbon atoms of the alkyl group as described above.

Examples of the halogen atom include a fluorine atom, a chlorine atom, a bromine atom, and an iodine atom.

$R_2$ to $R_5$ each independently represent a hydrogen atom, or a monovalent organic group. Among those, in a view of achieving superior effects of the present invention, $R_2$ to $R_5$ are each independently preferably a hydrogen atom, a cyano group, a halogen atom, an alkyl group, an aryloxy group, or an arylthio group, and more preferably a hydrogen atom or an alkyl group. Among those, in a view of achieving superior effects of the present invention, $R_5$ is preferably a monovalent organic group.

Examples of the monovalent organic group include an alkyl group, a cycloalkyl group, an aryl group, an acyl group, an alkyloxycarbonyl group, a cycloalkyloxycarbonyl group, an alkylthio group, an aryloxy group, an arylthio group, an aryloxycarbonyl group, an alkylaminocarbonyl group, a cycloalkylaminocarbonyl group, an arylaminocarbonyl group, a cyano group, a halogen atom, an amino group, a nitro group, a carboxyl group, and a hydroxyl group. These groups may further have a substituent. In addition, at least one of $R_2$, . . . , or $R_5$ is a hydrogen atom in many cases.

$X_1$ and $X_2$ each independently represent an aromatic group or an alicyclic group, or $X_1$ and $X_2$ are bonded to each other to form a ring. Hereinafter, the two aspects will be described.

The aromatic group may be monocyclic or polycyclic.

Furthermore, the aromatic group may be either an aromatic hydrocarbon group (aryl group) or an aromatic heterocyclic group (heteroaryl group).

Examples of the aromatic group include an aryl group such as a phenyl group, a tolyl group, a naphthyl group, and an anthracenyl group, and an heterocycle-containing aromatic ring group such as thiophene, furan, pyrrole, benzothiophene, benzofuran, benzopyrrole, triazine, imidazole, benzimidazole, triazole, thiadiazole, and thiazole.

The aromatic group may have a substituent. Examples of the substituent include an alkyl group, a cycloalkyl group, an aryl group, an amino group, an amido group, a ureido group, a urethane group, a hydroxyl group, a halogen atom, an alkoxy group, an alkylthio group, a cyano group, a thioether group, an acyl group, an acyloxy group, an alkoxycarbonyl group, and a nitro group.

The alicyclic group may be monocyclic or polycyclic. The alicyclic group may have, for example, a monocyclo structure, a bicyclo structure, a tricyclo structure, or a tetracyclo structure. Examples of the alicyclic group include an alicyclic hydrocarbon group. The number of carbon atoms of the alicyclic group is not particularly limited, but is preferably 5 or more, more preferably 6 to 30, and still more preferably 7 to 25.

The alicyclic group may have a substituent. Examples of the substituent include the same groups as the substituents which may be contained in the aromatic group.

Examples of the alicyclic group include groups having the partial structures listed below. Further, in each of these partial structures, it is preferable that the methylene group ($—CH_2—$) is not substituted with a heteroatom.

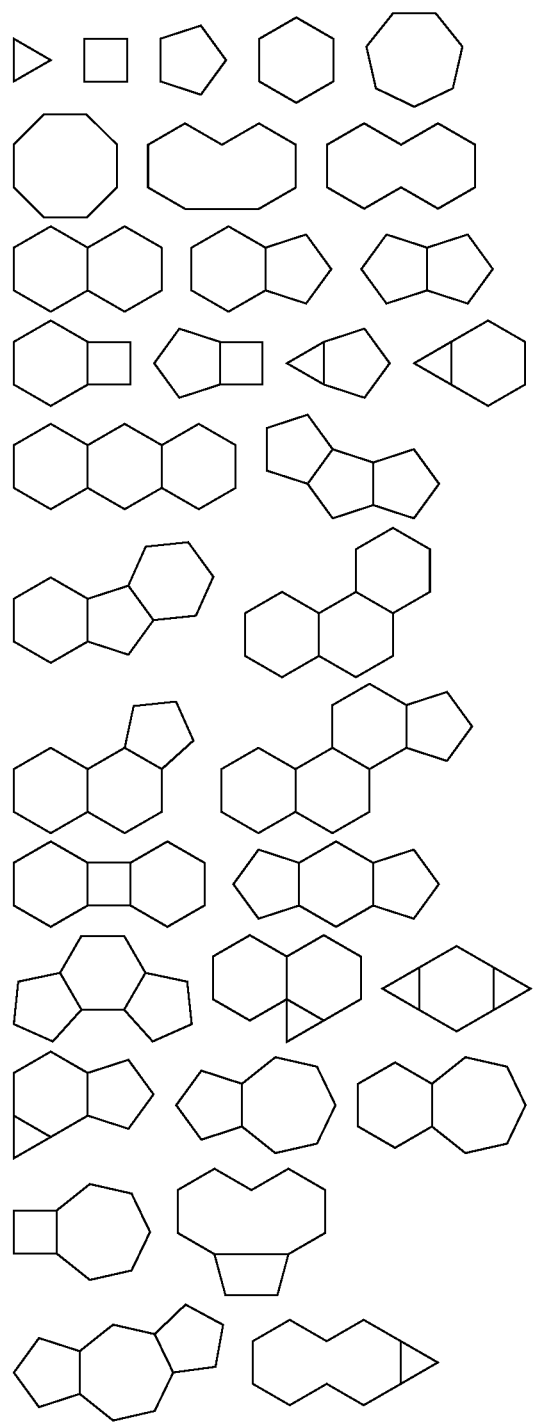

-continued

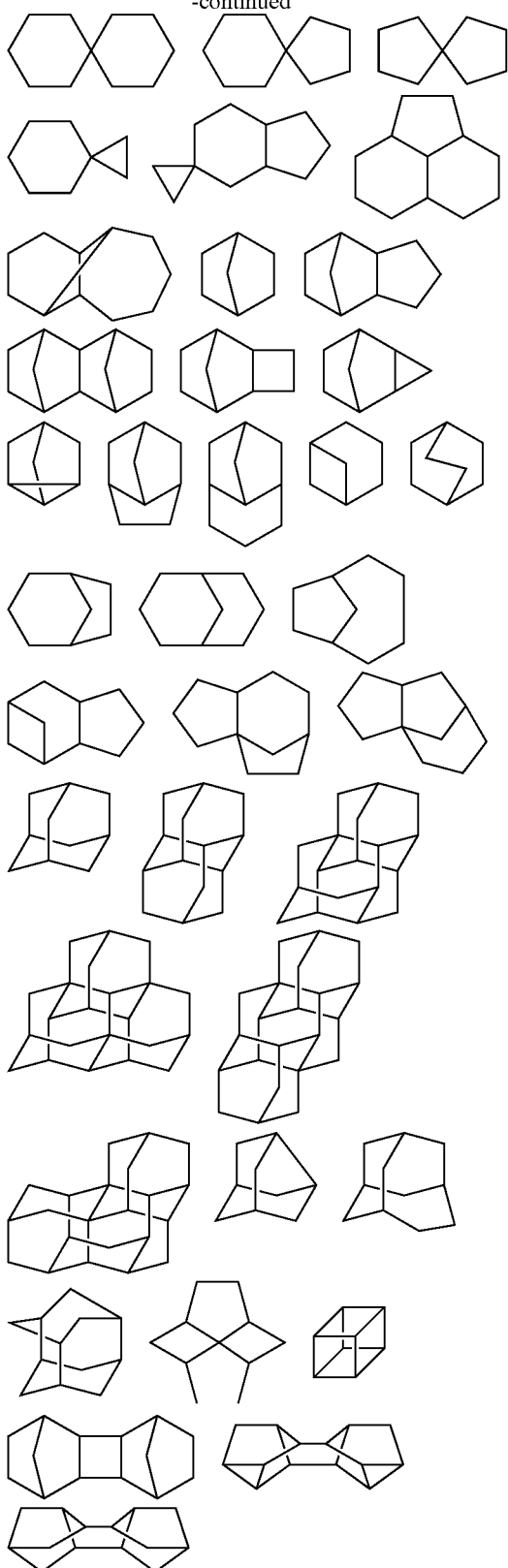

As the alicyclic group, an adamantyl group, a noradamantyl group, a decahydronaphthyl group, a tricyclodecanyl group, a tetracyclododecanyl group, a norbornyl group, a cyclopentyl group, a cyclohexyl group, a cycloheptyl group, a cyclooctyl group, a cyclodecanyl group, or a cyclododecanyl group is preferable, an adamantyl group, a norbornyl group, a cyclohexyl group, a cyclopentyl group, a tetracyclododecanyl group, or a tricyclodecanyl group is more preferable, and a cyclohexyl group, a tricyclodecanyl group, a norbornyl group, or an adamantyl group is still more preferable.

In order to form a ring by the mutual bonding of $X_1$ and $X_2$, $X_1$ and $X_2$ may be bonded directly or bonded via a divalent linking group.

Examples of the divalent linking group include a linear or branched alkylene group, a cycloalkylene group, an arylene group, a carbonyl group, an ether bond, an ester bond, an amide bond, a urethane bond, a urea bond, and a group formed by combination of two or more thereof.

Furthermore, the ring formed by the mutual bonding of $X_1$ and $X_2$ may be either an alicycle or an aromatic ring. More specifically, examples of the alicycle that is a ring formed by a sulfur atom, $X_1$, and $X_2$ include a group obtained by substituting one carbon atom of an alicyclic hydrocarbon with a sulfur atom, and examples of the aromatic ring that is a ring formed by a sulfur atom, $X_1$, and $X_2$ include a group obtained by substituting one carbon atom of an aromatic hydrocarbon with a sulfur atom.

In addition, the ring formed by the mutual bonding of $X_1$ and $X_2$ may be substituted with a substituent. Examples of the substituent include the same groups as the substituents which may be contained in the aromatic group.

$R_5$ and $X_2$ may be bonded to each other directly or via a linking group to form a ring. Examples of the linking group include the divalent linking groups as described above.

$Y^-$ represents a non-nucleophilic anion. Examples of the non-nucleophilic anion include a sulfonate anion, a carboxylate anion, a sulfonylimide anion, a bis(alkylsulfonyl)imide anion, and a tris(alkylsulfonyl)methide anion. The non-nucleophilic anion is an anion having an extremely low ability of causing a nucleophilic reaction, which can suppress the decomposition over time due to intramolecular nucleophilic reaction.

Examples of the sulfonate anion include an alkylsulfonate anion, an arylsulfonate anion, and a camphorsulfonate anion.

Examples of the carboxylate anion include an alkyl carboxylate anion, an aryl carboxylate anion, and an aralkyl carboxylate anion.

Examples of the sulfonylimide anion include a saccharin anion.

Other examples of the non-nucleophilic anion include fluorinated phosphorus, fluorinated boron, and fluorinated antimony.

The non-nucleophilic anion is preferably an alkanesulfonate anion substituted with a fluorine atom at the α-position of sulfonic acid, an arylsulfonate anion substituted with a fluorine atom or a fluorine atom-containing group, a bis(alkylsulfonyl)imide anion in which the alkyl group is substituted with a fluorine atom, or a tris(alkylsulfonyl)methide anion in which the alkyl group is substituted with a fluorine atom.

In a view of achieving superior effects of the present invention, it is preferable that the non-nucleophilic anion is an anion represented by General Formula (2) (a non-nucleophilic anion represented by General Formula (2)). In this case, it is presumed that since the volume of the generated acid is large and the diffusion of the generated acid is suppressed, an improvement of exposure latitude is further accelerated.

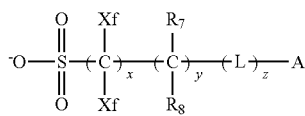
(2)

In General Formula (2), Xf's each independently represent a fluorine atom or an alkyl group substituted with at least one fluorine atom. The alkyl group in the fluorine atom-substituted alkyl group of Xf is preferably an alkyl group having 1 to 10 carbon atoms, and more preferably an alkyl group having 1 to 4 carbon atoms. Further, the fluorine atom-substituted alkyl group of Xf is preferably a perfluoroalkyl group.

Xf is preferably a fluorine atom or a perfluoroalkyl group having 1 to 4 carbon atoms.

Specific examples of Xf include a fluorine atom, $CF_3$, $C_2F_5$, $C_3F_7$, $C_4F_9$, $C_8F_{13}$, $C_6F_{13}$, $C_7F_{15}$, $C_8F_{17}$, $CH_2CF_3$, $CH_2CH_2CF_3$, $CH_2C_2F_5$, $CH_2CH_2C_2F_5$, $CH_2C_3F_7$, $CH_2CH_2C_3F_7$, $CH_2C_4F_9$, and $CH_2CH_2C_4F_9$. Among those, the fluorine atom or $CF_3$ is preferable. In particular, it is more preferable that both Xf's are fluorine atoms.

$R_7$ and $R_8$ each independently represent a hydrogen atom, a fluorine atom, an alkyl group, or an alkyl group substituted with at least one fluorine atom. The number of carbon atoms of the alkyl group is preferably 1 to 4. Specific examples of the alkyl group substituted with at least one fluorine atom include $CF_3$, $C_2F_5$, $C_3F_7$, $C_4F_9$, $C_5F_{11}$, $C_6F_{13}$, $C_7F_5$, $C_8F_{17}$, $CH_2CF_3$, $CH_2CH_2CF_3$, $CH_2C_2F_5$, $CH_2CH_2C_2F_5$, $CH_2C_3F_7$, $CH_2CH_2C_3F_7$, $CH_2C_4F_9$, and $CH_2CH_2C_4F_9$. Among those, $CF_3$ is preferable.

L represents a divalent linking group, and examples of the divalent linking group include —COO—, —OCO—, —CO—, —O—, —S—, —SO—, —$SO_2$—, —N(Ri)— (in the formula, Ri represents a hydrogen atom or alkyl), an alkylene group (preferably having 1 to 6 carbon atoms), a cycloalkylene group (preferably having 3 to 10 carbon atoms), an alkenylene group (preferably having 2 to 6 carbon atoms), and a divalent linking group formed by combination of a plurality of these groups. Among those, —COO—, —OCO—, —CO—, —$SO_2$—, —CON(Ri)-, —$SO_2$N(Ri)-, —CON(Ri)-alkylene group-, —N(Ri)CO-alkylene group-, —COO-alkylene group-, or —OCO-alkylene group— is preferable, and —COO—, —OCO—, —$SO_2$—, —CON(Ri)-, or —$SO_2$N(Ri)— is more preferable. In a case where a plurality of L's are present, they may be the same as or different from each other.

The alkyl group as Ri is preferably a linear or branched alkyl group having 1 to 20 carbon atoms, and the alkyl group may have an oxygen atom, a sulfur atom, or a nitrogen atom. Specific examples thereof include a linear alkyl group such as a methyl group, an ethyl group, an n-propyl group, an n-butyl group, an n-pentyl group, an n-hexyl group, an n-octyl group, an n-dodecyl group, an n-tetradecyl group, and n-octadecyl group, and a branched alkyl group such as an isopropyl group, an isobutyl group, a t-butyl group, a neopentyl group, and a 2-ethylhexyl group. Examples of the alkyl group having a substituent include a cyanomethyl group, a 2,2,2-trifluoroethyl group, a methoxycarbonylmethyl group, and an ethoxycarbonylmethyl group.

A represents a cyclic organic group. The cyclic organic group (organic group including a cyclic structure) is not particularly limited as long as it has a cyclic structure, and examples thereof include an alicyclic group, an aryl group, a heterocyclic group (including the group having aromaticity or not having aromaticity, and including, for example, a tetrahydropyran ring and a lactone ring structure.

The alicyclic group may be monocyclic or polycyclic, and is preferably a monocyclic cycloalkyl group such as a cyclopentyl group, a cyclohexyl group, and a cyclooctyl group, or a polycyclic cycloalkyl group such as a norbornyl group, a norbornenyl group, a tricyclodecanyl group (for example, a tricyclo[5.2.1.0$^{(2,6)}$]decanyl group), a tetracyclodecanyl group, a tetracyclododecanyl group, and an adamantyl group. Further, a nitrogen atom-containing alicyclic group such as a piperidine group, a decahydroquinoline group, and a decahydroisoquinoline group is also preferable. Among those, an alicyclic group with a bulky structure having 7 or more carbon atoms, such as a norbornyl group, a tricyclodecanyl group, a tetracyclodecanyl group, a tetracyclododecanyl group, an adamantyl group, an decahydroquinoline group, and a decahydroisoquinoline group is preferable in a view that the diffusivity into a film in the post-exposure baking (PEB) step can be suppressed, and thus, the exposure latitude can be improved.

Examples of a ring constituting the aryl group include a benzene ring, a naphthalene ring, a phenanthrene ring, and an anthracene ring. Among those, a naphthalene ring with a low absorbance is preferable from the viewpoint of a light absorbance at 193 nm.

Examples of a ring constituting the heterocyclic group include a furan ring, a thiophene ring, a benzofuran ring, a benzothiophene ring, a dibenzofuran ring, a dibenzothiophene ring, and a pyridine ring. Among those, a furan ring, a thiophene ring, and a pyridine ring are preferable.

The cyclic organic group may have a substituent, and examples of the substituent include an alkyl group (may be linear, branched, or cyclic; preferably having 1 to 12 carbon atoms), an aryl group (preferably having 6 to 14 carbon atoms), a hydroxyl group, an alkoxy group, an ester group, an amido group, a urethane group, a ureido group, a thioether group, a sulfonamido group, a sulfonic acid ester group, and a cyano group.

Incidentally, the carbon constituting the cyclic organic group (the carbon contributing to ring formation) may be a carbonyl carbon.

x represents an integer of 1 to 20. y represents an integer of 0 to 10. z represents an integer of 0 to 10. In a case where y is 2 or more, a plurality of $R_7$'s and $R_8$'s may be the same as or different from each other. In a case where z is 2 or more, a plurality of L's may be the same as or different from each other.

x is preferably 1 to 8, and y is more preferably 1 to 4, and still more preferably 1. y is preferably 0 to 4, more preferably 0 or 1, and still more preferably 0. z is preferably 0 to 8, more preferably 0 to 4, and still more preferably 1 to 2.

In General Formula (2), preferred examples of a combination of the partial structures other than A include $SO_3^-$—$CF_2$—$CH_2$—OCO—, $SO_3^-$—$CF_2$—CHF—$CH_2$—OCO—, $SO_3^-$—$CF_2$—COO—, $SO_3^-$—$CF_2$—$CF_2$—$CH_2$—, and $SO_3^-$—$CF_2$—CH($CF_3$)—OCO—.

Examples of the anion represented by General Formula (2) include the following ones.

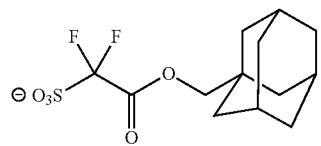

-continued
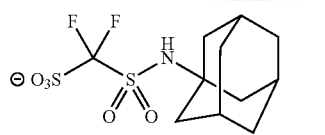
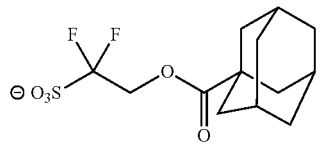
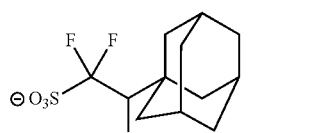
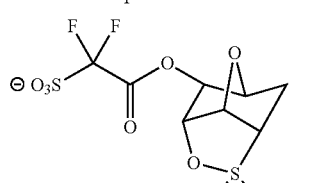
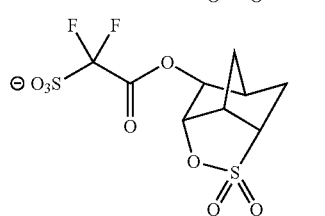
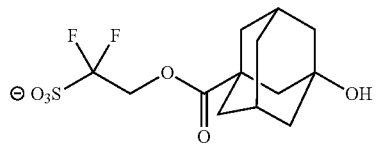
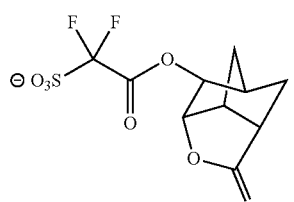
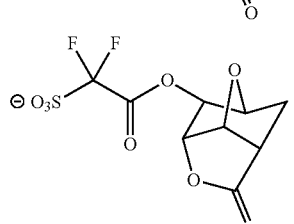
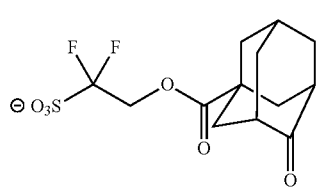
-continued
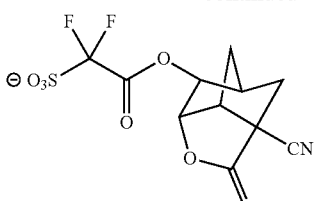
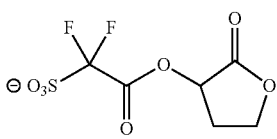
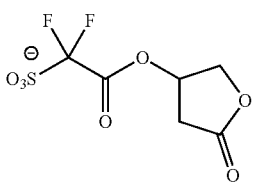
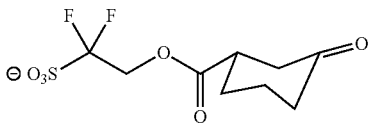
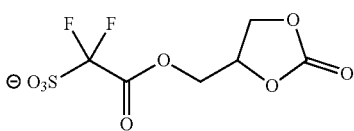
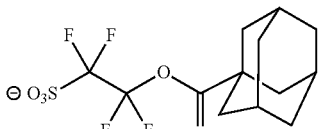
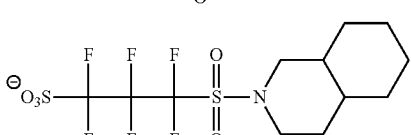
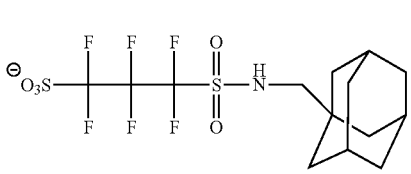
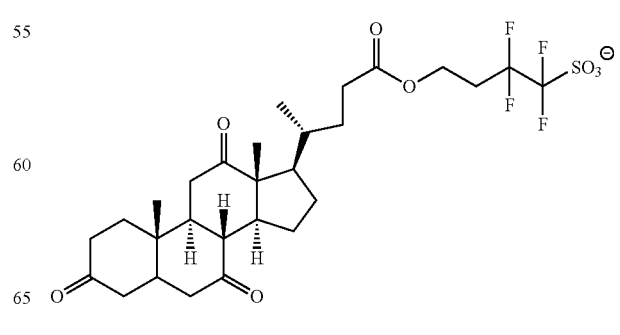

-continued

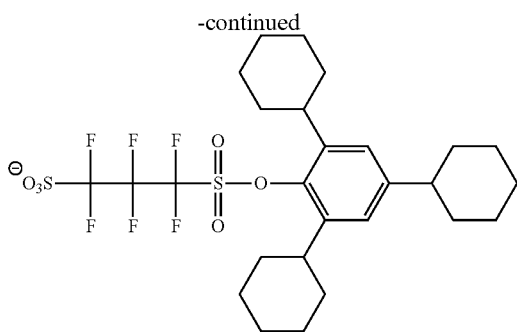

(Photoacid Generator Represented by General Formula (1-A))

Suitable aspects of the photoacid generator represented by General Formula (1) include a photoacid generator represented by General Formula (1-A) in a view of achieving superior effects of the present invention.

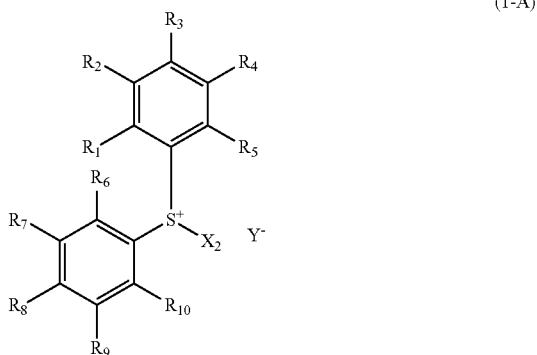

(1-A)

In General Formula (1-A), $R_1$ and $R_6$ each independently represent an alkyl group, an alkoxy group, an alkylthio group, a halogen atom, or a cyano group. The definitions and the suitable aspects of the respective groups represented by $R_1$ and $R_6$ are the same as the definitions and the suitable aspects as the respective groups described for $R_1$ in General Formula (1) as described above.

$R_2$ to $R_5$ and $R_7$ to $R_{10}$ each independently represent a hydrogen atom or a monovalent organic group. Among those, in a view of achieving superior effects of the present invention, $R_2$ to $R_5$ and $R_7$ to $R_{10}$ are each preferably a hydrogen atom, an alkyl group, a cyano group, a halogen atom, an aryloxy group, or an arylthio group, and more preferably a hydrogen atom or an alkyl group.

The definition of the monovalent organic group is the same as described above.

$X_2$ represents an aromatic group or an alicyclic group. The definitions of the aromatic group and the alicyclic group are the same as described above. $R_5$ and $X_2$ may be bonded to each other directly or via a linking group to form a ring. Examples of the linking group include the divalent linking groups as described above.

$Y^-$ represents a non-nucleophilic anion. The definition of Y is the same as described above.

(Photoacid Generator Represented by General Formula (1-B))

The most optimal aspects of the photoacid generator represented by General Formula (1) include a photoacid generator represented by General Formula (1-B) in a view of achieving superior effects of the present invention.

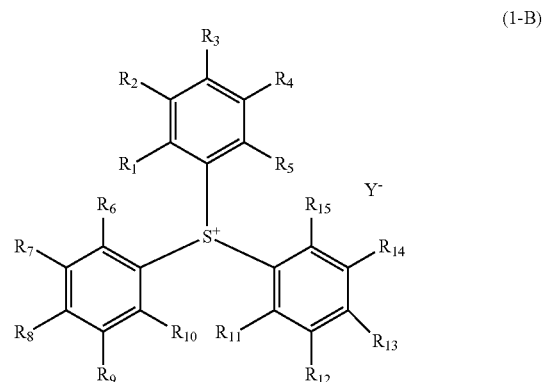

(1-B)

In General Formula (1-B), $R_1$, $R_6$, and $R_{11}$ each independently represent an alkyl group, an alkoxy group, an alkylthio group, a halogen atom, or a cyano group. The definitions and the suitable aspects of the respective groups represented by $R_1$, $R_6$, and $R_{11}$ are the same as the definitions and the suitable aspects of the respective groups described for $R_1$ in General Formula (1) as described above.

$R_2$ to $R_5$, $R_7$ to $R_{10}$, and $R_{12}$ to $R_{15}$ each independently represent a hydrogen atom or a monovalent organic group. Among those, $R_2$ to $R_5$, $R_7$ to $R_{10}$, and $R_{12}$ to $R_{15}$ are each preferably a hydrogen atom, a cyano group, a halogen atom, an alkyl group, an aryloxy group, or an arylthio group, and more preferably a hydrogen atom or an alkyl group, in a view of achieving superior effects of the present invention.

The definition of the monovalent organic group is the same as described above.

$Y^-$ represents a non-nucleophilic anion. The definition of the $Y^-$ is the same as described above.

In a case where the relative absorbance of the photoacid generator represented by General Formula (1) is taken as $\varepsilon_r$ and the relative quantum efficiency is taken as $\varphi_r$ with a triphenylsulfonium nonaflate as a reference, the relative absorbance $\varepsilon_r$ of the photoacid generator represented by General Formula (1) is not particularly limited, but is preferably 0.4 to 0.8, more preferably 0.45 to 0.7, still more preferably 0.5 to 0.65, and particularly preferably 0.55 to 0.6.

Furthermore, the relative absorbance $\varepsilon_r \times$ the relative quantum efficiency $\varphi_r$ of the photoacid generator represented by General Formula (1) is not particularly limited, but is preferably 0.5 to 1.0, more preferably 0.55 to 0.9, still more preferably 0.6 to 0.8, and particularly preferably 0.65 to 0.7.

The relative absorbance $\varepsilon_r$ of the photoacid generator represented by General Formula (1) is a value which is normalized by setting the molar absorbance coefficient $\varepsilon_{TPS}$ of triphenylsulfonium nonaflate as 1, and specifically, is a value which is calculated using the following equation.

$$\varepsilon_r = \varepsilon_z / \varepsilon_{TPS}$$

In the equation, $\varepsilon_r$ represents the relative absorbance of the photoacid generator represented by General Formula (1).

$\varepsilon_z$ represents the molar absorbance coefficient of the photoacid generator represented by General Formula (1).

$\varepsilon_{TPS}$ represents the molar absorbance coefficient of triphenylsulfonium nonaflate.

The molar absorbance coefficient of the photoacid generator represented by General Formula (1) as a subject is calculated in accordance with a Lambert-Beer equation from an absorbance (A) with respect to light at a wavelength of 193 nm and a measured solvent concentration (C) after measuring the ultraviolet ray (UV) spectrum of a measurement solution in which the photoacid generator represented by General Formula (1) is dissolved in a solvent.

The relative quantum efficiency φr of the photoacid generator represented by General Formula (1) is a value which is normalized by setting the molar absorbance coefficient $\varepsilon_{TPS}$ and the quantum yield $\varphi_{TPS}$ of triphenylsulfonium nonaflate as 1, and specifically, is calculated using the following equation.

$$\varphi_r = (\varphi_{TPS} \times \varepsilon_{TPS} \times E_{TPS})/(\varepsilon_r \times E_r)$$

In the equation, $\varepsilon_{TPS}$ and $\varphi_{TPS}$ are 1.

$E_{TPS}$ represents the sensitivity of triphenylsulfonium nonaflate.

$E_r$ represents the sensitivity of the photoacid generator represented by General Formula (1).

$\varepsilon_r$ represents the relative absorbance of the photoacid generator represented by General Formula (1) as calculated by the method described above.

$\varphi_r$ represents the relative quantum efficiency of the photoacid generator represented by General Formula (1).

The sensitivity $E_{TPS}$ of triphenylsulfonium nonaflate which is used for the calculation of $\varphi_r$ of the photoacid generator represented by General Formula (1) is calculated by the following method.

First, a resist solution with a concentration of the solid content 3.5% by mass is obtained by dissolving 10 g of Resin Polymer (1) described below, 0.3 g of a basic compound, 2,6-diisopropyl aniline (DIA), and 2.0 g of triphenylsulfonium nonaflate in a solvent (propylene glycol monomethyl ether acetate (PGMEA)).

A resist film with a film thickness of 100 nm is formed using the obtained resist solution, and the resist film is exposed using an ArF excimer laser scanner.

Thereafter, the exposed resist film is heated at 100° C. for 60 seconds. Then, the heated resist film is developed by paddling in butyl acetate for 30 seconds, and rinsed with methyl isobutyl carbinol (MIBC). Thereafter, the rinsed resist film is baked at 90° C. for 60 seconds.

The exposure dose at a time when the film thickness after baking reaches 10 nm or more by increasing the exposure dose in steps from 1 mJ/cm² to 0.3 mJ/cm² is defined as the sensitivity Ers of triphenylsulfonium nonaflate.

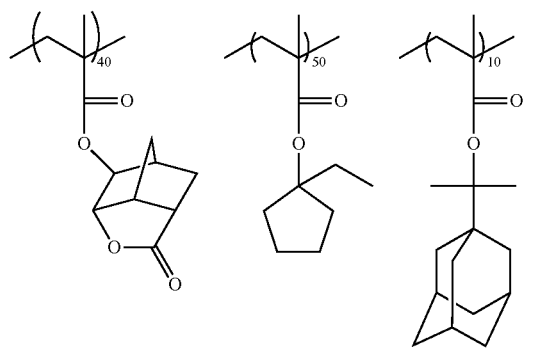

Polymer (1)

Mw = 9500
Mw/Mn = 1.60

The sensitivity $E_r$ of the photoacid generator represented by General Formula (1) other than triphenylsulfonium nonaflate is measured in the same manner as the measurement of the sensitivity $E_{TPS}$ except that triphenylsulfonium nonaflate is changed to the photoacid generator represented by General Formula (1) in the measurement of the sensitivity Errs described above.

(Resin Having Residue Obtained by Removing One Hydrogen Atom from Photoacid Generator Represented by General Formula (1)) (Hereinafter Simply Also Referred to as a "Specific Resin")

The specific resin is a resin having a residue (hereinafter simply also referred to as a "specific residue") obtained by removing one hydrogen atom from the photoacid generator represented by General Formula (1). In other words, the specific resin is a resin having the photoacid generator represented by General Formula (1) as a partial structure.

The specific residue contained in the specific resin is a monovalent group formed by removing one hydrogen atom from the photoacid generator represented by General Formula (1). The hydrogen atom to be removed is not particularly limited, and may be any one of hydrogen atoms included in the photoacid generator represented by General Formula (1).

The specific residue may be introduced into any one of a side chain and a terminal of the specific resin.

The main chain skeleton of the specific resin is not particularly limited, and examples thereof include known resin skeletons such as a poly(meth)acrylate skeleton, a poly(ester) skeleton, a polyurethane skeleton, a polyether skeleton, and a polycarbonate skeleton.

The specific resin preferably has a repeating unit represented by General Formula (1-C) (hereinafter simply also referred to as a "specific repeating unit").

(1-C)

In General Formula (1-C), $R_{20}$ to $R_{22}$ each independently represent a hydrogen atom or a monovalent organic group. The definition of the monovalent organic group is the same as described above. Among those, $R_{20}$ and $R_{21}$ are each preferably a hydrogen atom. As $R_{22}$, a hydrogen atom or an alkyl group is preferable.

$L_A$ represents a single bond or a divalent linking group. The definition of the divalent linking group is the same as that of the divalent linking group represented by L in General Formula (2) as described above.

Z represents a residue obtained by removing one hydrogen atom from the photoacid generator represented by General Formula (1). As Z, a group represented by General Formula (1-D) is preferable. * represents a binding position.

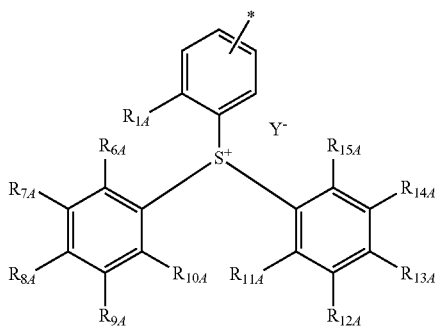

(1-D)

In General Formula (1-D), $R_{1A}$, $R_{6A}$, and $R_{11A}$ each independently represent a hydrogen atom, an alkyl group, an alkoxy group, an alkylthio group, a halogen atom, or a cyano group, and at least one of $R_{1A}$, $R_{6A}$, or $R_{11A}$ represents a group other than a hydrogen atom.

The definitions and the suitable aspects of the respective groups represented by $R_{1A}$, $R_{6A}$, and $R_{11A}$ are the same as the definitions and the suitable aspects of the respective groups described for $R_1$ in General Formula (1) as described above.

$R_{7A}$ to $R_{10A}$ and $R_{12A}$ to $R_{15A}$ each independently represent a hydrogen atom or a monovalent organic group. Among those, in a view of achieving superior effects of the present invention, $R_{7A}$ to $R_{11A}$, and $R_{12A}$ to $R_{15A}$ are each preferably a hydrogen atom, an alkyl group, a cyano group, a halogen atom, an aryloxy group, or an arylthio group, and more preferably a hydrogen atom or an alkyl group.

The definition of the monovalent organic group is the same as described above.

The content of the specific repeating unit in the specific resin is not particularly limited, and in a view of achieving superior effects of the present invention, is preferably 10% to 100% by mole, and more preferably 40% to 100% by mole, with respect to all the repeating units in the specific resin.

In addition, the specific resin may include other repeating units, in addition to the specific repeating units.

The total content of the photoacid generator represented by General Formula (1) and the resin having a residue obtained by removing one hydrogen atom from the photoacid generator represented by General Formula (1) is preferably 0.1% to 30% by mass, more preferably 0.5% to 25% by mass, still more preferably 1% to 23% by mass, and particularly preferably 3% to 20% by mass, with respect to the total solid content of the composition.

In addition, in a case where the composition includes only any one of the photoacid generator represented by General Formula (1) and the specific resin, the content of the photoacid generator represented by General Formula (1) and the specific resin may be any resin in the range.

The composition of the present invention may include one kind or two or more kinds of the photoacid generator represented by General Formula (1).

The composition of the present invention may further include a photoacid generator other than the photoacid generator represented by General Formula (1). Examples of the photoacid generator other than the photoacid generator represented by General Formula (1) include the photoacid generators disclosed in paragraphs [0265] to [0452] of US2016/0026083A1. As the photoacid generator used in combination with the photoacid generator represented by General Formula (1), an onium salt compound formed of triphenylsulfonium cations and anions is preferable, and as the triphenylsulfonium cation, an unsubstituted triphenylsulfonium cation is more preferable.

[2] Resin Including Repeating Unit Having Group that Decomposes by Action of Acid to Generate Alkali-Soluble Group (Hereinafter Also Referred to as a "Resin (B)")

The composition of the present invention may further contain a resin including a repeating unit (hereinafter also referred to as an "acid-decomposable repeating unit") having a group (hereinafter also referred to as an "acid-decomposable group") that decomposes by the action of an acid to generate an alkali-soluble group.

Furthermore, the resin (B) is preferably insoluble or sparingly soluble in an alkali developer.

Hereinafter, the resin (B) will be described in detail.

(Repeating Unit Having Acid-Decomposable Group)

The resin (B) may include a repeating unit having an acid-decomposable group on a main chain or a side chain of the resin or on both the main chain and the side chain.

The acid-decomposable group preferably has a structure which is protected by a group in which an alkali-soluble group decomposes to leave by an action of an acid.

As the alkali-soluble group, a phenolic hydroxyl group, a carboxyl group, a fluorinated alcohol group, a sulfonic acid group, a sulfonamido group, a sulfonylimido group, an (alkylsulfonyl)(alkylcarbonyl)methylene group, an (alkylsulfonyl)(alkylcarbonyl)imido group, a bis(alkylcarbonyl)methylene group, a bis(alkylcarbonyl)imido group, a bis(alkylsulfonyl)methylene group, a bis(alkylsulfonyl)imido group, a tris(alkylcarbonyl)methylene group, and a tris(alkylsulfonyl)methylene group.

As the alkali-soluble group, a carboxyl group, a fluorinated alcohol group (preferably hexafluoroisopropanol), or a sulfonic acid group is preferable.

As the acid-decomposable group, a group in which a hydrogen atom of the acid-soluble group is substituted with a group that leaves by the action of an acid is preferable.

Examples of the group that leaves by an acid include —C($R_{36}$)($R_{37}$)($R_{38}$), —C($R_{36}$)($R_{37}$)(O$R_{39}$), and —C($R_{01}$)($R_{02}$)(O$R_{39}$).

In the formulae, $R_{36}$ to $R_{39}$ each independently represent an alkyl group, a cycloalkyl group, an aryl group, an aralkyl group, or an alkenyl group. $R_{36}$ and $R_{37}$ may be bonded to each other to form a ring.

$R_{01}$ to $R_{02}$ each independently represent a hydrogen atom, an alkyl group, a cycloalkyl group, an aryl group, an aralkyl group, or an alkenyl group.

As the acid-decomposable group, a cumyl ester group, an enol ester group, an acetal group, an acetal ester group, or a tertiary alkyl ester group is preferable, and a tertiary alkyl ester group is more preferable.

As the repeating unit having an acid-decomposable group that can be included in the resin (B), a repeating unit represented by General Formula (AI) is preferable.

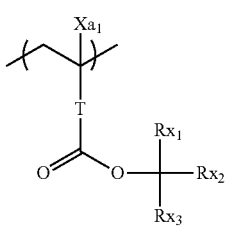

(AI)

In General Formula (AI), $Xa_1$ represents a hydrogen atom, a methyl group which may have a substituent, or a group represented by —$CH_2$—$R_9$. $R_9$ represents a hydroxyl group or a monovalent organic group, examples thereof include an alkyl group having 5 or less carbon atoms, and an acyl group, and $R_9$ is preferably an alkyl group having 3 or less carbon atoms, and more preferably a methyl group. As $Xa_1$, a hydrogen atom, a methyl group, a trifluoromethyl group, or a hydroxymethyl group is preferable.

T represents a single bond or a divalent linking group.

$Rx_1$ to $Rx_3$ each independently represent an (linear or branched) alkyl group or a (monocyclic or polycyclic) cycloalkyl group.

At least two of $Rx_1$ to $Rx_3$ may be bonded to each other to form a (monocyclic or polycyclic) cycloalkyl group.

Examples of the divalent linking group represented by T include an alkylene group, a —COO-Rt- group, and an —O-Rt- group. In the formulae, Rt represents an alkylene group or a cycloalkylene group.

T is preferably a single bond or a —COO-Rt- group. Rt is preferably an alkylene group having 1 to 5 carbon atoms, and more preferably a —$CH_2$— group, or a —$(CH_2)_3$— group.

Preferred examples of the alkyl group of each of $Rx_1$ to $Rx_3$ include an alkyl group having 1 to 4 carbon atoms, such as a methyl group, an ethyl group, an n-propyl group, an isopropyl group, an n-butyl group, an isobutyl group, and a t-butyl group.

As the cycloalkyl group of each of $Rx_1$ to $Rx_3$, a monocyclic cycloalkyl group such as a cyclopentyl group and a cyclohexyl group, or a polycyclic cycloalkyl group such as a norbornyl group, a tetracyclodecanyl group, a tetracyclododecanyl group, and an adamantyl group is preferable.

As the cycloalkyl group formed by the bonding of at least two of $Rx_1$ to $Rx_3$, a monocyclic cycloalkyl group such as a cyclopentyl group and a cyclohexyl group, or a polycyclic cycloalkyl group such as a norbornyl group, a tetracyclodecanyl group, a tetracyclododecanyl group, and an adamantyl group is preferable. Among those, as the cycloalkyl group, a monocyclic cycloalkyl group having 5 or 6 carbon atoms is particularly preferable.

In addition, an aspect in which $Rx_1$ is a methyl group or an ethyl group, and $Rx_2$ and $Rx_3$ are bonded to each other to form the above-mentioned cycloalkyl group is preferable.

Each of the groups may have a substituent. Examples of the substituent include an alkyl group (having 1 to 4 carbon atoms), a halogen atom, a hydroxyl group, an alkoxy group (having 1 to 4 carbon atoms), a carboxyl group, and an alkoxycarbonyl group (having 2 to 6 carbon atoms). As the substituent, the groups having 8 or less carbon atoms are preferable.

The total content of the repeating unit having an acid-decomposable group is preferably 10% to 70% by mole, and more preferably 40% to 70% by mole, with respect to all the repeating units in the resin (B).

Specific examples of the repeating unit having an acid-decomposable group are set forth below, but the present invention is not limited thereto.

In the specific examples, $Rx$, and $Xa_1$ each represent a hydrogen atom, $CH_3$, $CF_3$, or $CH_2OH$. Rxa and Rxb each represent an alkyl group having 1 to 4 carbon atoms. Z represents a substituent having a plurality of polar groups, and in a case where they are present in plural numbers, they are each independent. p represents 0 or a positive integer.

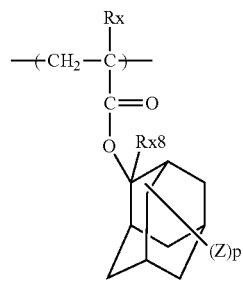

1

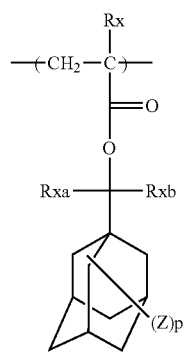

2

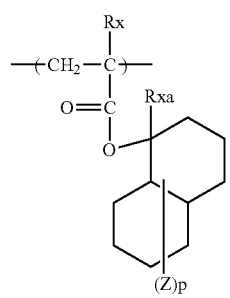

3

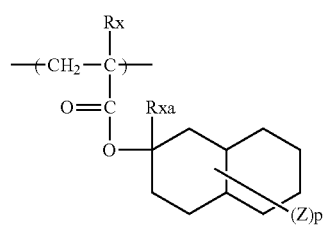

4

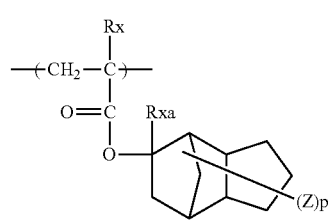

5

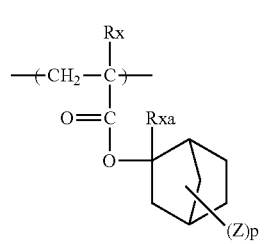

6

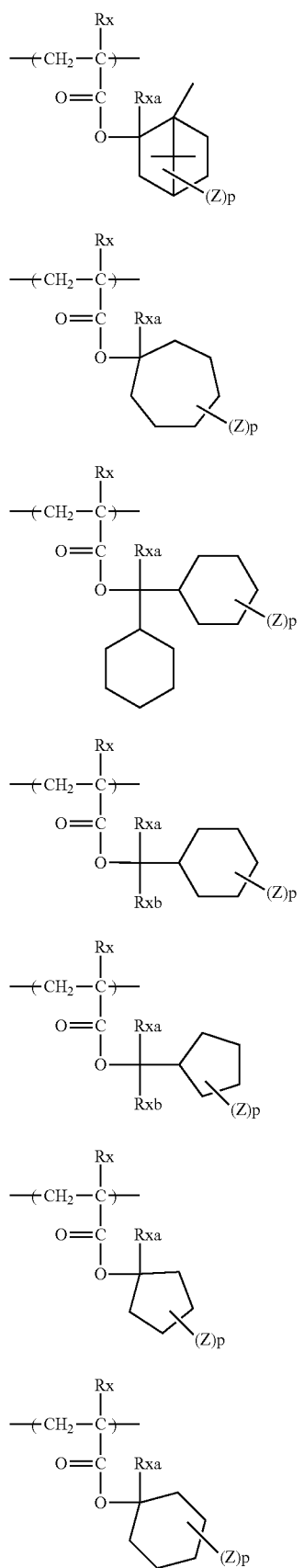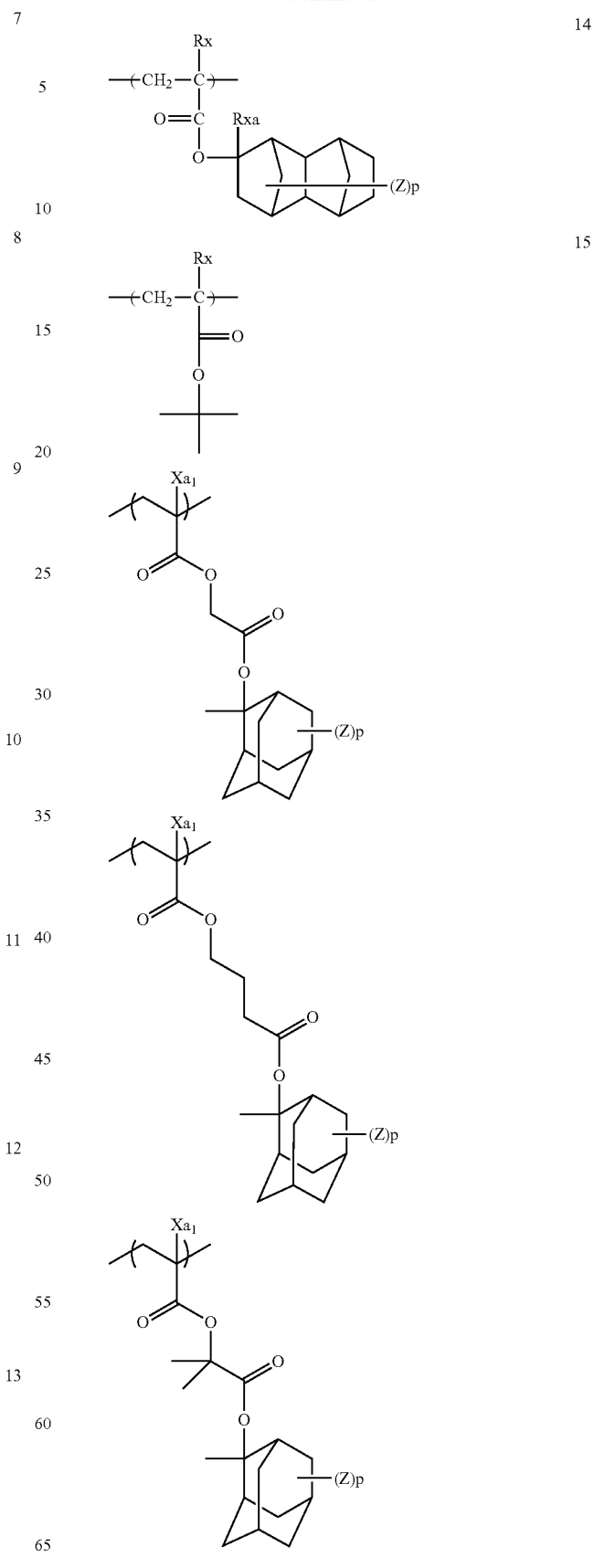

-continued
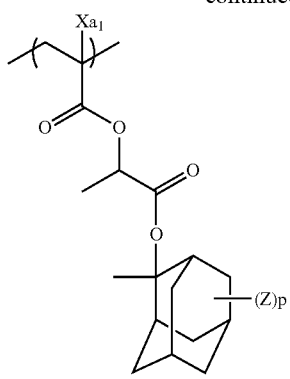
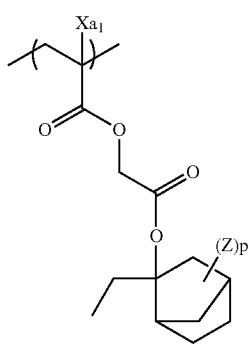
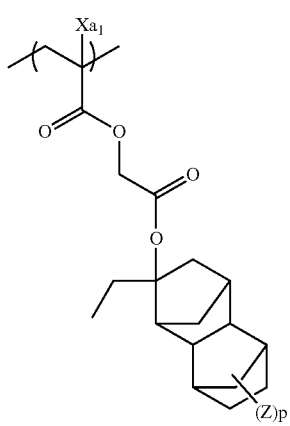
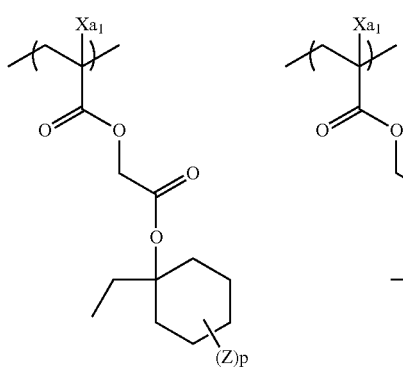
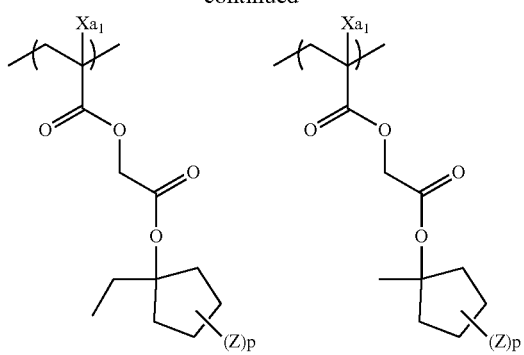
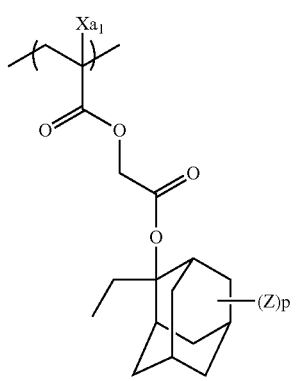
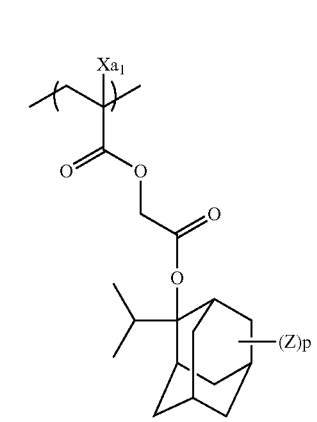
The resin (B) is a repeating unit represented by General Formula (AI), and preferably a resin including at least any one of a repeating unit represented by General Formula (1) and a repeating unit represented by General Formula (II).
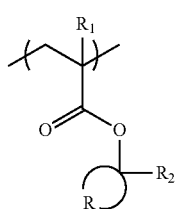
(I)

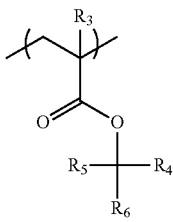

(II)

In General Formulae (I) and (II), $R_1$ and $R_3$ each independently represent a hydrogen atom, a methyl group which may have a substituent, or a group represented by —$CH_2$—$R_9$. $R_9$ represents a monovalent organic group.

$R_2$, $R_4$, $R_5$, and $R_5$ each independently represent an alkyl group or a cycloalkyl group.

R represents an atomic group required to form an alicyclic structure together with a carbon atom.

As $R_1$, a hydrogen atom, a methyl group, a trifluoromethyl group, or a hydroxymethyl group is preferable.

The alkyl groups in $R_2$ may be linear or branched, and may have a substituent.

The cycloalkyl group in $R_2$ may be monocyclic or polycyclic, may have a substituent.

$R_2$ is preferably an alkyl group, and is more preferably an alkyl group having 1 to 10 carbon atoms, and still more preferably an alkyl group having 1 to 5 carbon atoms, and examples thereof include a methyl group and an ethyl group.

R represents an atomic group required to form an alicyclic structure together with a carbon atom. The alicyclic structure formed by R is preferably a monocyclic alicyclic structure. The number of carbon atoms of R is preferably 8 or less, more preferably 3 to 7, and still more preferably 5 or 6.

$R_3$ is preferably a hydrogen atom or a methyl group, and more preferably a methyl group.

The alkyl group in each of $R_4$, $R_5$, and $R_6$ may be linear or branched, and may have a substituent. As the alkyl group, an alkyl group having 1 to 4 carbon atoms, such as a methyl group, an ethyl group, an n-propyl group, an isopropyl group, an n-butyl group, an isobutyl group, and a t-butyl group is preferable.

The cycloalkyl group in each of $R_4$, $R_5$, and $R_6$ may be monocyclic or polycyclic, and may have a substituent. As the cycloalkyl group, a monocyclic cycloalkyl group such as a cyclopentyl group and a cyclohexyl group, or a polycyclic cycloalkyl group such as a norbornyl group, a tetracyclodecanyl group, a tetracyclododecanyl group, and an adamantyl group is preferable.

Examples of the repeating unit represented by General Formula (1) include a repeating unit represented by General Formula (3).

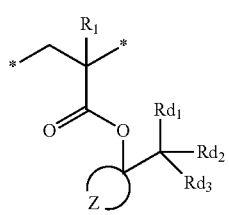

(3)

In General Formula (3), $R_1$ has the same definition as $R_1$ in General Formula (1).

$Rd_1$ to $Rd_3$ each independently represent a hydrogen atom or an alkyl group.

Z represents a monocyclic structure.

Examples of the alkyl group of each of $Rd_1$ to $Rd_3$ include an alkyl group having 1 to 4 carbon atoms. The alkyl group having 1 to 4 carbon atoms of each of $Rd_1$ to $Rd_3$ is preferably a methyl group.

Examples of the monocyclic structure of Z include a monocyclic cycloalkyl group such as a cyclopentyl group and a cyclohexyl group. The monocyclic cycloalkyl group preferably has 8 or less carbon atoms. The monocyclic cycloalkyl group of Z having 8 or less carbon atoms is preferably a cyclopentyl group or a cyclohexyl group.

Furthermore, examples of the repeating unit represented by General Formula (1) include a repeating unit represented by General Formula (1-a).

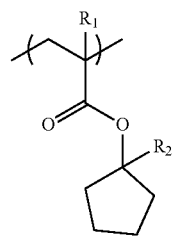

(1-a)

In the formula, $R_1$ and $R_2$ each have the same definitions as in General Formula (I).

The repeating unit represented by General Formula (II) is preferably a repeating unit represented by General Formula (II-1).

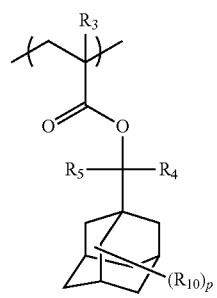

(II-1)

In Formula (II-1), $R_3$ to $R_5$ each have the same definitions as in General Formula (II).

$R_{10}$ represents a substituent including a polar group. In a case where a plurality of $R_{10}$'s are present, they may be the same as or different from each other. Examples of the substituent including a polar group include a linear or branched alkyl group having a hydroxyl group, a cyano group, an amino group, an alkylamido group, or a sulfonamido group, and a cycloalkyl group, with the alkyl group having a hydroxyl group being preferable. As the branched alkyl group, an isopropyl group is preferable.

p represents an integer of 0 to 15. p is preferably 0 to 2, and more preferably 0 or 1.

The resin (B) is more preferably a resin including at least one of the repeating unit represented by General Formula (I) and the repeating unit represented by General Formula (II).

Further, in another embodiment, the resin (B) is more preferably a resin including at least two kinds of repeating units represented by General Formula (I).

In a case where the resin (B) uses an acid-decomposable repeating unit in combination therewith, preferred combinations thereof are shown below. In the following formulae, R's each independently represent a hydrogen atom or a methyl group.

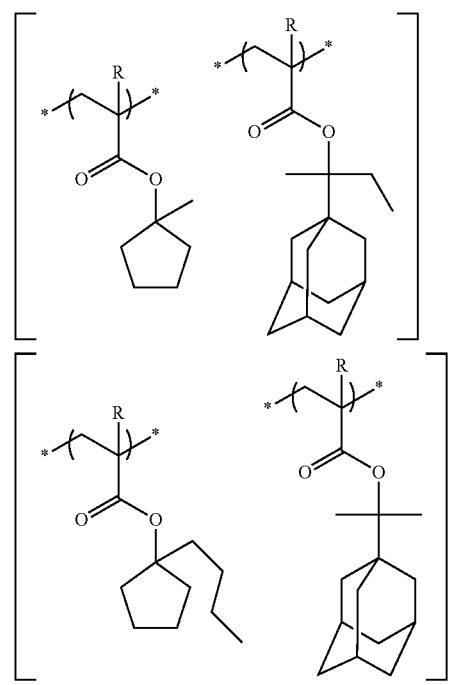

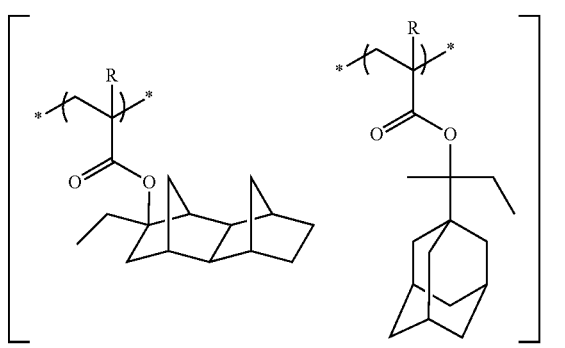

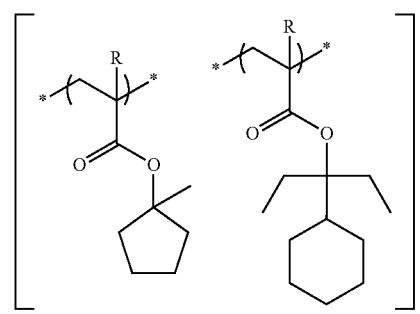

-continued

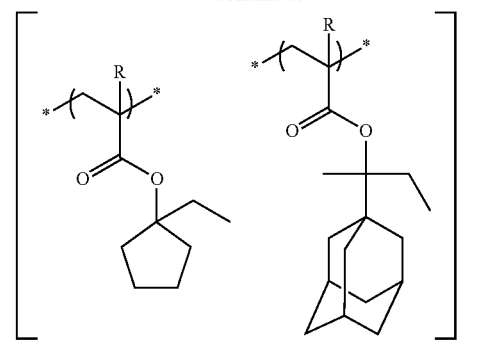

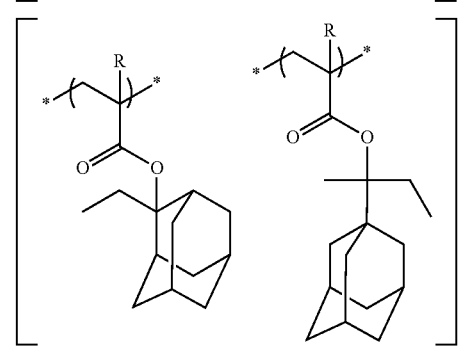

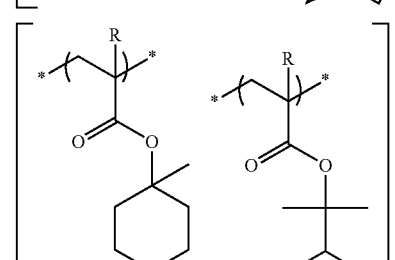

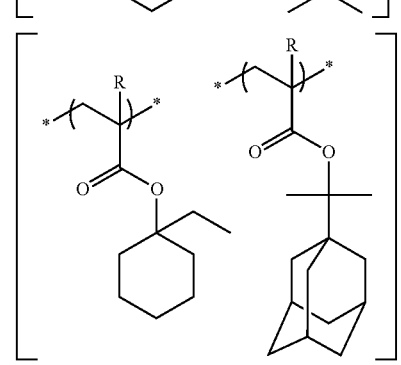

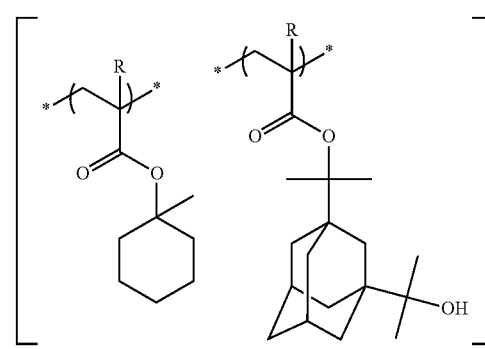

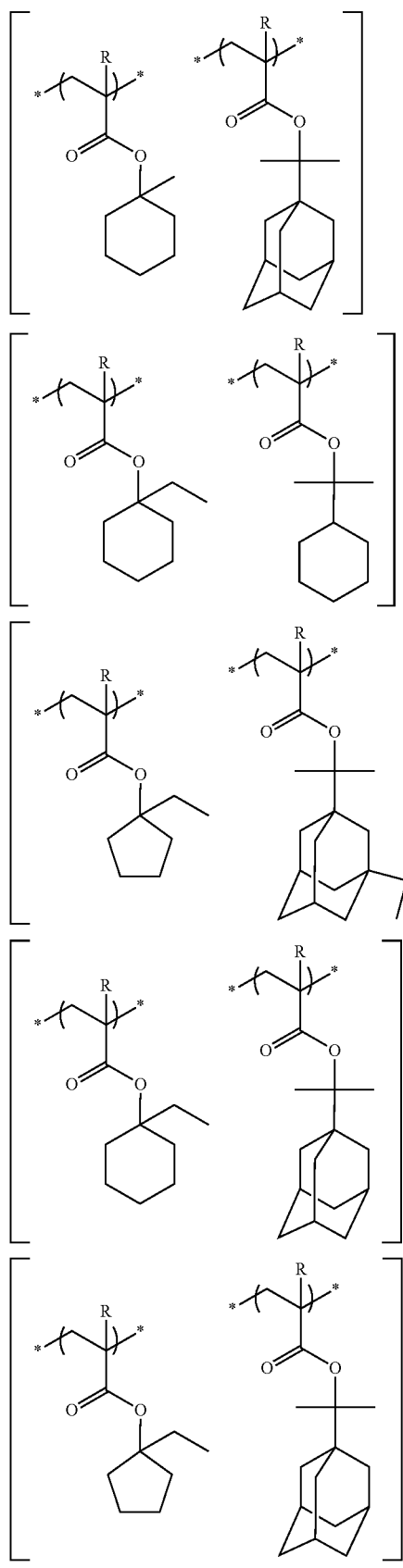
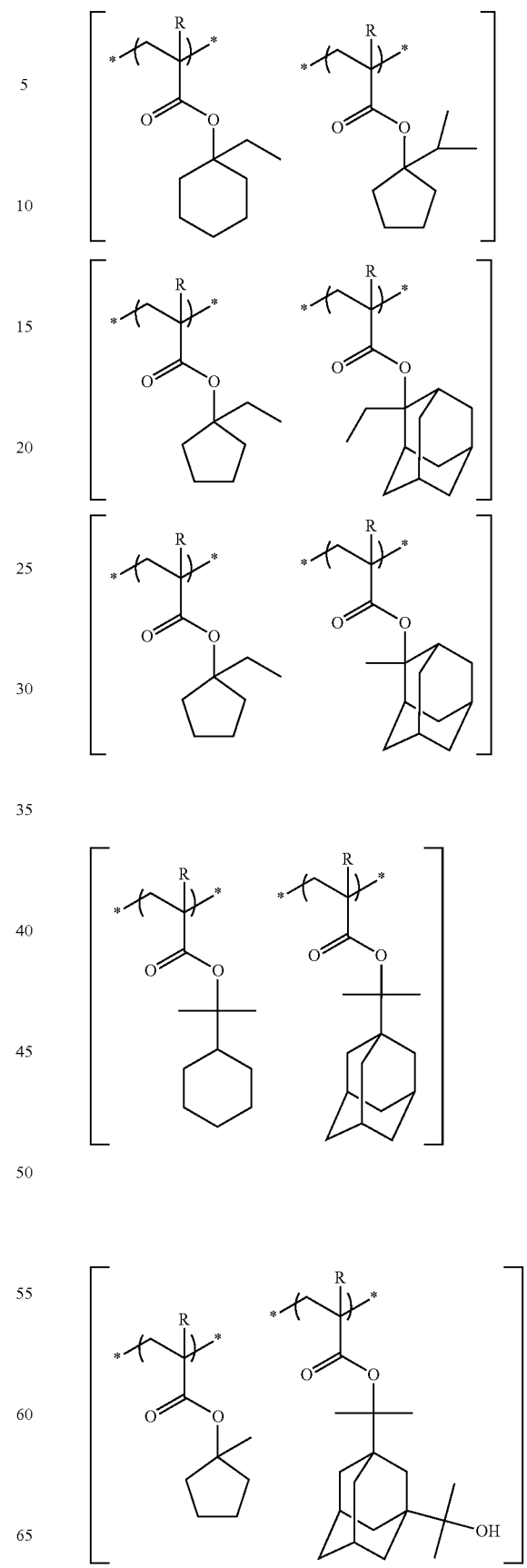

-continued

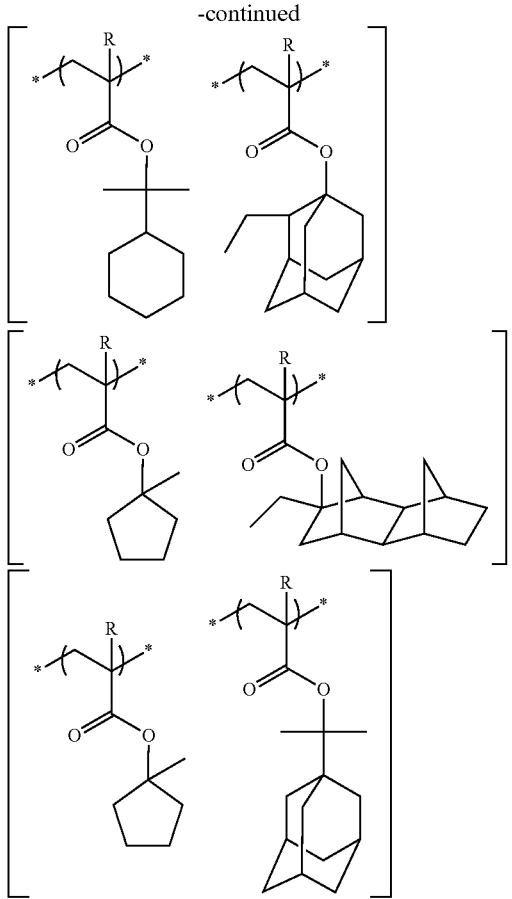

(Repeating Unit Having Lactone Structure)

The resin (B) may include a repeating unit having a lactone structure.

As the repeating unit having a lactone structure, any of repeating units which have a lactone structure can be used. The repeating unit is preferably a group having a 5- to 7-membered ring lactone structure, and more preferably a 5- to 7-membered ring lactone structure to which another ring structure is fused so as to form a bicyclo structure or spiro structure. Among those, the resin (B) still more preferably has a repeating unit having a lactone structure represented by any one of General Formulae (LC1-1) to (LC1-17). Further, the group having a lactone structure may be directly bonded to a main chain of the resin (B). A preferred lactone structure is a group represented by General Formula (LC1-1), General Formula (LC1-4), General Formula (LC1-5), General Formula (LC1-6), General Formula (LC1-13), General Formula (LC1-14), or General Formula (LC1-17), and by using a specific lactone structure, LWR and/or development defects are improved.

As the repeating unit having a lactone structure, a repeating unit represented by General Formula (AII') is preferable.

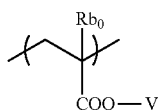

(AII')

In General Formula (AII'), $Rb_0$ represents a hydrogen atom, a halogen atom, or an alkyl group having 1 to 4 carbon atoms. Preferred examples of the substituent which may be contained in the alkyl group of $Rb_0$ include a hydroxyl group and a halogen atom. Examples of the halogen atom of $Rb_0$ include a fluorine atom, a chlorine atom, a bromine atom, and an iodine atom. As $Rb_0$, a hydrogen atom, a methyl group, a hydroxymethyl group, or a trifluoromethyl group is preferable, and the hydrogen atom or the methyl group is more preferable.

V represents a group having a structure represented by any one of General Formulae (LC1-1) to (LC1-17).

Specific examples of the repeating unit having a lactone structure are set for the below, but the present invention is not limited thereto.

(in the formulae Rx is H, $CH_3$, $CH_2OH$ or $CF_3$)

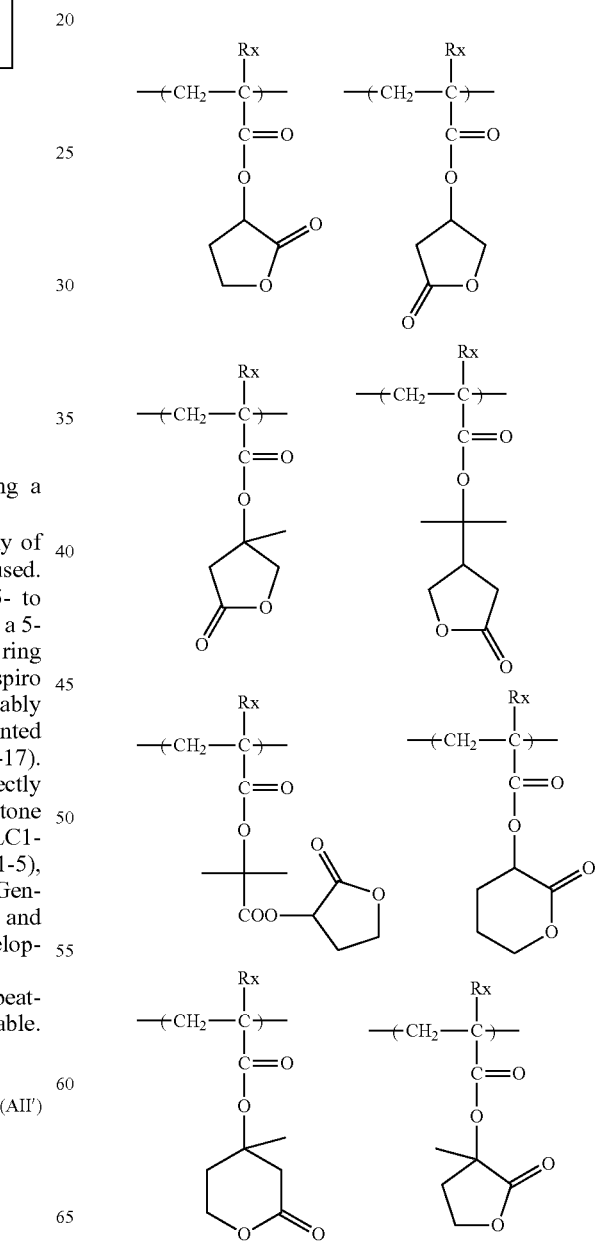

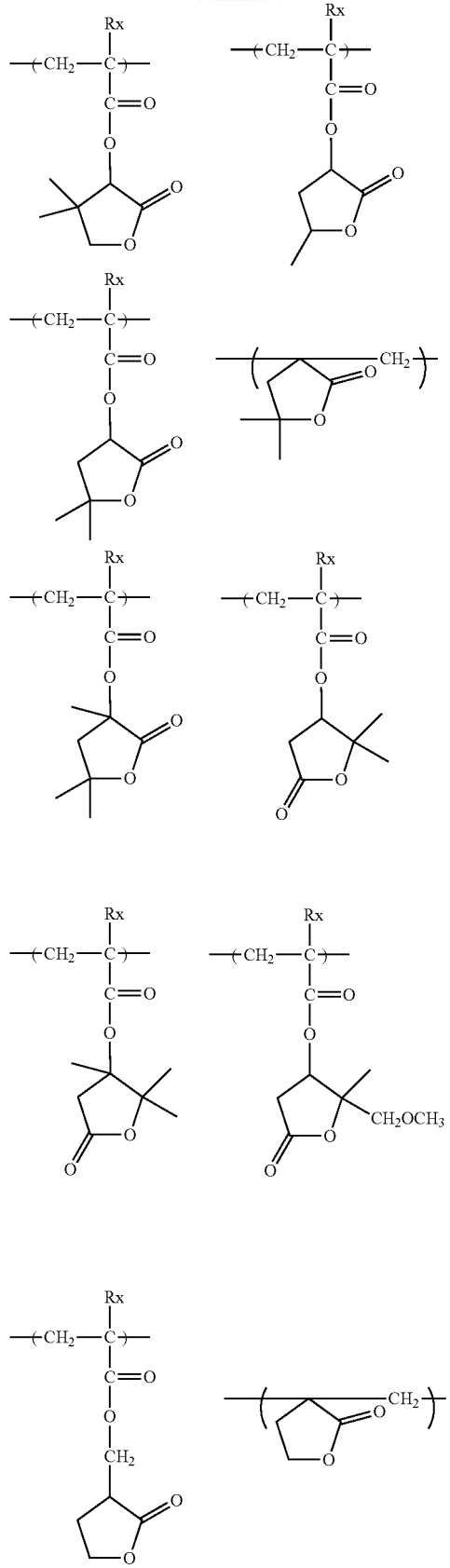
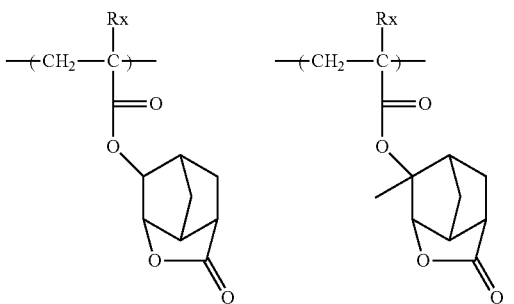
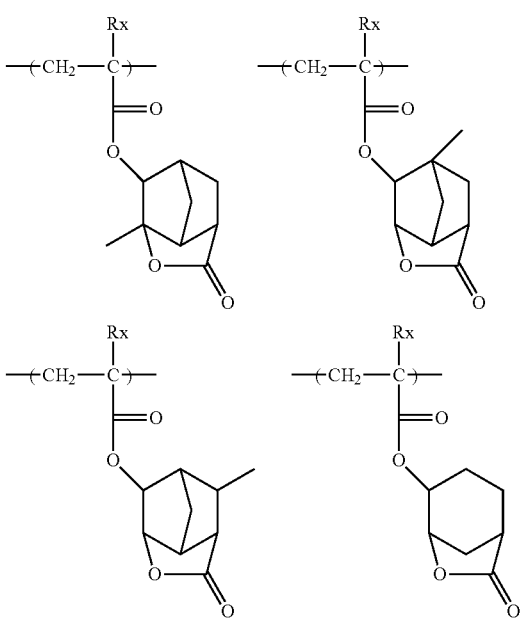
(in the formulae, Rx is H, CH$_3$, CH$_2$OH, or CF$_3$)

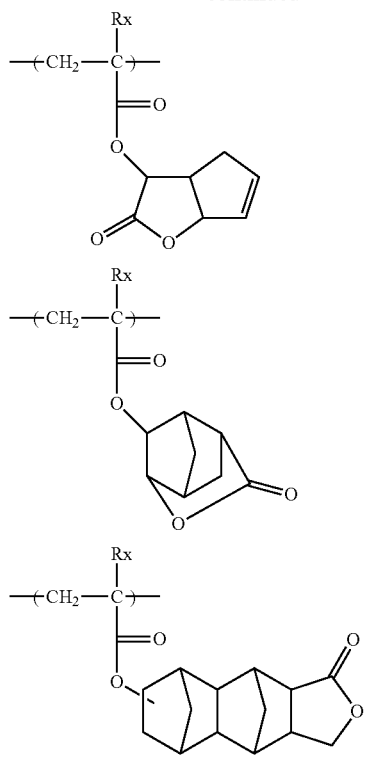
(in the formulae, Rx is H, CH₃, CH₂OH, or CF₃)
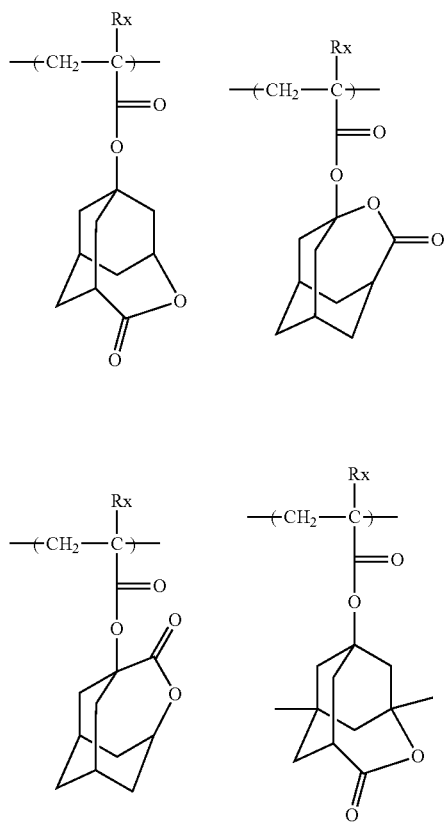
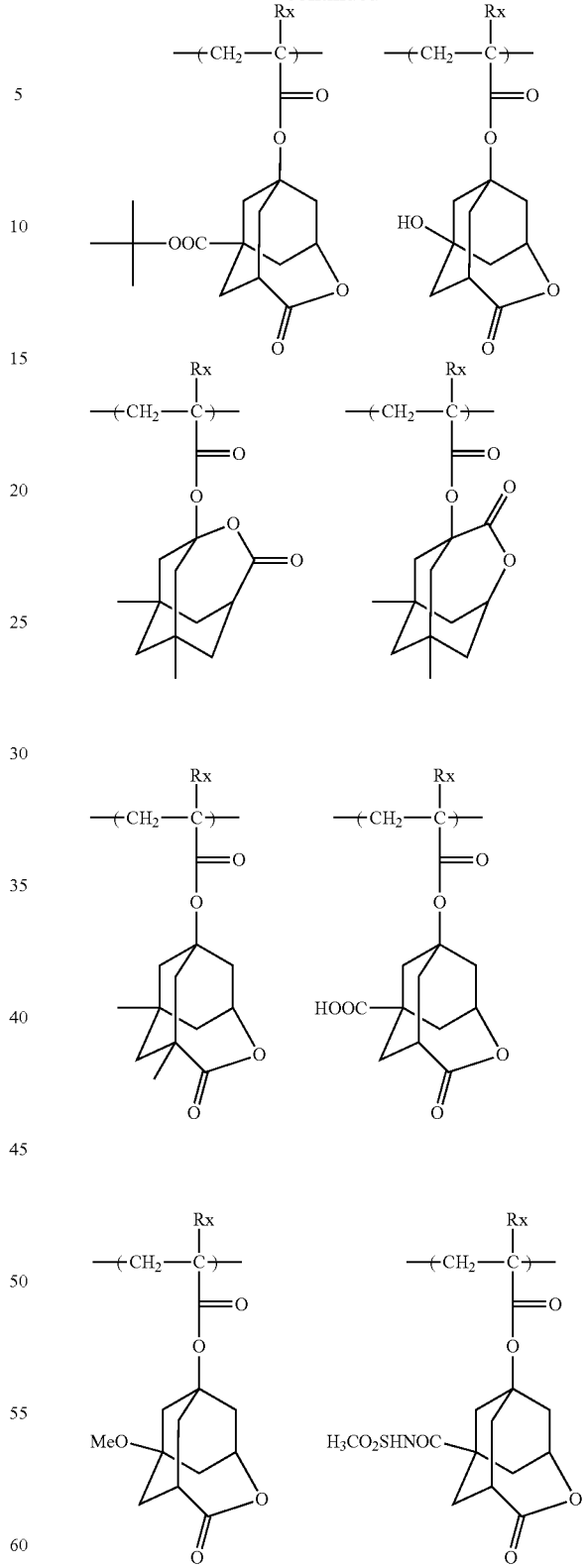
Preferred examples of the repeating unit having a lactone structure include the following repeating units. By selecting an optimal lactone structure, the pattern profile and the density dependency are improved.
(in the formulae, Rx is H, CHI, CH₂OH, or CF₃)

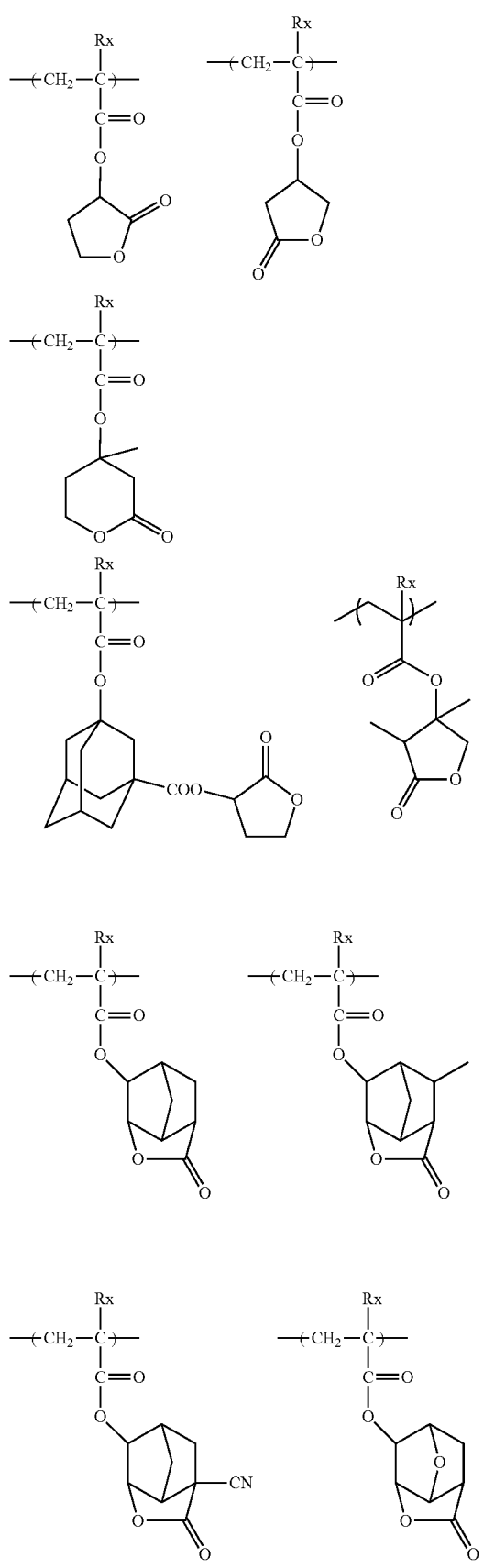
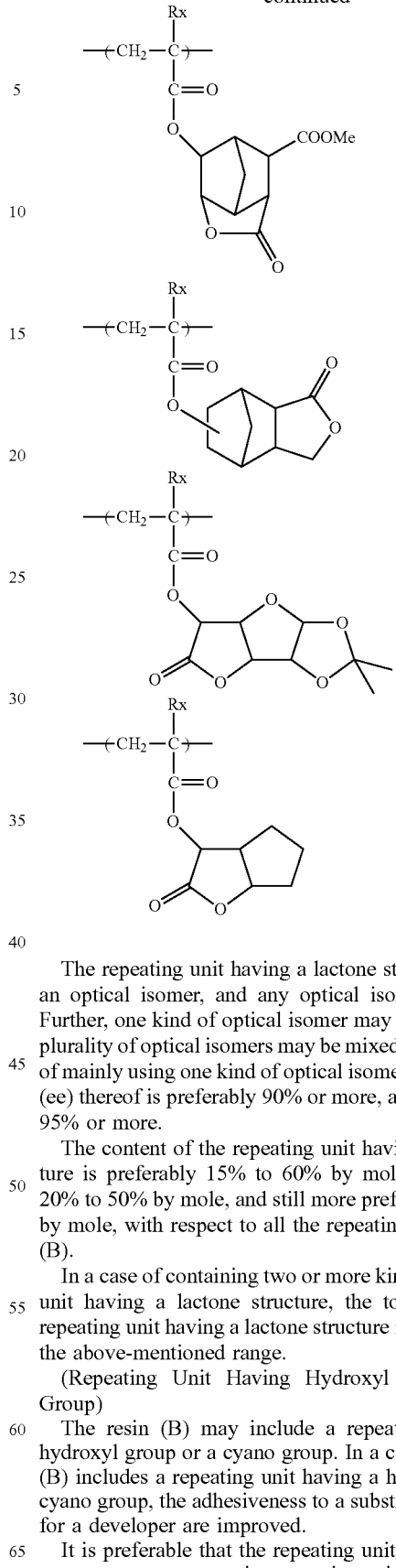

The repeating unit having a lactone structure usually has an optical isomer, and any optical isomer may be used. Further, one kind of optical isomer may be used singly or a plurality of optical isomers may be mixed and used. In a case of mainly using one kind of optical isomer, the optical purity (ee) thereof is preferably 90% or more, and more preferably 95% or more.

The content of the repeating unit having a lactone structure is preferably 15% to 60% by mole, more preferably 20% to 50% by mole, and still more preferably 30% to 50% by mole, with respect to all the repeating units in the resin (B).

In a case of containing two or more kinds of the repeating unit having a lactone structure, the total content of the repeating unit having a lactone structure is preferably within the above-mentioned range.

(Repeating Unit Having Hydroxyl Group or Cyano Group)

The resin (B) may include a repeating unit having a hydroxyl group or a cyano group. In a case where the resin (B) includes a repeating unit having a hydroxyl group or a cyano group, the adhesiveness to a substrate and the affinity for a developer are improved.

It is preferable that the repeating unit having a hydroxyl group or a cyano group is a repeating unit having an alicyclic hydrocarbon structure substituted with a hydroxyl group or a cyano group, and it is more preferable that the repeating unit does not have an acid-decomposable group. As the alicyclic hydrocarbon structure in the alicyclic hydrocarbon structure substituted with a hydroxyl group or a cyano group, an adamantyl group, a diadamantyl group, or a norbornane group is preferable. Preferred examples of the repeating unit having a hydroxyl group or a cyano group include repeating units represented by General Formulae.

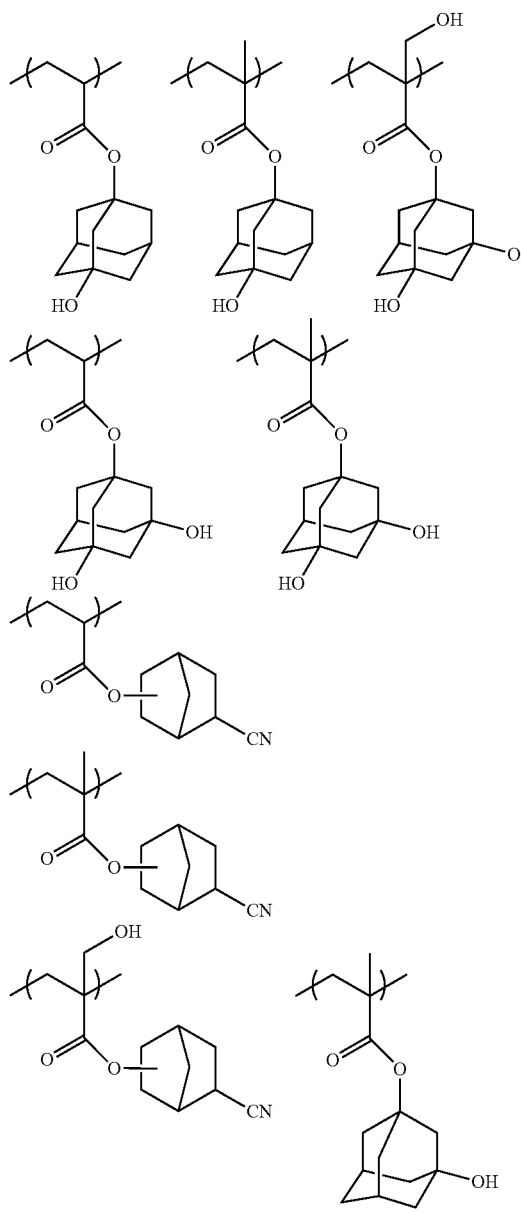

The content of the repeating unit having a hydroxyl group or a cyano group is preferably 5% to 40% by mole, more preferably 5% to 30% by mole, and still more preferably 10% to 25% by mole, with respect to all the repeating units of the resin (B).

Specific examples of the repeating unit having a hydroxyl group or a cyano group include the repeating units disclosed in paragraph 0340 of US2012/0135348A, but the present invention is not limited thereto.

(Repeating Unit Having Alkali-Soluble Group)

The resin (B) may include a repeating unit having an alkali-soluble group.

Examples of the alkali-soluble group include a carboxyl group, a sulfonamido group, a sulfonylimido group, a bis-sulfonylimido group, and an aliphatic alcohol (for example, a hexafluoroisopropanol group) which is substituted by an electron withdrawing group at the α-position, and more preferably having a repeating unit with a carboxyl group. Due to incorporation of a repeating unit having an alkali-soluble group into the resin (B), resolution during formation of contact holes is enhanced.

Examples of the repeating unit having an alkali-soluble group include a repeating unit in which an alkali-soluble group is bonded directly to the main chain of the resin such as a repeating unit derived from an acrylic acid or a methacrylic acid, a repeating unit in which an alkali-soluble group is bonded to the main chain of the resin via a linking group. Further, using a polymerization initiator or a chain transfer agent during polymerization, an alkali-soluble group may be introduced to a terminal of the resin. In addition, the linking group may have a monocyclic or polycyclic hydrocarbon structure.

The repeating unit derived from an acrylic acid or a methacrylic acid is particularly preferable.

The content of the repeating unit having an alkali-soluble group is preferably 0% to 20% by mole, more preferably 3% to 15% by mole, and still more preferably 5% to 10% by mole, with respect to all the repeating units in the resin (B).

Specific examples of the repeating unit having an alkali-soluble group include the repeating units disclosed in paragraph 0344 of US2012/0135348A, but the present invention is not limited thereto.

(Repeating Unit Having Alicyclic Hydrocarbon Structure Having No Polar Group and not Exhibiting Acid Decomposability)

The resin (B) may include a repeating unit having an alicyclic hydrocarbon structure not further having a polar group (for example, an alkali-soluble group, a hydroxyl group, and a cyano group) and not exhibiting acid decomposability. Examples of such a repeating unit include a repeating unit represented by General Formula (IV).

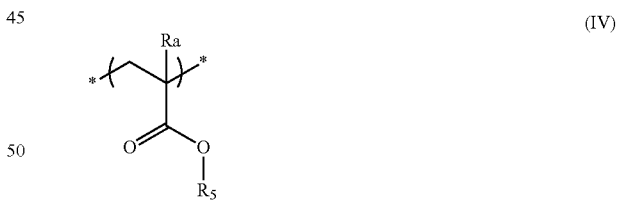

In General Formula (IV), $R_5$ represents a hydrocarbon group which has at least one cyclic structure and does not have a polar group.

Ra represents a hydrogen atom, an alkyl group, or a —$CH_2$—O—$Ra_2$ group. In the formula, $Ra_2$ represents a hydrogen atom, an alkyl group, or an acyl group. Ra is preferably a hydrogen atom, a methyl group, a hydroxymethyl group, or a trifluoromethyl group, and more preferably a hydrogen atom or a methyl group.

The cyclic structure contained in $R_5$ includes a monocyclic hydrocarbon group and a polycyclic hydrocarbon group. Examples of the monocyclic hydrocarbon group include cycloalkyl groups having 3 to 12 carbon atoms, such as a cyclopentyl group, a cyclohexyl group, a cycloheptyl group, and a cyclooctyl group, a cycloalkenyl groups having 3 to 12 carbon atoms, such as a cyclohexenyl group, and a phenyl group. As the monocyclic hydrocarbon group, a monocyclic hydrocarbon group having 3 to 7 carbon atoms is preferable, and a cyclopentyl group or a cyclohexyl group is more preferable.

Examples of the polycyclic hydrocarbon group include a ring-aggregated hydrocarbon group and a crosslinked cyclic hydrocarbon group, and examples of the ring-aggregated hydrocarbon group include a bicyclohexyl group, and a perhydronaphthalenyl group.

Examples of the crosslinked cyclic hydrocarbon ring include bicyclic hydrocarbon rings such as a pinane ring, a bornane ring, a norpinane ring, a norbornane ring, and a bicyclooctane ring (a bicyclo[2.2.2]octane ring, a bicyclo[3.2.1]octane ring, and the like), tricyclic hydrocarbon rings such as a homobrendane ring, an adamantane ring, a tricyclo[5.2.1.0$^{2,6}$]decane ring, and a tricyclo[4.3.1.1$^{2,5}$]undecane ring, and tetracyclic hydrocarbon rings such as a tetracyclo[4.4.0.1$^{2,5}$.1$^{7,10}$]dodecane ring and a perhydro-1,4-methano-5,8-methanonaphthalene ring. Other examples of the crosslinked cyclic hydrocarbon ring include a fused ring type hydrocarbon ring, for example, a fused ring in which a plurality of 5- to 8-membered cycloalkane rings such as a perhydronaphthalene ring (decalin), a perhydroanthracene ring, a perhydrophenanthrene ring, a perhydroacenaphthene ring, a perhydrofluorene ring, a perhydroindene ring, and a perhydrophenalene ring are fused.

Preferred examples of the crosslinked cyclic hydrocarbon ring include a norbornyl group, an adamantyl group, a bicyclooctanyl group, and a tricyclo[5.2.1.0$^{2,6}$]decanyl group. As the crosslinked cyclic hydrocarbon ring, a norbornyl group or an adamantyl group is preferable.

These alicyclic hydrocarbon groups may have a substituent. Preferred examples of the substituent include a halogen atom, an alkyl group, a hydroxyl group substituted with a hydrogen atom, an amino group substituted with a hydrogen atom, and the like. Preferred examples of the halogen atom include a bromine atom, a chlorine atom, and a fluorine atom, and preferred examples of the alkyl group include a methyl group, an ethyl group, a butyl group, and a t-butyl group. The alkyl group may further have a substituent, and examples of this substituent that may be further contained include a halogen atom, an alkyl group, a hydroxyl group substituted with a hydrogen atom, and an amino group substituted with a hydrogen atom.

Examples of the group to be substituted (substituent) for a hydrogen atom include an alkyl group, a cycloalkyl group, an aralkyl group, a substituted methyl group, a substituted ethyl group, an acyl group, an alkoxycarbonyl group, and an aralkyloxycarbonyl group. Preferred examples of the alkyl group include an alkyl group having 1 to 4 carbon atoms, preferred examples of the substituted methyl group include a methoxymethyl group, a methoxythiomethyl group, a benzyloxymethyl group, a t-butoxymethyl group, and a 2-methoxyethoxymethyl group, preferred examples of the substituted ethyl group include 1-ethoxyethyl group and 1-methyl-1-methoxyethyl group, preferred examples of the acyl group include an aliphatic acyl group having 1 to 6 carbon atoms, such as a formyl group, an acetyl group, a propionyl group, a butyryl group, an isobutyryl group, a valeryl group, and a pivaloyl group, and examples of the alkoxycarbonyl group include an alkoxycarbonyl group having 1 to 4 carbon atoms.

The resin (B) may or may not contain a repeating unit having an alicyclic hydrocarbon structure not having a polar group and not exhibiting acid decomposability, but in a case where the resin (B) contains the repeating unit, the content of the repeating unit is preferably 1% to 40% by mole, and more preferably 2% to 20% by mole, with respect to all the repeating units in the resin (B).

Specific examples of the repeating unit having an alicyclic hydrocarbon structure which does not have a polar group and does not exhibit acid decomposability include the repeating units disclosed in paragraph 0354 of US2012/0135348A, but the present invention is not limited thereto.

(Other Repeating Units)

The resin (B) may include a variety of repeating structural units, in addition to the repeating units, for the purpose of adjusting dry etching resistance, suitability for a standard developer, adhesiveness to a substrate, and a resist profile, resolving power, heat resistance, sensitivity, and the like.

Examples of such a repeating unit include, but are not limited to, repeating units corresponding to the monomers which will be described later.

Thus, it becomes possible to perform fine adjustments to performance required for the resin (B), in particular, (1) solubility with respect to a coating solvent, (2) film forming properties (glass transition point), (3) alkali developability, (4) film (selection of hydrophilic, hydrophobic, or alkali-soluble groups), (5) adhesiveness of an unexposed area to a substrate, (6) dry etching resistance, and the like.

Examples of such a monomer include a compound having one addition-polymerizable unsaturated bond, which is selected from acrylic acid esters, methacrylic acid esters, acrylamides, methacrylamides, allyl compounds, vinyl ethers, vinyl esters, and the like.

In a case for uses for ArF exposure, it is preferable that the resin (B) does not substantially have an aromatic group in terms of transparency to ArF light, and it is preferable that the resin (B) has a monocyclic or polycyclic alicyclic hydrocarbon structure.

Incidentally, it is preferable that the resin (B) contains neither a fluorine atom nor a silicon atom from the viewpoint of compatibility with the hydrophobic resin (D) which will be described later.

The resin (B) is preferably a resin in which all the repeating units are constituted with (meth)acrylate-based repeating units. In this case, any of a resin in which all of the repeating units are methacrylate-based repeating units, a resin in which all of the repeating units are acrylate-based repeating units, a resin in which all of the repeating units are methacrylate-based repeating units and acrylate-based repeating units can be used. Above all, it is preferable that the acrylate-based repeating units account for 50% by mole or less of all of the repeating units.

In addition, a copolymer which includes 20% to 50% by mole of a (meth)acrylate-based repeating unit having an acid-decomposable group, 20% to 50% by mole of a (meth)acrylate-based repeating unit having a lactone group, and 5% to 30% by mole of a (meth)acrylate-based repeating unit having an alicyclic hydrocarbon structure which is substituted with a hydroxyl group or a cyano group, and further includes 0% to 20% by mole of other (meth)acrylate-based repeating units is also preferable.

In a case of irradiating a resist film with KrF excimer laser light, electron beams, X-rays, or high energy rays at a wavelength of 50 nm or less (EUV and the like), it is preferable that the resin (B) further has a repeating unit having a phenolic hydroxyl group. As the repeating unit having a phenolic hydroxyl group, repeating units shown below are preferable.

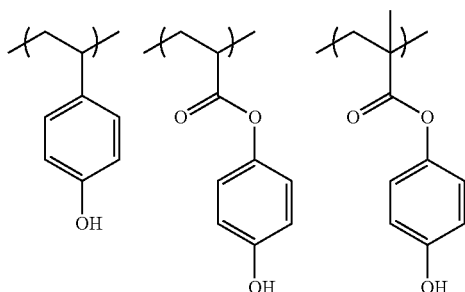

(Method for Synthesizing Resin (B))

The resin (B) can be synthesized in accordance with an ordinary method (for example, radical polymerization). Examples of the general synthesis method include a bulk polymerization method in which polymerization is carried out by dissolving monomer species and an initiator in a solvent and heating the solution, a dropwise addition polymerization method in which a solution of monomer species and an initiator is added dropwise to a heating solvent for 1 to 10 hours, with the dropwise addition polymerization method being preferable.

The weight-average molecular weight of the resin (B) is preferably 1,000 to 200,000, more preferably 2,000 to 20,000, still more preferably 3,000 to 15,000, and particularly preferably 3,000 to 10,000 as a value in terms of polystyrene by a gel permeation chromatography (GPC) method. By setting the weight-average molecular weight to 1,000 to 200,000, it is possible to further improve heat resistance and dry etching resistance, to improve developability, or to suppress deterioration in the film forming properties due to an increase in viscosity.

In the measurement by a GPC method, for example, HLC-8120 (manufactured by Tosoh Corporation) can be used, in which a TSK gel Multipore HXL-M (manufactured by Tosoh corporation, 7.8 mmID×30.0 cm) is used as a column and tetrahydrofuran (THF) is used as an eluent.

The dispersity (molecular weight distribution) of the resin (B) is usually 1 to 3, preferably 1 to 2.6, more preferably 1 to 2, and still more preferably 1.4 to 2.0. As the molecular weight distribution of the resin is smaller, the resolution and the resist profile are more excellent, the side wall of the pattern is smoother, and the roughness is excellent.

The resin (B) may be used singly or in combination of two or more kinds thereof.

The content of the resin (B) is preferably 30% to 99% by mass, and more preferably 60% to 95% by mass, with respect to the total solid content of the composition.

Specific examples of the resin (B) are set forth below, but the present invention is not limited thereto.

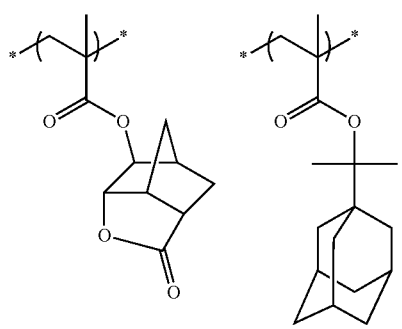

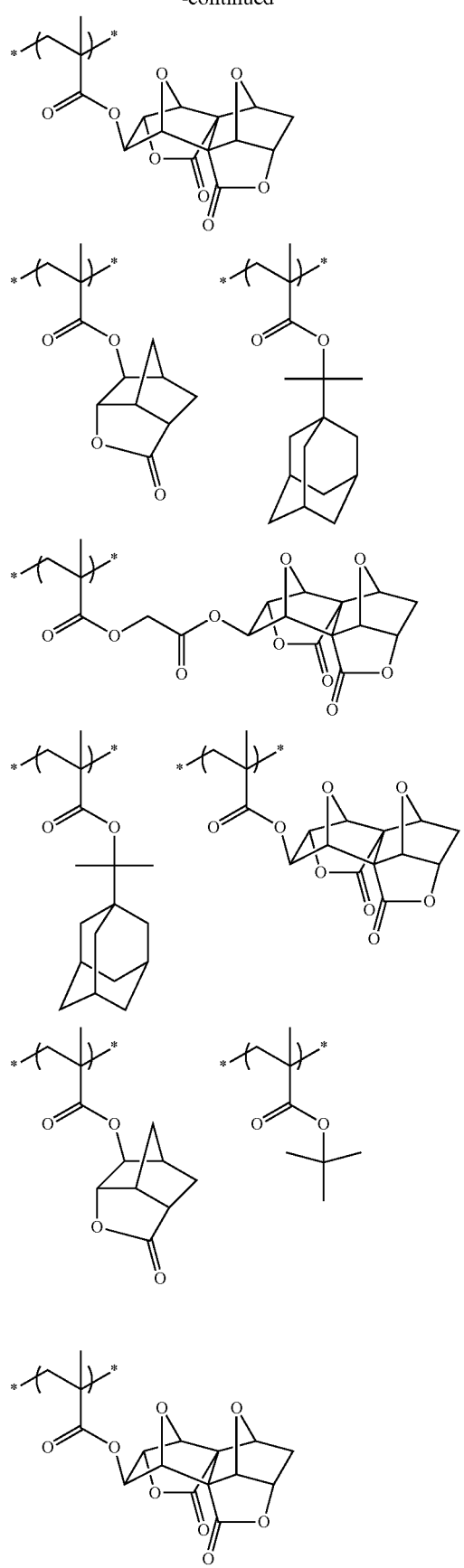

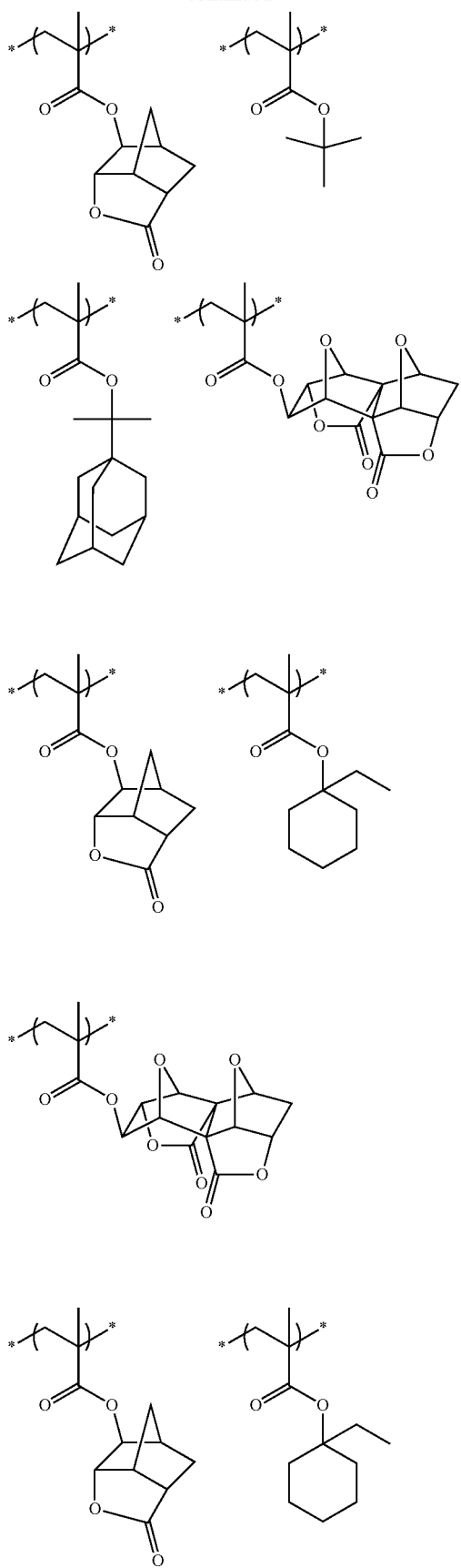
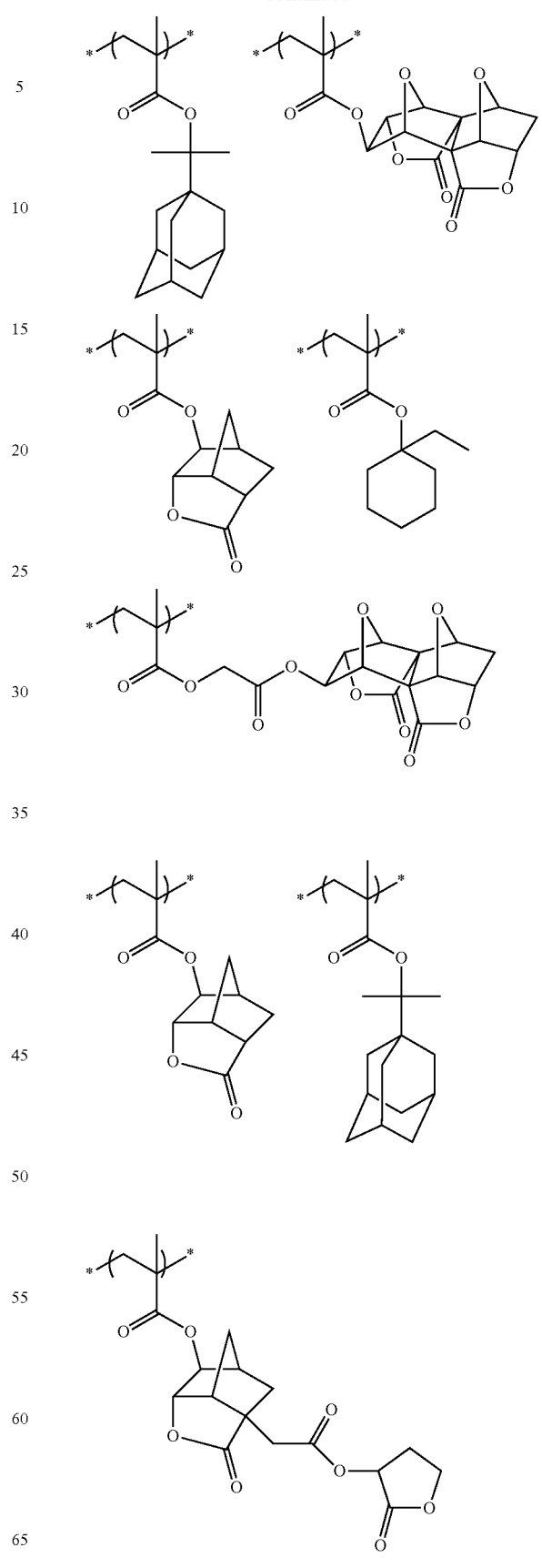

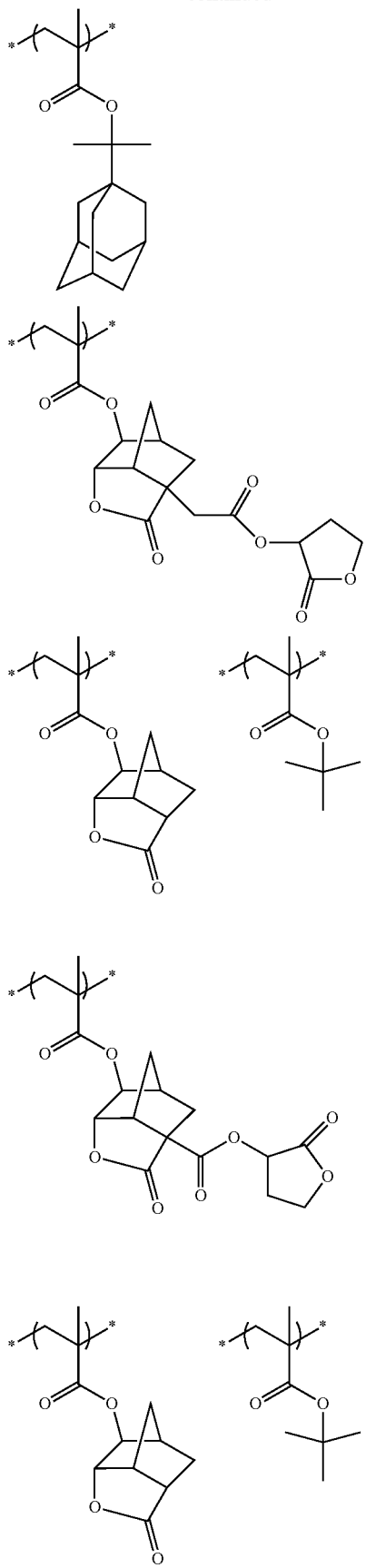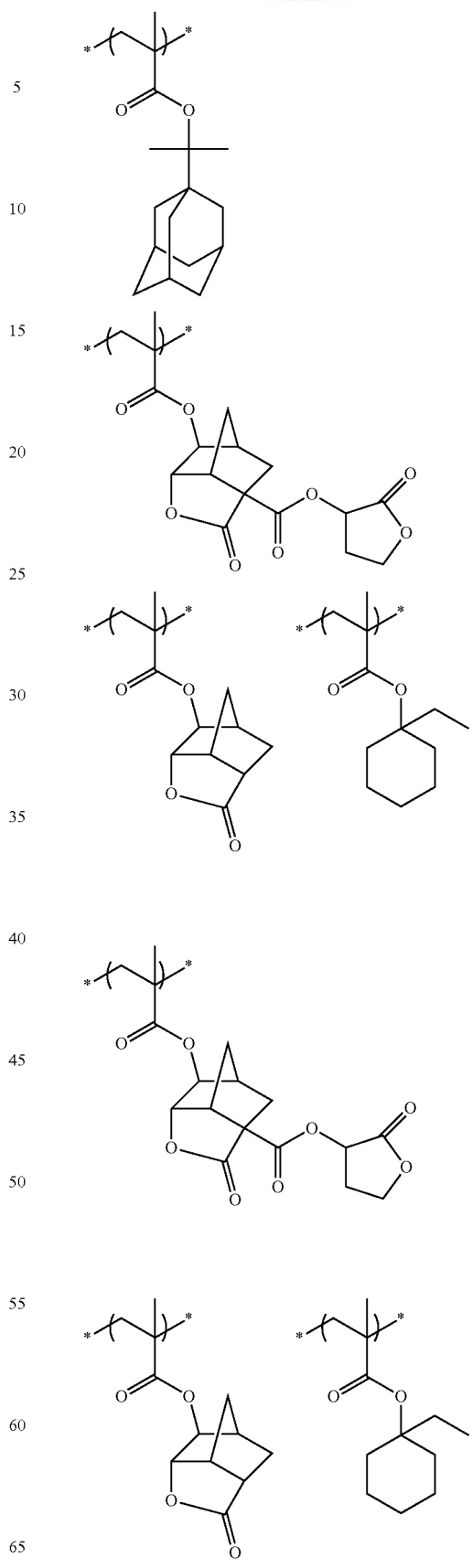

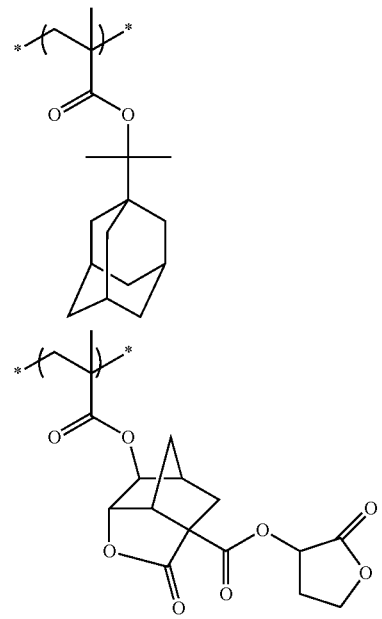
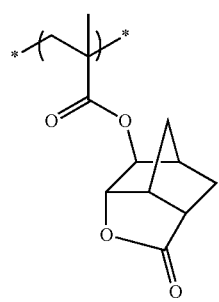
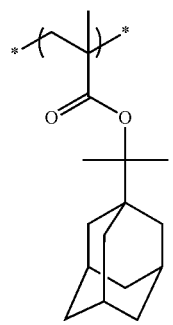
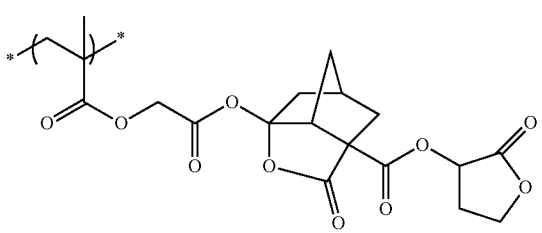

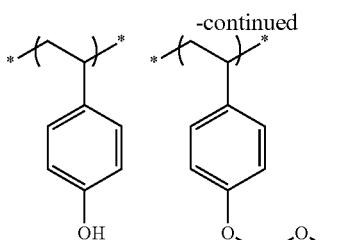
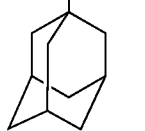
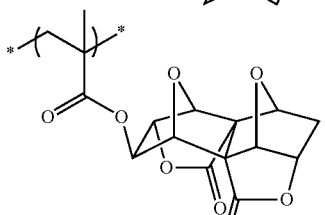
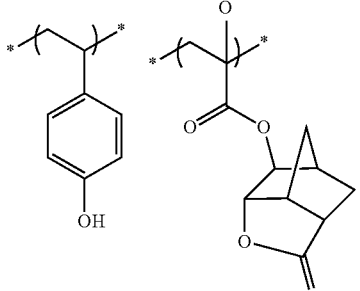
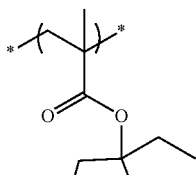
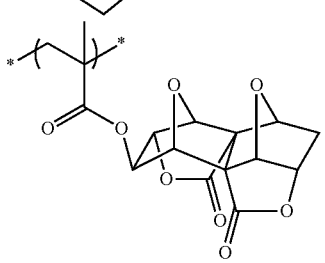
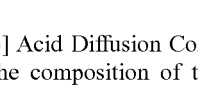

[3] Acid Diffusion Control Agent (C)

The composition of the present invention may further include an acid diffusion control agent (C). The acid diffusion control agent (C) acts as a quencher that traps an acid generated from a photoacid generator upon exposure, and functions to control diffusion development of the acid in the resist film.

The acid diffusion control agent (C) may be, for example, a basic compound. The basic compound is preferably a compound having stronger basicity than a phenol. Further, this basic compound is preferably an organic basic compound, and more preferably a nitrogen-containing basic compound. The type of the nitrogen-containing basic compound which can be used is not particularly limited, but for example, compounds classified into (1) to (5) below can be used.

Furthermore, in another embodiment, the composition of the present invention may include, for example, an ionic compound classified into (6) below as the acid diffusion control agent.

(1) Basic Compound (C1) Having Hydrophilic Functional Group

The basic compound (C1) having a hydrophilic functional group is preferably a compound represented by General Formula (BS-1).

(BS-1)

In General Formula (BS-1),

R's each independently represent a hydrogen atom or an organic group, provided that at least one of three R's is an organic group. This organic group is a linear or branched alkyl group, a monocyclic or polycyclic cycloalkyl group, an aryl group, or an aralkyl group.

A hydrogen atom in the alkyl group, the cycloalkyl group, the aryl group, or the aralkyl group as R may be substituted with a substituent. Examples of the substituent include an alkyl group, a cycloalkyl group, an aryl group, an aralkyl group, a hydroxyl group, a carboxyl group, an alkoxy group, an aryloxy group, an alkylcarbonyloxy group, and an alkyloxycarbonyl group. Further, an oxygen atom, a sulfur atom, a carbonyl group, and a combination thereof may be included in the alkyl group.

In addition, it is preferable that at least two of R's are organic groups in the compound represented by General Formula (BS-1).

Furthermore, two of R's may be bonded to each other to form a ring. The formed ring may be substituted with a substituent (for example, a hydroxyl group).

Specific examples of the compound represented by General Formula (BS-1) include tri-n-butylamine, tri-n-pentylamine, tri-n-octylamine, tri-n-decylamine, triisodecylamine, dicyclohexylmethylamine, tetradecylamine, pentadecylamine, hexadecylamine, octadecylamine, didecylamine, methyl octadecylamine, dimethylundecylamine, N,N-dimethyldodecylamine, methyl dioctadecylamine, N,N-dibutyl aniline, N,N-dihexyl aniline, 2,6-diisopropyl aniline, N-phenyldiethanolamine, and 2,4,6-tri(t-butyl)aniline.

Furthermore, the basic compound represented by General Formula (BS-1) is preferably an alkyl group in which at least one of three R's has a hydrophilic group. By using this basic compound, the resolution of the pattern is improved and a good pattern shape is obtained.

The number of carbon atoms of an alkyl group having a hydrophilic group is preferably 1 to 8, and more preferably 1 to 6.

Examples of the alkyl group having a hydrophilic group include an alkyl group having a hydroxyl group or a mercapto group. Specific examples of such the basic compound having an alkyl group include triethanolamine and N,N-dihydroxyethylaniline.

Moreover, examples of the alkyl group having a hydrophilic group also include an alkyl group having an oxygen atom, a sulfur atom, or a carbonyl group. Specific examples of the compound such a group include tris(methoxyethoxyethyl)amine and the compounds exemplified after line 60 of column 3 in the specification of U.S. Pat. No. 6,040,112A.

The alkyl group having a hydrophilic group may be an alkyl group having a hydroxyl group or a mercapto group as the substituent and also having an oxygen atom, a sulfur atom, or a carbonyl group.

The alkyl group having a hydrophilic group may further have a substituent. Examples of such the additional substituent include a substituted or unsubstituted aryl group. In a case where the aryl group is a substituted aryl group, examples of the substituent in the substituted aryl group include an alkyl group, an alkoxy group, and an aryl group.

(2) Compound Having Nitrogen-Containing Heterocyclic Structure

The nitrogen-containing heterocycle in a compound having a nitrogen-containing heterocycle structure may or may not have aromatic properties. Further, the nitrogen-containing heterocycle may have a plurality of nitrogen atoms. Incidentally, the nitrogen-containing heterocycle may contain heteroatoms other than the nitrogen atom.

Examples of the nitrogen-containing heterocycle structure include a compound having an imidazole structure (2-phenylbenzimidazole, 2,4,5-triphenylimidazole, 2-phenylbenzimidazle, and the like), a compound having a piperidine structure [N-hydroxyethylpiperidine, bis(1,2,2,6,6-pentamethyl-4-piperidyl)sebacate, and the like], a compound having a pyridine structure (4-dimethylaminopyridine and the like), and a compound having an antipyrine structure (antipyrine, hydroxyantipyrine, and the like).

Moreover, a compound having two or more ring structures is also suitably used as the compound having a nitrogen-containing heterocycle structure. Specific examples thereof include 1,5-diazabicyclo[4.3.0]non-5-ene and 1,8-diazabicyclo[5.4.0]undeca-7-ene.

(3) Amine Compound Having Phenoxy Group

An amine compound having a phenoxy group is a compound having a phenoxy group at the terminal on the opposite side to the N atom of the alkyl group which is contained in an amine compound. The phenoxy group may have a substituent such as an alkyl group, an alkoxy group, a halogen atom, a cyano group, a nitro group, a carboxyl group, a carboxylic acid ester group, a sulfonic acid ester group, an aryl group, an aralkyl group, an acyloxy group, and an aryloxy group.

The amine compound having a phenoxy group preferably has at least one oxyalkylene chain between the phenoxy group and the nitrogen atom. The number of oxyalkylene chains per molecule is preferably 3 to 9, and more preferably 4 to 6. Among the oxyalkylene chains, —$CH_2CH_2O$— is preferable.

Specific examples of the amine compound having a phenoxy group include 2-[2-{2-(2,2-dimethoxyphenoxyethoxy)ethyl}-bis-(2-methoxyethyl)]amine, and the compounds (C1-1) to (C3-3) exemplified in paragraph [0066] in the specification of US2007/0224539A1.

(4) Ammonium Salt

An ammonium salt can also be appropriately used as a basic compound.

Examples of the anion of the ammonium salt include halide, sulfonate, borate, and phosphate. Among those, halide or sulfonate is preferable.

As the halide, chloride, bromide, or iodide is preferable.

As the sulfonate, an organic sulfonate having 1 to 20 carbon atoms is preferable. Examples of the organic sulfonate include alkyl sulfonate and aryl sulfonate, each having 1 to 20 carbon atoms.

The alkyl group included in the alkyl sulfonate may have a substituent. Examples of the substituent include a fluorine atom, a chlorine atom, a bromine atom, an alkoxy group, an acyl group, and an aryl group. Specific examples of the alkyl sulfonate include methanesulfonate, ethanesulfonate, butanesulfonate, hexanesulfonate, octanesulfonate, benzylsulfonate, trifluoromethanesulfonate, pentafluoroethanesulfonate, and nonafluorobutanesulfonate.

Examples of the aryl group included in the aryl sulfonate include a phenyl group, a naphthyl group, and an anthryl group. These aryl groups may have a substituent.

The ammonium salt may be hydroxide or carboxylate. In this case, this ammonium salt is preferably tetraalkylammonium hydroxide having 1 to 8 carbon atoms, such as tetramethylammonium hydroxide, tetraethylammonium hydroxide, and tetra-(n-butyl)ammonium hydroxide.

Preferred examples of the basic compound include guanidine, aminopyridine, aminoalkylpyridine, aminopyrrolidine, indazole, imidazole, pyrazole, pyrazine, pyrimidine, purin, imidazoline, pyrazoline, piperazine, aminomorpholine, and aminoalkylmorpholine. These may further have a substituent.

(5) Compound (PA) that has Proton-Accepting Functional Group and Decomposes Upon Irradiation with Actinic Rays or Radiation to Generate Compound Exhibiting Deterioration in Proton-Accepting Properties, No Proton-Accepting Properties, or Change from Proton-Accepting Properties to Acidic Properties The composition according to the present invention may further include, as a basic compound, a compound (hereinafter also referred to as a compound (PA)) that has a proton-accepting functional group and decomposes upon irradiation with actinic rays or radiation to generate a compound exhibiting deterioration in proton-accepting properties, no proton-accepting properties, or a change from the proton-accepting properties to acidic properties.

The proton-accepting functional group refers to a functional group having a group or electron which is capable of electrostatically interacting with a proton, and for example, means a functional group with a macrocyclic structure, such as a cyclic polyether, or a functional group containing a nitrogen atom having an unshared electron pair not contributing to π-conjugation. The nitrogen atom having an unshared electron pair not contributing to π-conjugation is, for example, a nitrogen atom having a partial structure represented by the following general formula.

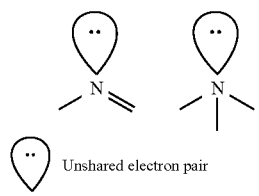

Preferred examples of the partial structure of the proton-accepting functional group include crown ether, azacrown ether, primary to tertiary amines, pyridine, imidazole, and pyrazine structures.

The compound (PA) decomposes upon irradiation with actinic rays or radiation to generate a compound exhibiting deterioration in proton-accepting properties, no proton-accepting properties, or a change from the proton-accepting properties to acidic properties. Here, exhibiting deterioration in proton-accepting properties, no proton-accepting properties, or a change from the proton-accepting properties to acidic properties means a change of proton-accepting properties due to the proton being added to the proton-accepting functional group, and specifically a decrease in the equilibrium constant at chemical equilibrium in a case where a proton adduct is generated from the compound (PA) having the proton-accepting functional group and the proton.

The proton-accepting properties can be confirmed by carrying out pH measurement.

The compound (PA) generates a compound represented by General Formula (PA-1), for example, as the proton adduct generated by decomposition upon irradiation with actinic rays or radiation. The compound represented by General Formula (PA-1) is a compound exhibiting deterioration in proton-accepting properties, no proton-accepting properties, or a change from the proton-accepting properties to acidic properties since the compound has a proton-accepting functional group as well as an acidic group, as compared with the compound (PA).

In General Formula (PA-1),

Q represents —$SO_3H$, —$CO_2H$, or —$X_1NHX_2R_f$, in which $R_f$ represents an alkyl group, a cycloalkyl group, or an aryl group, and $X_1$ and $X_2$ each independently represent —$SO_2$— or —CO—.

A represents a single bond or a divalent linking group.

X represents —$SO_2$— or —CO—.

n is 0 or 1.

B represents a single bond, an oxygen atom, or —N(Rx)Ry-.

Rx represents a hydrogen atom or a monovalent organic group, and Ry represents a single bond or a divalent organic group. Rx may be bonded to Ry to form a ring or may be bonded to R to form a ring.

R represents a monovalent organic group having a proton-accepting functional group.

Furthermore, compounds (PA) other than the compound that generates the compound represented by General Formula (PA-1) can also be appropriately selected. For example, a compound having a proton-accepting moiety at its cationic moiety may be used as an ionic compound. More specific examples thereof include a compound represented by General Formula (7).

In General Formula (7), A represents a sulfur atom or an iodine atom.

m represents 1 or 2 and n represents 1 or 2, provided that m+n=3 in a case where A is a sulfur atom and that m+n=2 in a case where A is an iodine atom.

R represents an aryl group.

$R_N$ represents an aryl group substituted with the proton-accepting functional group.

$X^-$ represents an anion.

Specific examples of $X^-$ include the same anions as those for $Y^-$ in General Formula (1) as described above.

As the aryl group of each of R and $R_N$, a phenyl group is preferable.

Specific examples of the proton-accepting functional group contained in $R_N$ are the same as the proton-accepting functional group in General Formula (PA-1) as described above.

In a case where the composition contains the compound (PA), the content of the compound (PA) is preferably 0.1% to 10% by mass, and more preferably 1% to 8% by mass, with respect to the total solid content of the composition.

(6) Ionic Compound

The composition of the present invention may contain an ionic compound which becomes a relatively weak acid with respect to an acid generator. As the ionic compound, an onium salt is preferable. In a case where the acid generated from the acid generator upon irradiation with actinic rays or radiation collides with an onium salt having an unreacted weak acid anion, a weak acid is discharged by salt exchange, thereby generating an onium salt having a strong acid anion. In this process, the strong acid is exchanged with a weak acid having a lower catalytic ability, and therefore, the acid is deactivated in appearance, and thus, it is possible to carry out the control of acid diffusion.

As the onium salt which becomes a relatively weak acid with respect to the acid generator, a compound represented by General Formula (4), (5), or (6) is preferable.

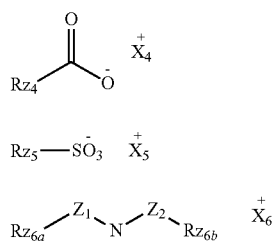

Hereinafter, General Formula (4) will be described.

$X_4^+$ represents a cation.

$Rz_4$ represents a cyclic group, an alkyl group, or an alkenyl group. The cyclic group, the alkyl group, and the alkenyl group of $Rz_4$ may each have a substituent (for example, a hydroxyl group).

Examples of the cation of $X_4^+$ include a sulfonium cation and an iodonium cation.

Examples of the cyclic group of $Rz_4$ include an aryl group and a cycloalkyl group. The cyclic group of $Rz_4$ may be monocyclic or polycyclic.

The alkyl group of $Rz_4$ preferably has, for example, 1 to 30 carbon atoms, and more preferably has 3 to 10 carbon atoms.

Examples of the alkenyl group of $Rz_4$ include an alkenyl group having 2 to 10 carbon atoms, and the alkenyl group may be linear or branched. The alkenyl group of $Rz_4$ is preferably a linear alkenyl group having 2 to 4 carbon atoms.

Preferred examples of the anionic moiety of the compound represented by General Formula (4) include the structures exemplified in paragraph [0198] of JP2012-242799A.

Hereinafter, General Formula (5) will be described.

$X_5^+$ represents a cation.

$Rz_5$ represents a cyclic group, an alkyl group, or an alkenyl group. The cyclic group, the alkyl group, and the alkenyl group of $Rz_5$ may each have a substituent, provided that the carbon atom adjacent to the S atom is not bonded to a fluorine atom.

Examples the cation of $X_5^+$ include a sulfonium cation and an iodonium cation.

Examples of the cyclic group of $Rz_5$ include an aryl group and a cycloalkyl group. The cyclic group of $Rz_5$ may be monocyclic or polycyclic.

The alkyl group of $Rz_5$ preferably has, for example, 1 to 30 carbon atoms, and more preferably has 3 to 10 carbon atoms.

Examples of the alkenyl group of $Rz_5$ include an alkenyl group having 2 to 10 carbon atoms, and the alkenyl group may be linear or branched. The alkenyl group of $Rz_5$ is preferably a linear alkenyl group having 2 to 4 carbon atoms.

Preferred examples of the anionic moiety of the compound represented by General Formula (5) include the structures exemplified in paragraph [0201] of JP2012-242799A.

Hereinafter, General Formula (6) will be described.

$X_6^+$ represents a cation.

$Rz_{6a}$ and $Rz_{6b}$ each independently represent a cyclic group, an alkyl group, or an alkenyl group. The cyclic group, the alkyl group, and the alkenyl group of each of $Rz_{6a}$ and $Rz_{6b}$ may each have a substituent (for example, a halogen atom).

$Z_1$ and $Z_2$ each independently represent a single bond or a divalent linking group, provided that a case where $Z_1$ and $Z_2$ are both —$SO_2$— is excluded.

Examples of the cation of $X_6^+$ include a sulfonium cation and an iodonium cation.

Examples of the cyclic group of each of $Rz_{6a}$ and $Rz_{6b}$ include an aryl group and a cycloalkyl group. The cyclic group of each of $Rz_{6a}$ and $Rz_{6b}$ may be monocyclic or polycyclic.

The alkyl group each of $Rz_{6a}$ and $Rz_{6b}$ preferably has, for example, 1 to 30 carbon atoms, and more preferably has 3 to 10 carbon atoms.

Examples of the alkenyl group each of $Rz_{6a}$ and $Rz_{6b}$ include an alkenyl group having 2 to 10 carbon atoms, and the alkenyl group may be linear or branched. The alkenyl group of each of $Rz_{6a}$ and $Rz_{6b}$ is preferably a linear alkenyl group having 2 to 4 carbon atoms.

Examples of the divalent linking group of each of $Z_1$ and $Z_2$ include a divalent linking group which may have a substituent divalent hydrocarbon group (an aliphatic hydrocarbon group or an aromatic hydrocarbon group), and includes a heteroatom. Further, the divalent linking group of each of $Z_1$ and $Z_2$ is preferably —$SO_2$—, a carbonyl group, an ester bond, an amide bond, an alkylene group, or a combination thereof. As the alkylene group, a linear or branched alkylene group is preferable, and a methylene group or an ethylene group is more preferable.

Preferred examples of the anionic moiety of the compound represented by General Formula (6) include the structures exemplified in paragraphs [0209] and [0210] of JP2012-242799A.

Specific examples of the compounds represented by General Formulae (4) to (6) are shown below, but are not limited thereto.

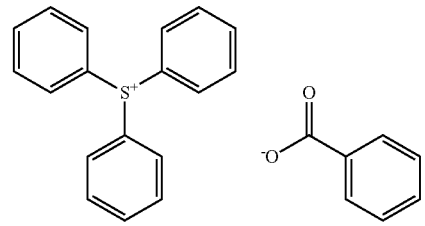

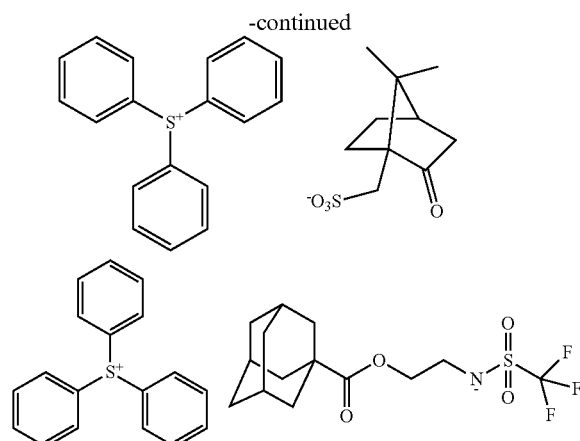

The onium salt which becomes a relatively weak acid with respect to the acid generator may be a compound (hereinafter also referred to as a "compound (CA)") having a cationic moiety (C) and an anionic moiety in the same molecule, in which the cationic moiety and the anionic moiety are linked to each other through a covalent bond.

The compound (CA) is preferably a compound represented by any one of General Formulae (C-1) to (C-3).

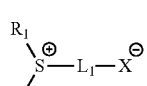

(C-1)

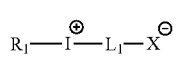

(C-2)

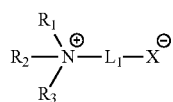

(C-3)

In General Formulae (C-1) to (C-3), $R_1$, $R_2$, and $R_3$ represent a substituent having 1 or more carbon atoms.

$L_1$ represents a divalent linking group that links a cationic moiety with an anionic moiety, or a single bond.

—$X^-$ represents an anionic moiety selected from —COO$^-$, —SO$_3^-$, —SO$_2^-$, and —N$^-$—R$_4$. $R_4$ represents a monovalent substituent having a carbonyl group: —C(=O)—, a sulfonyl group: —S(=O)$_2$—, or a sulfinyl group: —S(=O)— at a site for linking to an adjacent nitrogen atom.

$R_1$, $R_2$, $R_3$, $R_4$, and $L_1$ may be bonded to one another to form a ring structure. Further, in (C-3), two members out of $R_1$ to $R_3$ may be combined to form a double bond with a nitrogen atom.

Examples of the substituent having 1 or more carbon atoms in each of $R_1$ to $R_3$ include an alkyl group, a cycloalkyl group, an aryl group, an alkyloxycarbonyl group, a cycloalkyloxycarbonyl group, an aryloxycarbonyl group, an alkylaminocarbonyl group, a cycloalkylaminocarbonyl group, and an arylaminocarbonyl group, and preferably an alkyl group, a cycloalkyl group, and an aryl group.

Examples of $L_1$ as a divalent linking group include a linear or branched alkylene group, a cycloalkylene group, an arylene group, a carbonyl group, an ether bond, an ester bond, an amide bond, a urethane bond, a urea bond, and a group formed by a combination of two or more kinds of these groups. $L_1$ is more preferably an alkylene group, an arylene group, an ether bond, an ester bond, and a group formed by a combination of two or more kinds of these groups.

Preferred examples of the compound represented by General Formula (C-1) include the compounds exemplified in paragraphs [0037] to [0039] of JP2013-6827A and paragraphs [0027] of [0029] JP2013-8020A.

Preferred examples of the compound represented by General Formula (C-2) include the compounds exemplified in paragraphs [0012] and [0013] of JP2012-189977A.

Preferred examples of the compound represented by General Formula (C-3) include the compounds exemplified in paragraphs [0029] to [0031] of JP2012-252124A.

In addition to these, examples of the acid diffusion control agent (C) which can be used in the composition of the present invention include the compounds synthesized in Examples of JP2002-363146A and the compounds described in paragraph 0108 of JP2007-298569A.

As the acid diffusion control agent (C), a photosensitive basic compound may be used. As the photosensitive basic compound, for example, the compounds described in JP2003-524799A, J. Photopolym. Sci. & Tech. Vol. 8, P. 543-553 (1995), and the like can be used.

The molecular weight of the acid diffusion control agent (C) is usually 100 to 1,500, preferably 150 to 1,300, and more preferably 200 to 1,000.

These acid diffusion control agents (C) may be used singly or in combination of two or more kinds thereof.

In a case where the composition of the present invention includes the acid diffusion control agent (C), the content of the acid diffusion control agent (C) is preferably 0.01% to 8.0% by mass, more preferably 0.1% to 5.0% by mass, and still more preferably 0.2% to 4.0% by mass, with respect to the total solid content of the composition.

The molar ratio of the acid diffusion control agent (C) to the photoacid generator is preferably 0.01 to 10, more preferably to 0.05 to 5, and still more preferably 0.1 to 3. Within the range, the sensitivity and/or the resolution is/are good, it is difficult to make a pattern finer at a time between exposure and heating (post baking).

[4] Hydrophobic Resin (D)

The composition of the present invention may contain a hydrophobic resin (D) (hereinafter also referred to as a "hydrophobic resin" or simply a "resin (D)"). The hydrophobic resin preferably has at least any one of a fluorine atom and a silicon atom. Further, the hydrophobic resin (D) is different from the resin (B).

At least any one of a fluorine atom and a silicon atom in the hydrophobic resin may be included in a main chain or a side chain of the resin.

In a case where the hydrophobic resin includes a fluorine atom, it is preferably a resin which has an alkyl group having a fluorine atom, a cycloalkyl group having a fluorine atom, or an aryl group having a fluorine atom as a partial structure having a fluorine atom.

The alkyl group having a fluorine atom is a linear or branched alkyl group in which at least one hydrogen atom is substituted with a fluorine atom, and preferably has 1 to 10 carbon atoms, and more preferably has 1 to 4 carbon atoms. Further, the group having a fluorine atom may further have a substituent.

A cycloalkyl group having a fluorine atom is a monocyclic or polycyclic cycloalkyl group in which at least one hydrogen atom is substituted with a fluorine atom. Incidentally, the cycloalkyl group having a fluorine atom may further have a substituent group other than a fluorine atom.

Examples of an aryl group having a fluorine atom include an aryl group in which at least one hydrogen atom of an aryl group such as a phenyl group and a naphthyl group is substituted with a fluorine atom, and the aryl group may further have a substituent group other than a fluorine atom.

Preferred examples of the hydrophobic resin include the hydrophobic resins described in paragraphs [0299] to [0491] of JP2012-093733A.

By incorporating the hydrophobic resin into the composition of the present invention, the hydrophobic resin is unevenly distributed on a surface layer of a film formed from the composition. In a case where the liquid immersion medium is water, the receding contact angle of the film surface with respect to water is increased so that the immersion-water tracking properties can be enhanced.

A receding contact angle of the resist film after the bake of a coating film formed of the composition of the present invention but prior to exposure thereof is preferably 60° or more, more preferably 65° or more, still more preferably 70° or more, and particularly preferably 75° or more, at a temperature during exposure, usually at room temperature 23±3° C. and a humidity of 45±5%. The upper limit is preferably 90° or less.

Although the hydrophobic resin is unevenly distributed on any interface as described above, as different from the surfactant, the resin does not necessarily have to have a hydrophilic group in its molecule and does not need to contribute toward uniform mixing of polar/nonpolar materials.

Since the hydrophobic resin is hydrophobic, it is likely to cause development residue (scum) and BLOB defects (development defects) after alkali development to deteriorate. However, in a case of using a hydrophobic resin having three or more polymer chains via at least one branch portion, as compared with a linear-chain resin, the alkali dissolution rate is increased, thereby improving the development residue (scum) and BLOB defect performance.

In a case where the hydrophobic resin contains fluorine atoms, the content of the fluorine atoms in terms of the weight-average molecular weight of the hydrophobic resin is preferably 5% to 80% by mass, and more preferably 10% to 80% by mass. Further, the content of the repeating unit including fluorine atoms is preferably 10% to 100% by mass, and more preferably 30% to 100% by mass, with respect to all the repeating units in the hydrophobic resin.

In a case where the hydrophobic resin has silicon atoms, the content of the silicon atoms in terms of the weight-average molecular weight of the hydrophobic resin is preferably 2% to 50% by mass, and more preferably 2% to 30% by mass. Further, the content of the repeating unit including silicon atoms is preferably 10% to 90% by mass, and more preferably 20% to 80% by mass, with respect to all the repeating units in the hydrophobic resin.

The weight-average molecular weight of the hydrophobic resin is preferably 1,000 to 100,000, more preferably 2,000 to 50,000 and still more preferably 3,000 to 30,000. Here, the weight-average molecular weight of the hydrophobic resin refers to the molecular weight in terms of polystyrene, as measured by GPC (carrier: tetrahydrofuran (THF)).

Specific examples of the hydrophobic resin are shown below. Further, in the following tables, the molar ratio (which corresponds to each repeating unit in order from left), the weight-average molecular weight, and the dispersity of the repeating units in each resin are shown.

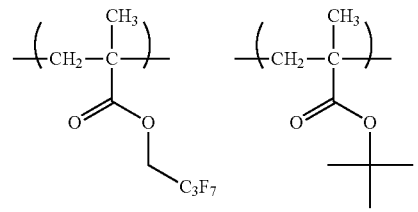 (HR-1)

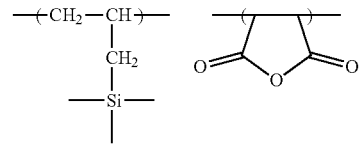 (HR-2)

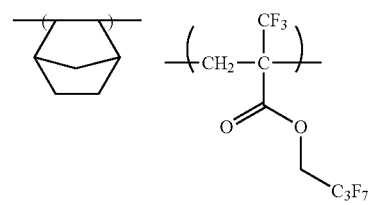 (HR-3)

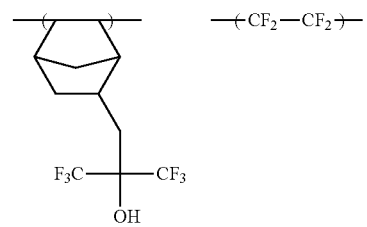 (HR-4)

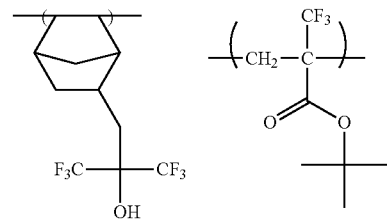 (HR-5)

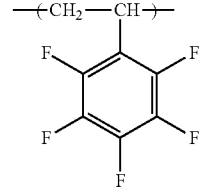 (HR-6)

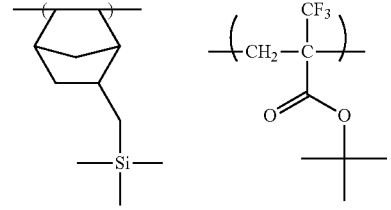 (HR-7)

(HR-8) 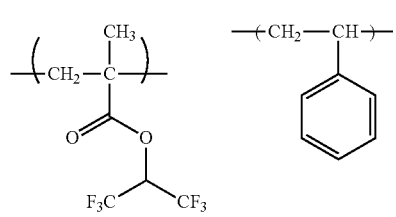
(HR-9) 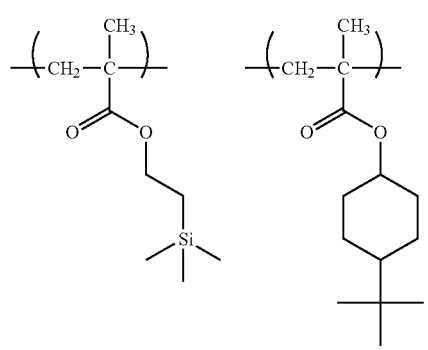
(HR-10) 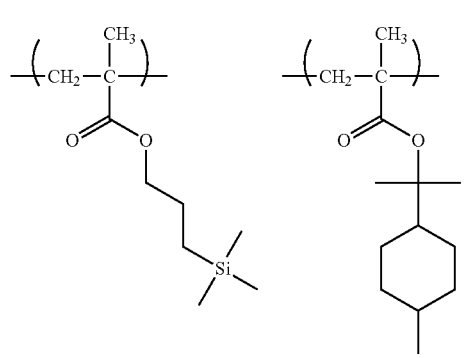
(HR-11) 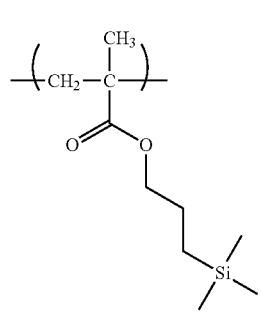
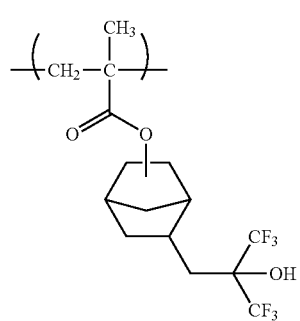
(HR-12) 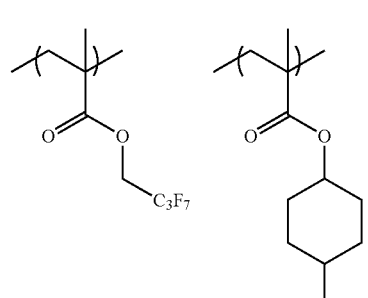
(HR-13) 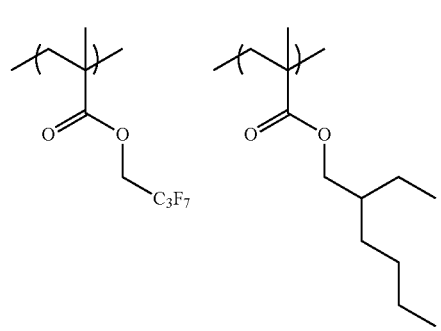
(HR-14) 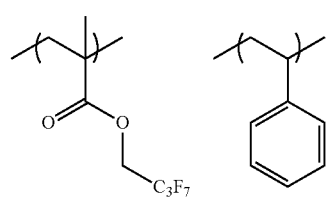
(HR-15) 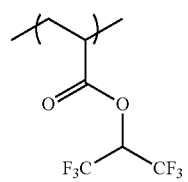
(HR-16) 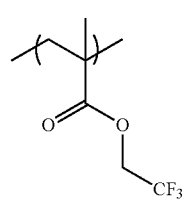
(HR-17) 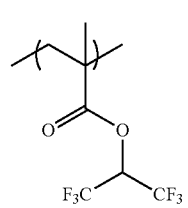

(HR-18) 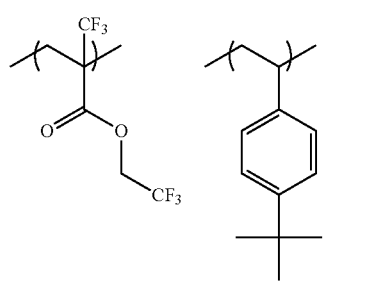
(HR-19) 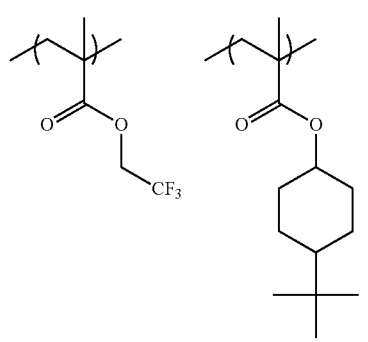
(HR-20) 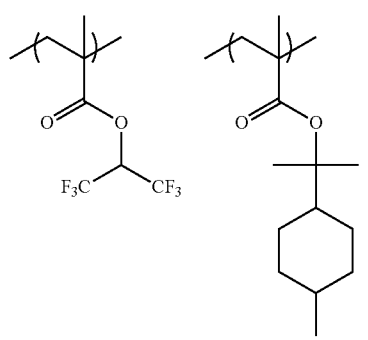
(HR-21) 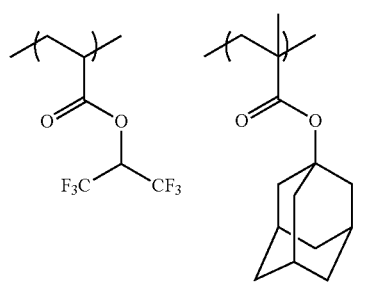
(HR-22) 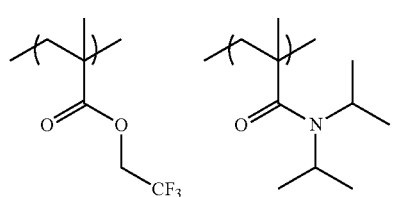
(HR-23) 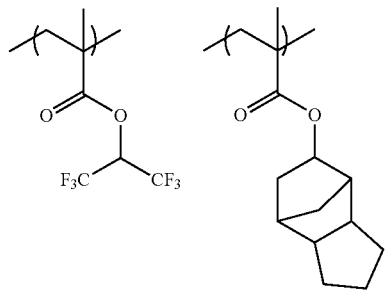
(HR-24) 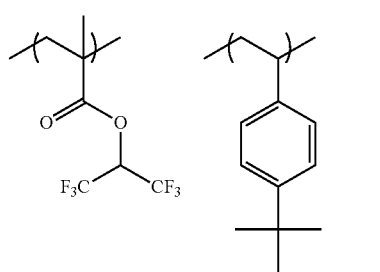
(HR-25) 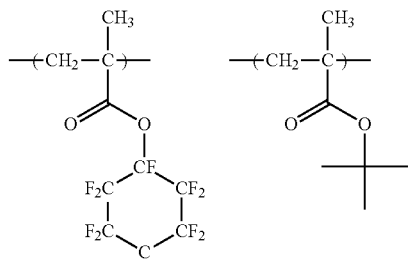
(HR-26) 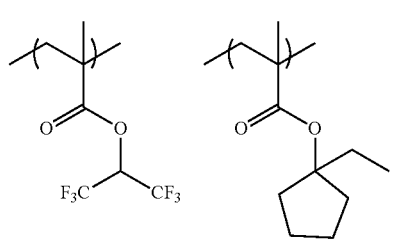
(HR-27) 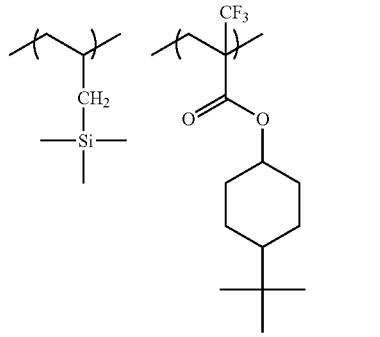
(HR-28) 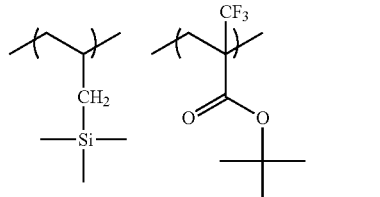

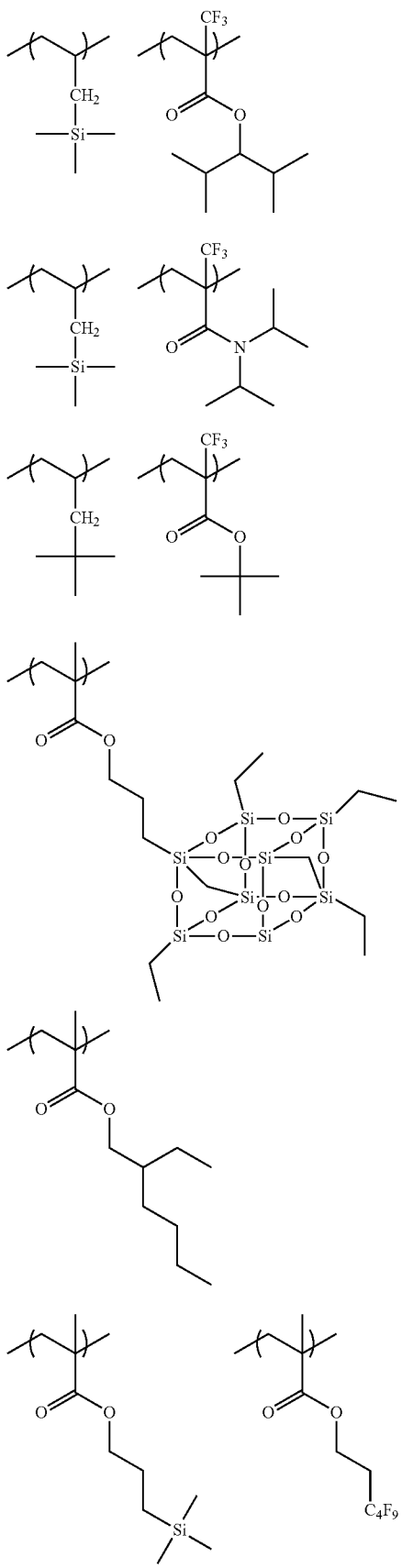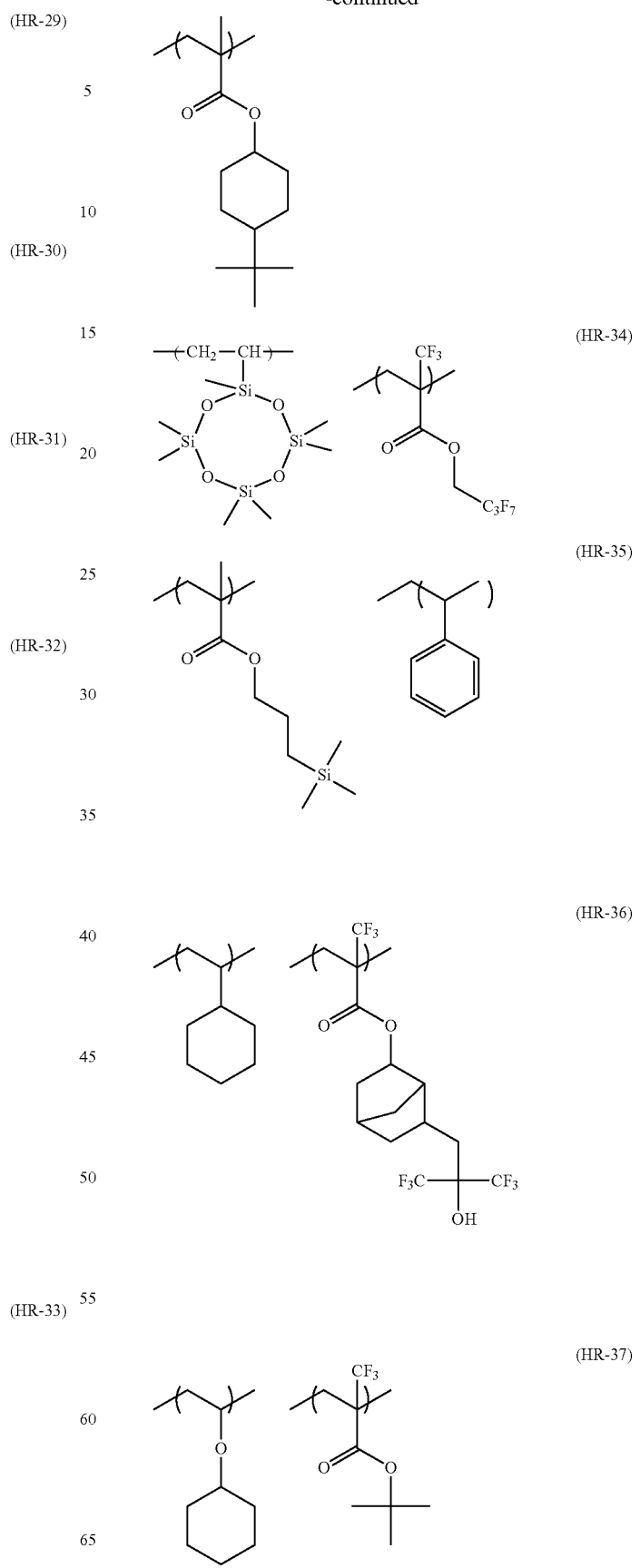

(HR-38)
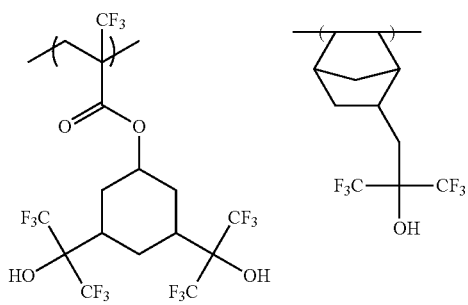
(HR-39)
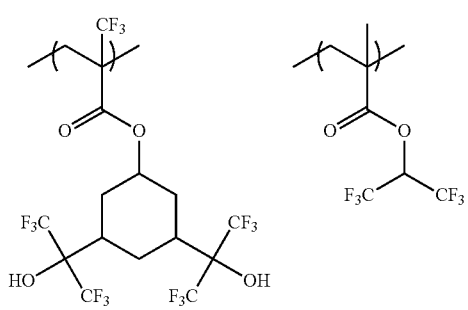
(HR-40)
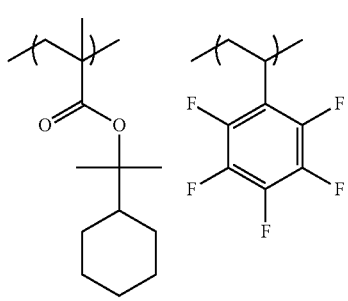
(HR-41)
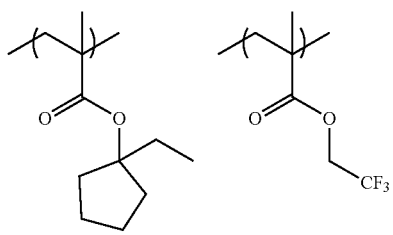
(HR-42)
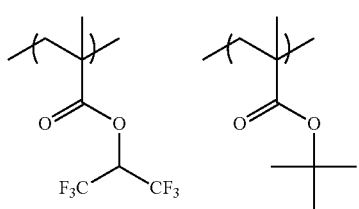
(HR-43)
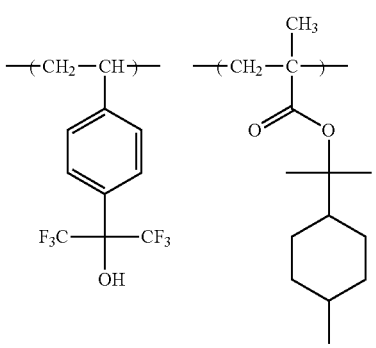
(HR-44)
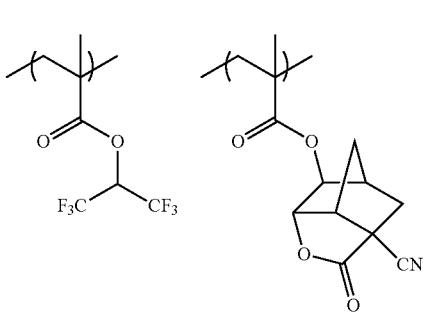
(HR-45)
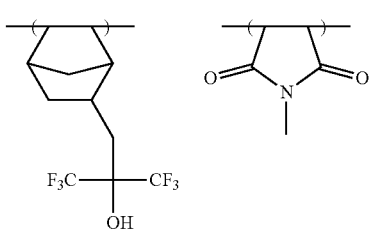
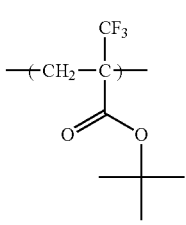
(HR-46)
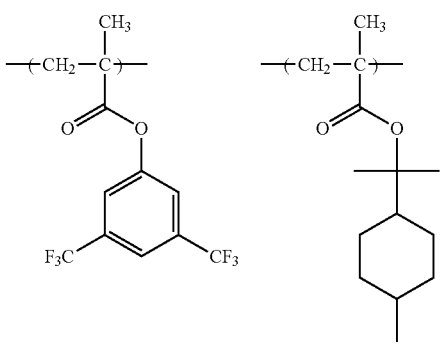

(HR-47)
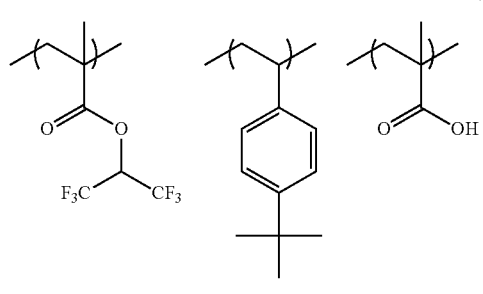
(HR-48)
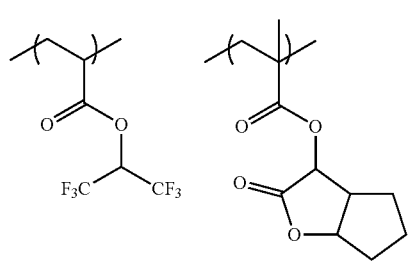
(HR-49)
(HR-50)
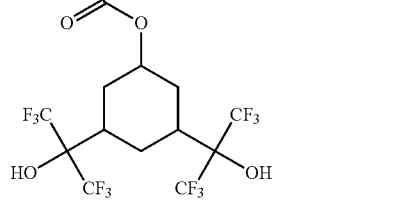
(HR-51)
(HR-52)
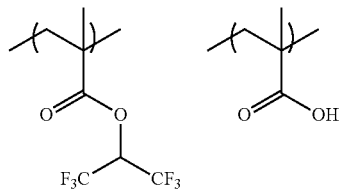
(HR-53)
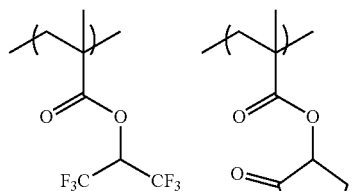
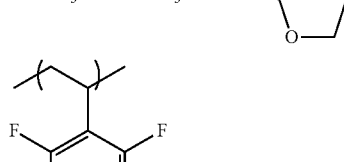
(HR-54)
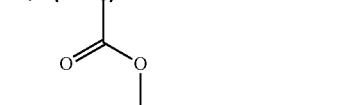
(HR-55)

-continued

-continued
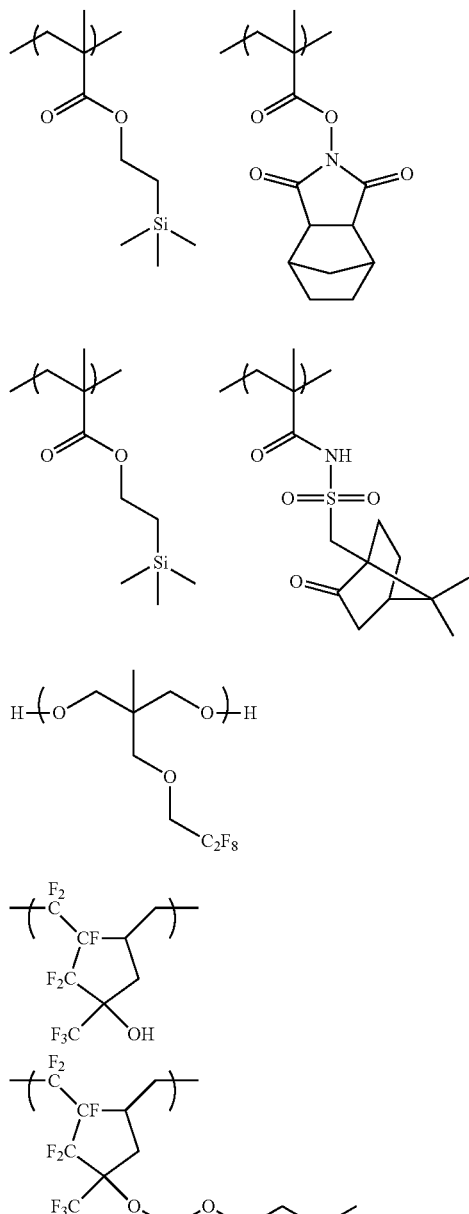
TABLE 1
| Resin | Composition | Mw | Mw/Mn |
|---|---|---|---|
| HR-1 | 50/50 | 4,900 | 1.4 |
| HR-2 | 50/50 | 5,100 | 1.6 |
| HR-3 | 50/50 | 4,800 | 1.5 |
| HR-4 | 50/50 | 5,300 | 1.6 |
| HR-5 | 50/50 | 4,500 | 1.4 |
| HR-6 | 100 | 5,500 | 1.6 |
| HR-7 | 50/50 | 5,800 | 1.9 |
| HR-8 | 50/50 | 4,200 | 1.3 |
| HR-9 | 50/50 | 5,500 | 1.8 |
| HR-10 | 40/60 | 7,500 | 1.6 |
| HR-11 | 70/30 | 6,600 | 1.8 |
| HR-12 | 40/60 | 3,900 | 1.3 |
| HR-13 | 50/50 | 9,500 | 1.8 |
| HR-14 | 50/50 | 5,300 | 1.6 |
| HR-15 | 100 | 6,200 | 1.2 |
TABLE 1-continued
| Resin | Composition | Mw | Mw/Mn |
|---|---|---|---|
| HR-16 | 100 | 5,600 | 1.6 |
| HR-17 | 100 | 4,400 | 1.3 |
| HR-18 | 50/50 | 4,300 | 1.3 |
| HR-19 | 50/50 | 6,500 | 1.6 |
| HR-20 | 30/70 | 6,500 | 1.5 |
| HR-21 | 50/50 | 6,000 | 1.6 |
| HR-22 | 50/50 | 3,000 | 1.2 |
| HR-23 | 50/50 | 5,000 | 1.5 |
| HR-24 | 50/50 | 4,500 | 1.4 |
| HR-25 | 30/70 | 5,000 | 1.4 |
| HR-26 | 50/50 | 5,500 | 1.6 |
| HR-27 | 50/50 | 3,500 | 1.3 |
| HR-28 | 50/50 | 6,200 | 1.4 |
| HR-29 | 50/50 | 6,500 | 1.6 |
| HR-30 | 50/50 | 6,500 | 1.6 |
| HR-31 | 50/50 | 4,500 | 1.4 |
| HR-32 | 30/70 | 5,000 | 1.6 |
| HR-33 | 30/30/40 | 6,500 | 1.8 |
| HR-34 | 50/50 | 4,000 | 1.3 |
| HR-35 | 50/50 | 6,500 | 1.7 |
| HR-36 | 50/50 | 6,000 | 1.5 |
| HR-37 | 50/50 | 5,000 | 1.6 |
| HR-38 | 50/50 | 4,000 | 1.4 |
| HR-39 | 20/80 | 6,000 | 1.4 |
| HR-40 | 50/50 | 7,000 | 1.4 |
| HR-41 | 50/50 | 6,500 | 1.6 |
| HR-42 | 50/50 | 5,200 | 1.6 |
| HR-43 | 50/50 | 6,000 | 1.4 |
| HR-44 | 70/30 | 5,500 | 1.6 |
| HR-45 | 50/20/30 | 4,200 | 1.4 |
| HR-46 | 30/70 | 7,500 | 1.6 |
| HR-47 | 40/58/2 | 4,300 | 1.4 |
| HR-48 | 50/50 | 6,800 | 1.6 |
| HR-49 | 100 | 6,500 | 1.5 |
| HR-50 | 50/50 | 6,600 | 1.6 |
| HR-51 | 30/20/50 | 6,800 | 1.7 |
| HR-52 | 95/5 | 5,900 | 1.6 |
| HR-53 | 40/30/30 | 4,500 | 1.3 |
| HR-54 | 50/30/20 | 6,500 | 1.8 |
| HR-55 | 30/40/30 | 7,000 | 1.5 |
| HR-56 | 60/40 | 5,500 | 1.7 |
| HR-57 | 40/40/20 | 4,000 | 1.3 |
| HR-58 | 60/40 | 3,800 | 1.4 |
| HR-59 | 80/20 | 7,400 | 1.6 |
| HR-60 | 40/40/15/5 | 4,800 | 1.5 |
| HR-61 | 60/40 | 5,600 | 1.5 |
| HR-62 | 50/50 | 5,900 | 2.1 |
| HR-63 | 80/20 | 7,000 | 1.7 |
| HR-64 | 100 | 5,500 | 1.8 |
| HR-65 | 50/50 | 9,500 | 1.9 |
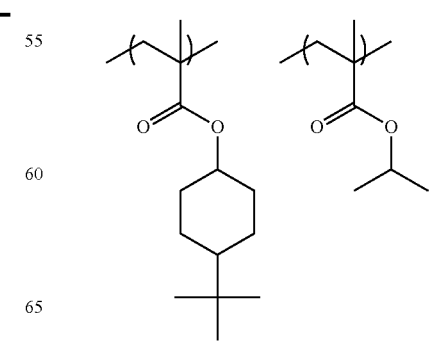
(C-1)

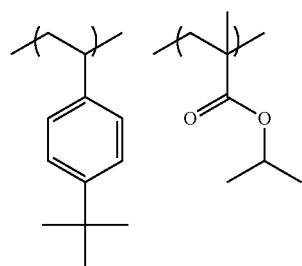 (C-2)
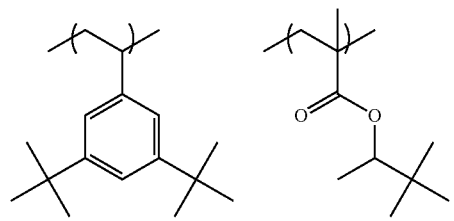 (C-3)
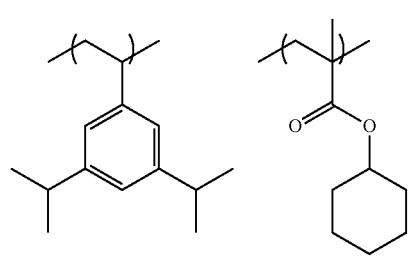 (C-4)
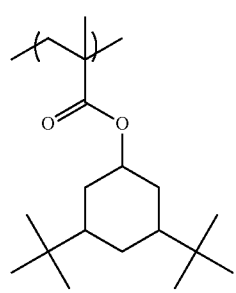 (C-5)
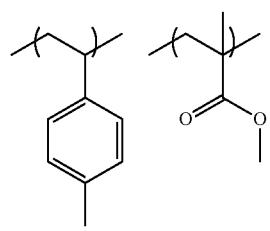 (C-6)
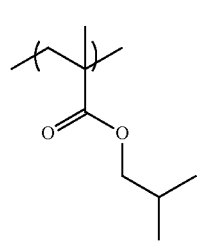 (C-7)
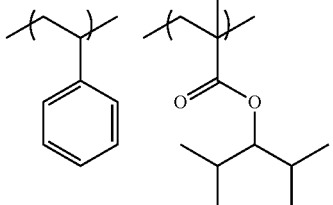 (C-8)
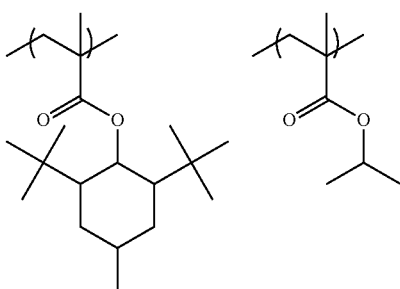 (C-9)
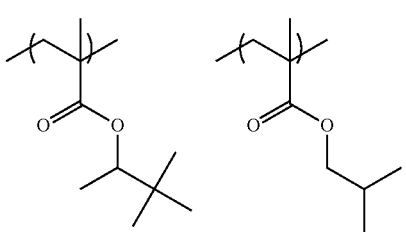 (C-10)
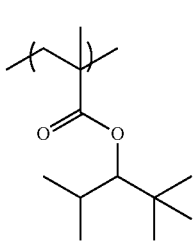 (C-11)
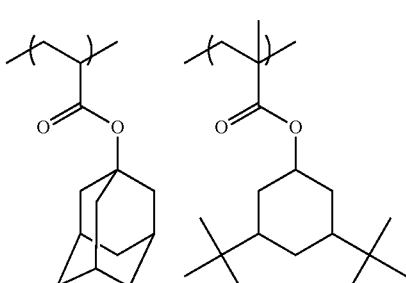 (C-12)
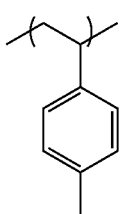 (C-13)

(C-14)
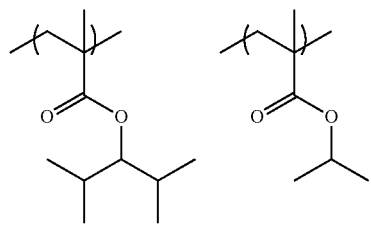
(C-15)
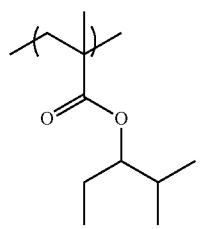
(C-16)
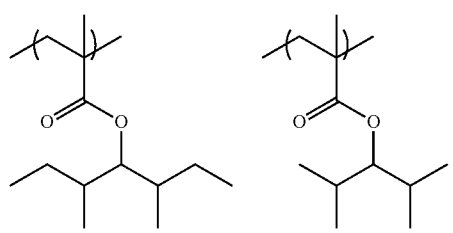
(C-17)
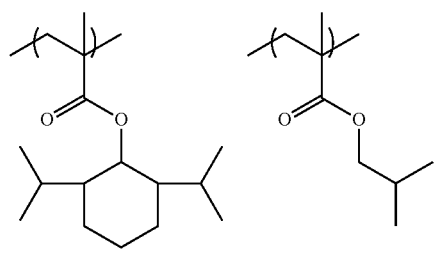
(C-18)
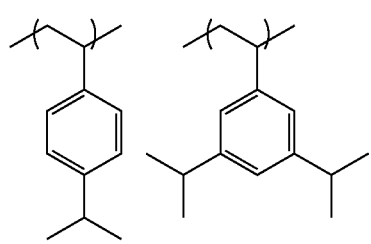
(C-19)
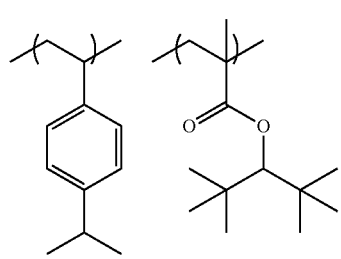
(C-20)
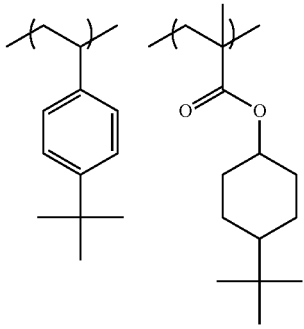
(C-21)
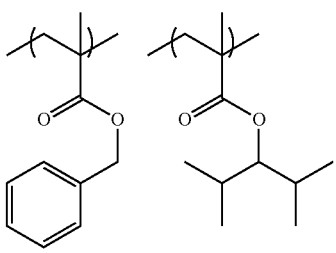
(C-22)
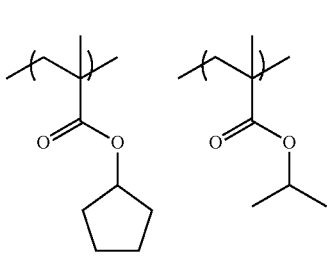
(C-23)
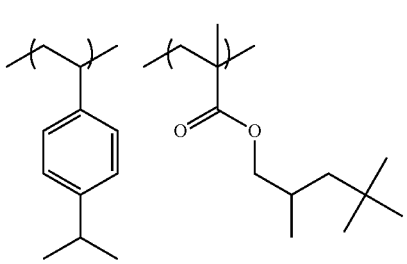
(C-24)
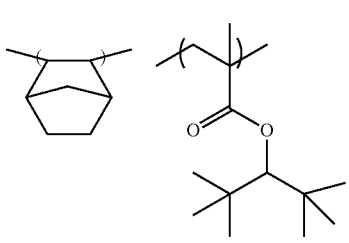

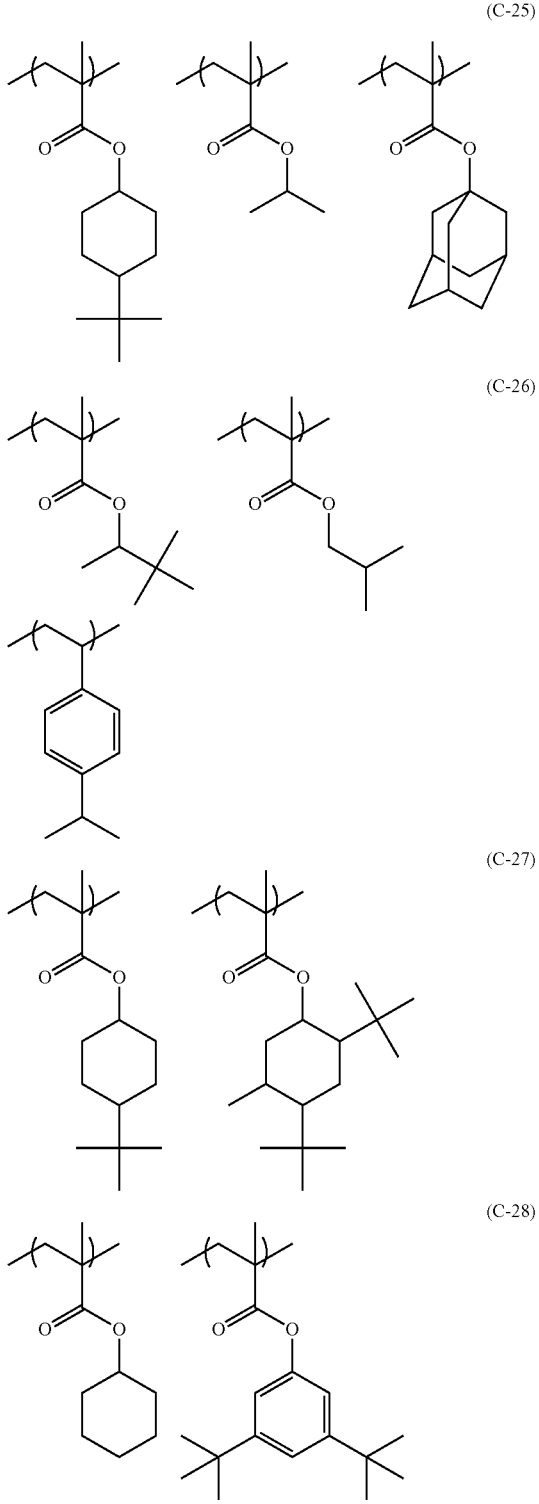

TABLE 2-continued

| Resin | Composition | Mw | Mw/Mn |
|---|---|---|---|
| C-4 | 90/10 | 26,400 | 1.41 |
| C-5 | 100 | 27,600 | 1.87 |
| C-6 | 80/20 | 4,400 | 1.96 |
| C-7 | 100 | 16,300 | 1.83 |
| C-8 | 5/95 | 24,500 | 1.79 |
| C-9 | 20/80 | 15,400 | 1.68 |
| C-10 | 50/50 | 23,800 | 1.46 |
| C-11 | 100 | 22,400 | 1.57 |
| C-12 | 10/90 | 21,600 | 1.52 |
| C-13 | 100 | 28,400 | 1.58 |
| C-14 | 50/50 | 16,700 | 1.82 |
| C-15 | 100 | 23,400 | 1.73 |
| C-16 | 60/40 | 18,600 | 1.44 |
| C-17 | 80/20 | 12,300 | 1.78 |
| C-18 | 40/60 | 18,400 | 1.58 |
| C-19 | 70/30 | 12,400 | 1.49 |
| C-20 | 50/50 | 23,500 | 1.94 |
| C-21 | 10/90 | 7,600 | 1.75 |
| C-22 | 5/95 | 14,100 | 1.39 |
| C-23 | 50/50 | 17,900 | 1.61 |
| C-24 | 10/90 | 24,600 | 1.72 |
| C-25 | 50/40/10 | 23,500 | 1.65 |
| C-26 | 60/30/10 | 13,100 | 1.51 |
| C-27 | 50/50 | 21,200 | 1.84 |
| C-28 | 10/90 | 19,500 | 1.66 |

The hydrophobic resin can be used singly or in combination of two or more kinds thereof.

The content of the hydrophobic resin in the composition can be adjusted so that the receding contact angle of the resist film falls within the range, but is preferably 0.01% to 20% by mass, more preferably 0.1% to 15% by mass, still more preferably 0.1% to 10% by mass, and particularly preferably 0.2 to 8% by mass, with respect to the total solid content of the composition.

[5] Solvent

The composition of the present invention may include a solvent.

As the solvent, an organic solvent is typically used. Examples of the organic solvent include alkylene glycol monoalkyl ether carboxylate, alkylene glycol monoalkyl ether, alkyl lactate ester, alkyl alkoxypropionate, a cyclic lactone (preferably having 4 to 10 carbon atoms), a monoketone compound (preferably having 4 to 10 carbon atoms) which may have a ring, alkylene carbonate, alkyl alkoxyacetate, and alkyl pyruvate.

Examples of the alkylene glycol monoalkyl ether carboxylate include propylene glycol monomethyl ether acetate (PGMEA; alternative name: 1-methoxy-2-acetoxypropane), propylene glycol monoethyl ether acetate, propylene glycol monopropyl ether acetate, propylene glycol monobutyl ether acetate, propylene glycol monomethyl ether propionate, propylene glycol monoethyl ether propionate, ethylene glycol monomethyl ether acetate, and ethylene glycol monoethyl ether acetate.

Examples of the alkylene glycol monoalkyl ether include propylene glycol monomethyl ether (PGME; alternative name: 1-methoxy-2-propanol), propylene glycol monoethyl ether, propylene glycol monopropyl ether, propylene glycol monobutyl ether, ethylene glycol monomethyl ether, and ethylene glycol monoethyl ether.

Examples of the alkyl lactate ester include methyl lactate, ethyl lactate, propyl lactate, and butyl lactate.

Examples of the alkyl alkoxypropionate include ethyl 3-ethoxypropionate, methyl 3-methoxypropionate, methyl 3-ethoxypropionate, and ethyl 3-methoxypropionate.

Preferred examples of the cyclic lactone include β-propiolactone, β-butyrolactone, γ-butyrolactone, α-methyl-γ-

TABLE 2

| Resin | Composition | Mw | Mw/Mn |
|---|---|---|---|
| C-1 | 50/50 | 9,600 | 1.74 |
| C-2 | 60/40 | 34,500 | 1.43 |
| C-3 | 30/70 | 19,300 | 1.69 | butyrolactone, β-methyl-γ-butyrolactone, γ-valerolactone, γ-caprolactone, γ-octanoic lactone, and α-hydroxy-γ-butyrolactone.

Examples of the monoketone compound which may contain a ring include 2-butanone, 3-methylbutanone, pinacolone, 2-pentanone, 3-pentanone, 3-methyl-2-pentanone, 4-methyl-2-pentanone, 2-methyl-3-pentanone, 4,4-dimethyl-2-pentanone, 2,4-dimethyl-3-pentanone, 2,2,4,4-tetramethyl-3-pentanone, 2-hexanone, 3-hexanone, 5-methyl-3-hexanone, 2-heptanone, 3-heptanone, 4-heptanone, 2-methyl-3-heptanone, 5-methyl-3-heptanone, 2,6-dimethyl-4-heptanone, 2-octanone, 3-octanone, 2-nonanone, 3-nonanone, 5-nonanone, 2-decanone, 3-decanone, 4-decanone, 5-hexen-2-one, 3-penten-2-one, cyclopentanone, 2-methylcyclopentanone, 3-methylcyclopentanone, 2,2-dimethylcyclopentanone, 2,4,4-trimethylcyclopentanone, cyclohexanone, 3-methylcyclohexanone, 4-methylcyclohexanone, 4-ethylcyclohexanone, 2,2-dimethylcyclohexanone, 2,6-dimethylcyclohexanone, 2,2,6-trimethylcyclohexanone, cycloheptanone, 2-methylcycloheptanone, and 3-methylcycloheptanone.

Examples of the alkylene carbonate include propylene carbonate, vinylene carbonate, ethylene carbonate, and butylene carbonate.

Examples of the alkyl alkoxyacetate include 2-methoxyethyl acetate, 2-ethoxyethyl acetate, 2-(2-ethoxyethoxy) ethyl acetate, 3-methoxy-3-methylbutyl acetate, and 1-methoxy-2-propyl acetate.

Examples of the alkyl pyruvate include methyl pyruvate, ethyl pyruvate, and propyl pyruvate.

The solvent preferably has a boiling point of 130° C. or higher at a normal temperature and a normal pressure.

These solvents may be used singly or in combination of two or more kinds thereof. In the latter case, it is preferable to use a mixed solvent obtained by mixing a solvent including a hydroxyl group with a solvent not including a hydroxyl group.

Examples of the solvent including a hydroxyl group include ethylene glycol, ethylene glycol monomethyl ether, ethylene glycol monoethyl ether, propylene glycol, PGME, propylene glycol monoethyl ether, and ethyl lactate. Among those, PGME or ethyl lactate is preferable.

Examples of the solvent not including a hydroxyl group include PGMEA, ethylethoxypropionate, 2-heptanone, γ-butyrolactone, cyclohexanone, butyl acetate, N-methylpyrrolidone, N,N-dimethylacetamide, and dimethylsulfoxide. Among those, PGMEA, ethylethoxypropionate, or 2-heptanone is preferable.

In a case where a mixed solvent of the solvent including a hydroxyl group and the solvent not including a hydroxyl group is used, the mass ratio thereof is preferably 1/99 to 99/1, more preferably 10/90 to 90/10, and still more preferably 20/80 to 60/40.

Moreover, in a case where a mixed solvent including the solvent not including a hydroxyl group in the amount of 50% by mass or more, it is possible to attain particularly excellent coating evenness. Incidentally, the solvent is preferably a mixed solvent of PGMEA with other one or more kinds of solvents.

The content of the solvent in the composition of the present invention can be appropriately adjusted in accordance with a desired film thickness or the like, but in general, the content is adjusted so that the total concentration of the solid content of the composition is 0.5% to 30% by mass, preferably 1.0% to 20% by mass, and more preferably 1.5% to 10% by mass.

[6] Surfactant

The composition of the present invention may further contain a surfactant. In a case where the composition contains the surfactant, it is preferable that the composition contains any one of a surfactant including at least one of a fluorine atom and a silicon atom (a fluorine-based surfactant, a silicon-based surfactant, and a surfactant having both a fluorine atom and a silicon atom), or two or more kinds thereof.

Examples of the fluorine-based surfactant and/or the silicon-based surfactants include the surfactants described in [0276] in US2008/0248425A. Further, EFTOP EF301 or EF303 (manufactured by Shin-Akita Kasei K. K.); FLORAD FC430, 431, or 4430 (manufactured by Sumitomo 3M Inc.); MEGAFACE F171, F173, F176, F189, F113, F110, F177, F120, or R08 (manufactured by DIC Corp.); SURFLON S-382, SCI01, 102, 103, 104, 105, or 106 (manufactured by Asahi Glass Co., Ltd.); TROYSOL S-366 (manufactured by Troy Chemical Corp.); GF-300 or GF-150 (manufactured by Toagosei Chemical Industry Co., Ltd.); SURFLON S-393 (manufactured by Seimi Chemical Co., Ltd.); EFTOP EF121, EF122A, EF122B, RF122C, EF125M, EF135M, EF351, EF352, EF801, EF802, or EF601 (manufactured by JEMCO Inc.); PF636, PF656, PF6320, or PF6520 (manufactured by OMNOVA Solutions Inc.); or FTX-204G, 208G, 218G, 230G, 204D, 208D, 212D, 218D, or 222D (manufactured by NEOS COMPANY LIMITED) may be used. In addition, POLYSILOXANE POLYMER KP-341 (manufactured by Shin-Etsu Chemical Co., Ltd.) can also be used as the silicon-based surfactant.

Examples of the commercially available surfactant include MEGAFACE F178, F-470, F-473, F-475, F-476, and F-472 (manufactured by DIC Corp.); a copolymer of an acrylate (or methacrylate) having a $C_6F_{13}$ group with a (poly(oxyalkylene)) acrylate (or methacrylate); and a copolymer of an acrylate (or methacrylate) having a $C_3F_7$ group with a (poly(oxyethylene)) acrylate (or methacrylate) and a (poly(oxypropylene)) acrylate (or methacrylate).

In addition, in the present invention, surfactants other than the fluorine- and/or silicon-based surfactants described in paragraph [0280] of US2008/0248425A can also be used.

These surfactants may be used singly or in combination of two or more kinds thereof.

The content of the surfactant is preferably 0% to 2% by mass, more preferably 0% to 1.5% by mass, and still more preferably 0% to 1% by mass, with respect to the total solid content (the total amount excluding the solvent) of the composition.

[7] Onium Carboxylate Salt

The composition of the present invention may contain an onium carboxylate salt. As the onium carboxylate salt, an iodonium salt or a sulfonium salt is preferable. As an anionic moiety thereof, a linear, branched, or monocyclic or polycyclic alkylcarboxylate anion having 1 to 30 carbon atoms is preferable. More preferably, a carboxylate anion in which a part or all of the alkyl groups are substituted with fluorine is preferable. An oxygen atom may be contained in the alkyl group, by which the transparency to light at 220 nm or less is ensured, thus, sensitivity and resolving power are enhanced, and density dependency and exposure margin are improved.

Examples of the fluorine-substituted carboxylate anion include anions of fluoroacetic acid, difluoroacetic acid, trifluoroacetic acid, pentafluoropropionic acid, heptafluorobutyric acid, nonafluoropentanoic acid, perfluorododecanoic acid, perfluorotridecanoic acid, perfluorocyclohexanecarboxylic acid, and 2,2-bistrifluoromethylpropionic acid.

The content of the onium carboxylate salt in the composition is generally 0.1% to 20% by mass, preferably 0.5% to 10% by mass, and more preferably 1% to 7% by mass, with respect to the total solid content of the composition.

[8] Dissolution Inhibiting Compound Having Molecular Weight of 3,000 or Less, which Decomposes by Action of Acid to Increase its Solubility in Alkali Developer The composition of the present invention may contain a dissolution inhibiting compound having a molecular weight of 3,000 or less, which decomposes by the action of an acid to increase its solubility in an alkali developer (hereinafter also referred to as a "dissolution inhibiting compound"). As the dissolution inhibiting compound, an alicyclic or aliphatic compound containing an acid-decomposable group, such as a cholic acid derivative including an acid-decomposable group, described in Proceeding of SPIE, 2724, 355 (1996), is preferable so as not to decrease the transmittance at 220 nm or less.

Furthermore, in a case where the composition of the present invention is exposed to KrF excimer laser or irradiated with electron beams, it is preferable to contain a structure resulting from substitution of the phenolic hydroxyl group of a phenol compound with an acid-decomposable group as the dissolution inhibiting compound. The phenol compound preferably contains 1 to 9 phenol skeletons, and more preferably 2 to 6 phenol skeletons.

The amount of the dissolution inhibiting compound to be added is preferably 3% to 50% by mass, and more preferably 5% to 40% by mass, with respect to the total solid content of the composition.

Specific examples of the dissolution inhibiting compound are shown below, but the present invention is not limited thereto.

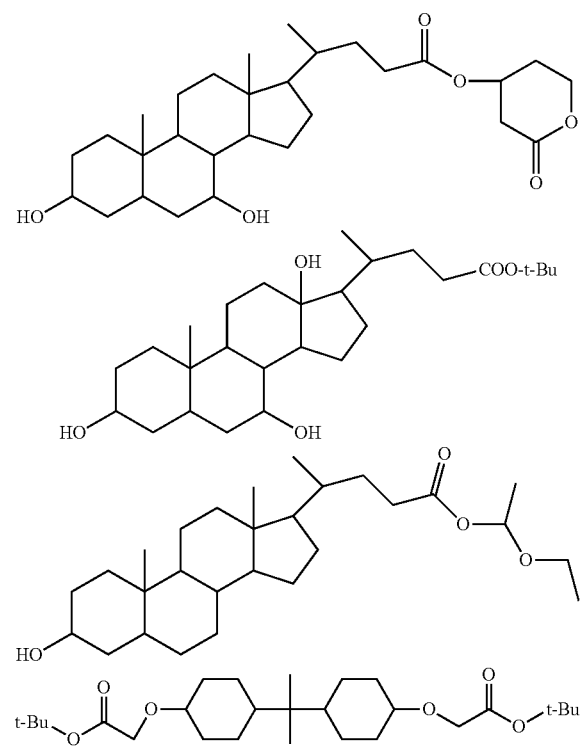

-continued

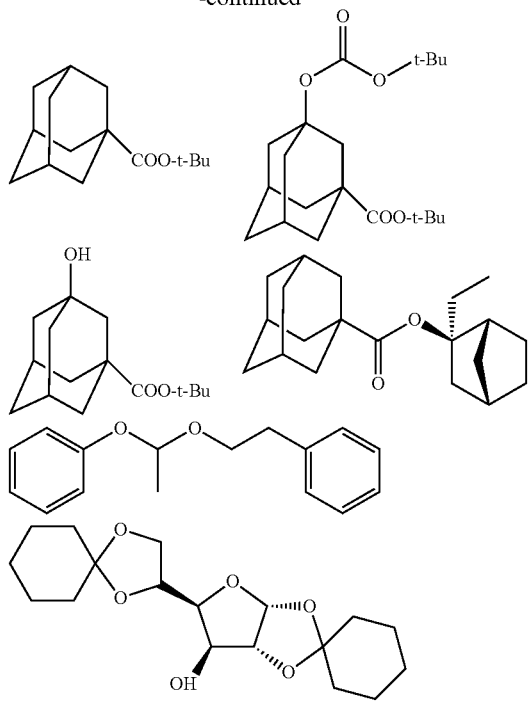

[9] Other Additives

The composition of the present invention may further contain a dye, a plasticizer, a light sensitizer, a light absorbent, a compound promoting solubility in a developer (for example, a phenol compound having a molecular weight of 1,000 or less, and an alicyclic or aliphatic compound having a carboxyl group), and the like, if desired.

Such a phenol compound having a molecular weight of 1,000 or less can be easily synthesized by those skilled in the art with reference to the method disclosed in, for example, JP1992-122938A (JP-H04-122938A), JP1990-28531A (JP-H02-28531A), U.S. Pat. No. 4,916,210A, EP219294B, and the like.

Specific examples of the alicyclic or aliphatic compound having a carboxyl group include, but not limited to, a carboxylic acid derivative having a steroid structure such as a cholic acid, deoxycholic acid or lithocholic acid, an adamantane carboxylic acid derivative, adamantane dicarboxylic acid, cyclohexane carboxylic acid, and cyclohexane dicarboxylic acid.

<Pattern Forming Method>

The pattern forming method of the present invention is carried out using the above-mentioned actinic ray-sensitive or radiation-sensitive resin composition.

Specifically, the pattern forming method of the present invention includes a step of forming a film (resist film) of the above-mentioned actinic ray-sensitive or radiation-sensitive resin composition on a substrate (hereinafter also referred to as a "step (1)" or a "film forming step"), a step of exposing the resist film (hereinafter also referred to as a "step (2)" or an "exposing step"), a step of performing development of the resist film irradiated with actinic rays or radiation using a developer (hereinafter also referred to as a "step (3)" or an "exposing step").

Hereinafter, each of the steps will be described in detail.

[Step (1): Film Forming Step]

The procedure of the step (1) is not particularly limited, but examples thereof include a method in which the composition of the present invention is applied onto a substrate, and subjected to a curing treatment, as desired (application method), and a method in which a resist film is formed on a temporary support and the resist film is transferred onto a substrate. Among those, the application method is preferable due to excellent productivity.

The substrate is not particularly limited, and an inorganic substrate such as silicon, SiN, $SiO_2$, and TiN, a coating type inorganic substrate such as spin on glass (SOG), or a substrate generally used in a process for manufacturing a semiconductor such as an IC, in a process for manufacturing of a circuit board for a liquid crystal, a thermal head, or the like, and in other lithographic processes of photofabrication can be used. Further, an antireflection film may further be formed, if desired, between the resist film and the substrate. As the antireflection film, a known organic or inorganic antireflection film can be appropriately used.

Furthermore, the pattern forming method of the present invention may be combined with a two-layer resist process, for example, as disclosed in JP2008-083384A, or may be combined with a process including performing multiple exposure and development as disclosed in WO2011/122336A. In a case where the present invention is combined with the process disclosed in WO2011/122336A, it is preferable that the pattern forming method of the present invention is applied as the second negative tone pattern forming method in Claim 1 of WO2011/122336A.

The thickness of the resist film (actinic ray-sensitive or radiation-sensitive film) is not particularly limited, but is preferably 1 to 500 nm, and more preferably 1 to 100 nm since a fine pattern with higher accuracy can be formed. Among those, the thickness is still more preferably 80 nm or less. By setting the concentration of the solid contents in the composition to an appropriate range to obtain a suitable viscosity, the coatability and the film forming properties can be improved, thereby providing such a film thickness.

[Step (2): Exposing Step]

The step (2) is a step of exposing the resist film (actinic ray-sensitive or radiation-sensitive film) (irradiating the resist film with actinic rays or radiation) formed in the step (1).

The light used for the exposure is not particularly limited, and examples thereof include infrared rays, visible light, ultraviolet rays, far ultraviolet rays, extreme ultraviolet rays, X-rays, and electron beams, preferably far ultraviolet rays at a wavelength of 250 nm or less, more preferably far ultraviolet rays at a wavelength of 220 nm or less, and still more preferably far ultraviolet rays at a wavelength of 1 to 200 nm.

More specific examples thereof include a KrF excimer laser (248 nm), an ArF excimer laser (193 nm), an F2 excimer laser (157 nm), X-rays, EUV (13 nm), and electron beams. Among those, the KrF excimer laser, the ArF excimer laser, EUV, or the electron beams are preferable, and the ArF excimer laser is more preferable.

A liquid immersion exposure method can be applied to the exposing step. It is possible to combine the liquid immersion exposure method with a super-resolution technique such as a phase shift method and a modified illumination method. The liquid immersion exposure can be carried out by the method described in, for example, paragraphs [0594] to [0601] of JP2013-242397A.

Moreover, in a case where the receding contact angle of the resist film formed using the composition of the present invention is extremely small, it cannot be suitably used in a case of carrying out exposure through a liquid immersion medium, and further, an effect of reducing watermark defect cannot be sufficiently exhibited. In order to realize a preferred receding contact angle, it is preferable to incorporate the hydrophobic resin (D) into the composition. Alternatively, a film (hereinafter also referred to as a "topcoat") sparingly soluble in an immersion liquid, which is formed with the hydrophobic resin (D) on the upper layer of the resist film, may be provided on a resist film including the hydrophobic resin (D). The functions required for the topcoat are coating suitability on the upper layer part of the resist film, and sparing solubility in an immersion liquid. It is preferable that the topcoat is not mixed with the resist film and can be uniformly applied onto the upper layer of the resist film.

The topcoat is not particularly limited, and a topcoat known in the related art can be formed by a method known in the related art, and can be formed according to the description in, for example, paragraphs [0072] to [0082] of JP2014-059543A.

It is preferable that a topcoat containing the basic compound described in JP2013-61648A is formed on a resist film.

In addition, even in a case of performing exposure by a method other than the liquid immersion exposure method, the topcoat may be formed on the resist film.

The resist film exposed in the step (2) after the step (2) and before the step (3) which will be described later may be subject to a heating treatment (PEB: Post Exposure Bake). The reaction in the exposed area in the present step is accelerated. The heating treatment (PEB) may be carried out plural times.

The temperature for the heating treatment is preferably 70° C. to 130° C., and more preferably 80° C. to 120° C.

The time for the heating treatment is preferably 30 to 300 seconds, more preferably 30 to 180 seconds, and still more preferably 30 to 90 seconds.

The heating treatment may be carried out using a means equipped in an ordinary exposure/development machine, or may also be carried out using a hot plate or the like.

[Step (3): Developing Step]

The pattern forming method of the present invention has a developing step. A developer is not particularly limited, and examples thereof include an alkali developer and a developer including an organic solvent.

The step (3) may also be a step of developing the resist film exposed in the step (2) (the resist film irradiated with actinic rays or radiation) using an alkali developer.

For the alkali developer, an aqueous alkali solution including an alkali is preferably used. The type of the aqueous alkali solution is not particularly limited, but examples thereof include aqueous alkali solutions including a quaternary ammonium salt typified by tetramethylammonium hydroxide, an inorganic alkali, a primary amine, a secondary amine, a tertiary amine, an alcoholamine, a cyclic amine, and the like. Among those, an aqueous solution of a quaternary ammonium salt typified by tetramethylammonium hydroxide (TMAH) is preferable as the alkali developer. An appropriate amount of alcohols, a surfactant, or the like may also be added to the alkali developer. The alkali concentration of the alkali developer is usually 0.1% to 20% by mass. Incidentally, the pH of the alkali developer is usually 10.0 to 15.0.

Furthermore, the step (3) may be a step of developing the resist film exposed in the step (2) (the resist film irradiated with actinic rays or radiation) using a developer including an organic solvent (hereinafter also referred to as an "organic solvent developer"). In a view that the peeling and the development of a topcoat can be carried out simultaneously, it is preferable to carry out development using a developer including an organic solvent.

As the organic solvent developer, a polar solvent such as a ketone-based solvent, an ester-based solvent, an alcohol-based solvent, an amide-based solvent, and an ether-based solvent, or a hydrocarbon-based solvent can be used.

Examples of the ketone-based solvent include 1-octanone, 2-octanone, 1-nonanone, 2-nonanone, acetone, 2-heptanone (methyl amyl ketone), 4-heptanone, 1-hexanone, 2-hexanone, diisobutyl ketone, cyclohexanone, methylcyclohexanone, phenylacetone, methyl ethyl ketone, methyl isobutyl ketone, acetylacetone, acetonylacetone, ionone, diacetonyl alcohol, acetyl carbinol, acetophenone, methyl naphthyl ketone, isophorone, and propylene carbonate.

Examples of the ester-based solvent include methyl acetate, butyl acetate, ethyl acetate, isopropyl acetate, pentyl acetate, isopentyl acetate, amyl acetate, propylene glycol monomethyl ether acetate, ethylene glycol monoethyl ether acetate, diethylene glycol monobutyl ether acetate, diethylene glycol monoethyl ether acetate, ethyl-3-ethoxypropionate, 3-methoxybutyl acetate, 3-methyl-3-methoxybutyl acetate, methyl formate, ethyl formate, butyl formate, propyl formate, ethyl lactate, butyl lactate, propyl lactate, methyl 2-hydroxyisobutyrate, isobutyl isobutyrate, butyl propionate, butyl butanoate, and isoamyl acetate.

Examples of the alcohol-based solvent include alcohols such as methyl alcohol, ethyl alcohol, n-propyl alcohol, isopropyl alcohol, n-butyl alcohol, sec-butyl alcohol, tert-butyl alcohol, isobutyl alcohol, n-hexyl alcohol, n-heptyl alcohol, n-octyl alcohol, and n-decanol; glycol-based solvents such as ethylene glycol, diethylene glycol, and triethylene glycol; and glycol ether-based solvents such as ethylene glycol monomethyl ether, propylene glycol monoethyl ether, diethylene glycol monomethyl ether, triethylene glycol monoethyl ether, and methoxymethylbutanol.

Examples of the ether-based solvent include, in addition to the glycol ether-based solvents, dioxane, and tetrahydrofuran.

Examples of the amide-based solvent include N-methyl-2-pyrrolidone, N,N-dimethylacetamide, N,N-dimethylformamide, hexamethylphosphoric triamide, and 1,3-dimethyl-2-imidazolidinone.

Examples of the hydrocarbon-based solvent include aromatic hydrocarbon-based solvents such as toluene and xylene, and aliphatic hydrocarbon-based solvents such as pentane, hexane, octane, and decane.

A plurality of these solvents may be mixed and used, or the solvent may be mixed with a solvent other than those described above or with water, and used. However, in order to sufficiently bring out the effect of the present invention, the moisture content in the entire developer is preferably less than 10% by mass, and it is more preferable that the developer contains substantially no moisture.

That is, the amount of the organic solvent to be used with respect to the organic solvent developer is preferably from 90% by mass to 100% by mass, and more preferably from 95% by mass to 100% by mass, with respect to the total amount of the developer.

The vapor pressure of the organic solvent developer is preferably 5 kPa or less, more preferably 3 kPa or less, and still more preferably 2 kPa or less, at 20° C. By setting the vapor pressure of the organic solvent developer to 5 kPa or less, the evaporation on a substrate or in a developing cup of the developer is suppressed, and the temperature uniformity within a substrate plane is improved, whereby the dimensional uniformity within a substrate plane is enhanced.

An appropriate amount of a surfactant may be added to the organic solvent developer, as desired.

The surfactant is not particularly limited, but examples thereof include an ionic or non-ionic, fluorine-based surfactant and/or silicon-based surfactant. Examples of the fluorine surfactant and/or the silicon-based surfactant include surfactants described in JP1987-36663A (JP-S62-36663A), JP1986-226746A (JP-S61-226746A), JP1986-226745A (JP-S61-226745A), JP1987-170950A (JP-S62-170950A), JP1988-34540A (JP-S63-34540A), JP1995-230165A (JP-H07-230165A), JP1996-62834A (JP-H08-62834A), JP1997-54432A (JP-H09-54432A), JP1997-5988A (JP-H09-5988A), and U.S. Pat. Nos. 5,405,720A, 5,360,692A, 5,529,881 A, 5,296,330A, 5,436,098A, 5,576,143A, 5,294,511A, and 5,824,451A, with the non-ionic surfactant being preferable.

The amount of the surfactant to be used is usually 0.001% to 5% by mass, preferably 0.005% to 2% by mass, and more preferably 0.01% to 0.5% by mass, with respect to the total amount of the developer.

The organic solvent developer may include a basic compound. Specific and preferred examples of the basic compound which can be included in the organic solvent developer used in the present invention are the same as those for the basic compound which can be included in the composition as mentioned above as the acid diffusion control agent.

As the developing method, for example, a method in which a substrate is immersed in a tank filled with a developer for a certain period of time (a dip method), a method in which a developer is heaped up to the surface of a substrate by surface tension and developed by stopping for a certain period of time (a paddle method), a method in which a developer is sprayed on the surface of a substrate (a spray method), a method in which a developer is continuously discharged on a substrate rotated at a constant rate while scanning a developer discharging nozzle at a constant rate (a dynamic dispense method), or the like, can be applied. Further, suitable ranges of the discharge pressure of the developer to be discharged, methods for adjusting the discharge pressure of the developer, and the like are not particularly limited, and for example, the ranges and the methods described in paragraphs [0631] to [0636] of JP2013-242397A can be used.

In the pattern forming method of the present invention, a combination of a step of carrying out development using a developer including an organic solvent (organic solvent developing step) and a step of carrying out development using an aqueous alkali solution (alkali developing step) may be used, whereby a finer pattern can be formed.

In the present invention, an area with low exposure intensity is removed in the organic solvent developing step, and by further carrying out the alkali developing step, an area with high exposure intensity is also removed. By virtue of a multiple-development process in which development is carried out in plural times in this manner, a pattern can be formed by keeping only a region with an intermediate exposure intensity from not being dissolved, so that a finer pattern than usual can be formed (the same mechanism as in [0077] of JP2008-292975A).

In the pattern forming method of the present invention, the order of the alkali developing step and the organic solvent developing step is not particularly limited, but the alkali development is more preferably carried out before the organic solvent developing step.

It is preferable that the method includes a step of performing washing using a rinsing liquid after the step of carrying out development using a developer. Examples of the rinsing liquid to be used in the rinsing step after the step of performing development using an alkali developer include pure water. Further, an appropriate amount of a surfactant may be added to pure water.

The rinsing liquid used in the rinsing step after the step of carrying out development using a developer including an organic solvent is not particularly limited as long as the rinsing liquid does not dissolve the pattern, and examples thereof include a solution including a common organic solvent. As the rinsing liquid, a rinsing liquid containing at least one organic solvent selected from the group consisting of a hydrocarbon-based solvent, a ketone-based solvent, an ester-based solvent, an alcohol-based solvent, an amide-based solvent, and an ether-based solvent is preferable.

Specific examples of the hydrocarbon-based solvent, the ketone-based solvent, the ester-based solvent, the alcohol-based solvent, the amide-based solvent, and the ether-based solvent include the same solvents as those described for the developer including an organic solvent.

The hydrocarbon-based solvent included in the rinsing liquid is preferably a hydrocarbon compound having 6 to 30 carbon atoms, more preferably a hydrocarbon compound having 8 to 30 carbon atoms, and still more preferably a hydrocarbon compound having 10 to 30 carbon atoms. By using a rinsing liquid including decane and/or undecane among those, pattern collapse is further suppressed.

In a case where the ester-based solvent is used as the rinsing liquid, a glycol ether-based solvent may be used, in addition to the ester-based solvent (one kind or two or more kinds). Specific examples of such a case include use of an ester-based solvent (preferably butyl acetate) as a main component and a glycol ether-based solvent (preferably propylene glycol monomethyl ether (PGME)) as a side component. Thus, residue defects are suppressed.

Here, examples of the monohydric alcohol used in the rinsing step include linear, branched, or cyclic monohydric alcohols, and specifically, 1-butanol, 2-butanol, 3-methyl-1-butanol, tert-butyl alcohol, 1-pentanol, 2-pentanol, 1-hexanol, 4-methyl-2-pentanol, 1-heptanol, 1-octanol, 2-hexanol, cyclopentanol, 2-heptanol, 2-octanol, 3-hexanol, 3-heptanol, 3-octanol, and 4-octanol. More preferred examples of the monohydric alcohol having 5 or more carbon atoms include 1-hexanol, 2-hexanol, 4-methyl-2-pentanol (methyl isobutyl carbinol: MIBC), 1-pentanol, and 3-methyl-1-butanol.

The respective components in plural numbers may be mixed, or the components may be mixed with an organic solvent other than the above solvents, and used.

The moisture content in the rinsing liquid is preferably 10% by mass or less, more preferably 5% by mass or less, and still more preferably 3% by mass or less. By setting the moisture content in the rinsing liquid to 10% by mass or less, good development characteristics can be obtained.

An appropriate amount of a surfactant may also be added to the rinsing liquid.

A method for the rinsing step is not particularly limited, but examples thereof include a method in which a rinsing liquid is continuously discharged on a substrate rotated at a constant rate (a rotation application method), a method in which a substrate is immersed in a tank filled with a rinsing liquid for a certain period of time (a dip method), and a method in which a rinsing liquid is sprayed on a substrate surface (a spray method). Among those, it is preferable that a washing treatment is carried out using the rotation application method, and a substrate is rotated at a rotation speed of 2,000 rpm to 4,000 rpm after washing, thereby removing the rinsing liquid from the substrate.

Furthermore, the pattern forming method of the present invention may include a heating step (post bake) after the rinsing step. The developer and the rinsing liquid remaining between and inside the patterns are removed by the baking. The heating step after the rinsing step is carried out at typically 40° C. to 160° C., and preferably 70° C. to 95° C., and typically for 10 seconds to 3 minutes, and preferably for 30 seconds to 90 seconds.

It is preferable that various materials (for example, a resist solvent, a developer, a rinsing liquid, a composition for forming an antireflection film, and a composition for forming a topcoat) used in the composition of the present invention and the pattern forming method of the present invention do not include impurities such as metals. The content of the impurities included in these materials is preferably 1 ppm by mass or less, more preferably 10 ppb by mass or less, still more preferably 100 ppt by mass or less, particularly preferably 10 ppt by mass or less, and most preferably 1 ppt by mass or less. Here, examples of the metal impurities include Na, K, Ca, Fe, Cu, Mg, Al, Li, Cr, Ni, Sn, Ag, As, Au, Ba, Cd, Co, Pb, Ti, V, W, and Zn.

Examples of a method for removing impurities such as metals from the various materials include filtration using a filter. As for the filter pore diameter, the pore size is preferably 10 nm or less, more preferably 5 nm or less, and still more preferably 3 nm or less. As for the materials of a filter, a polytetrafluoroethylene-made filter, a polyethylene-made filter, and a nylon-made filter are preferable. The filter may be formed of a composite material formed by combining this material with an ion exchange medium. As the filter, a filter which had been washed with an organic solvent in advance may be used. In the step of filtration using a filter, plural kinds of filters may be connected in series or in parallel, and used. In a case of using plural kinds of filters, a combination of filters having different pore diameters and/or materials may be used. In addition, various materials may be filtered plural times, and the step of filtering plural times may be a circulatory filtration step.

In the production of the actinic ray-sensitive or radiation-sensitive resin composition, it is preferable that after dissolving the respective components such as a resin and a photoacid generator in a resist solvent, circulatory filtration is performed using a plurality of filters with different materials. For example, it is preferable to connect a polyethylene-made filter with a pore size of 50 nm, a nylon-made filter with a pore size of 10 nm, and a polyethylene-made filter with a pore size of 3 nm in permuted connection, and then perform circulatory filtration ten times or more. A smaller pressure difference among the filters is preferable, and the pressure difference is generally 0.1 MPa or less, preferably 0.05 MPa or less, and more preferably 0.01 MPa or less. A smaller pressure difference between the filter and the charging nozzle also preferable, and the pressure difference is generally 0.5 MPa or less, preferably 0.2 MPa or less, and more preferably 0.1 MPa or less.

It is preferable to subject the inside of a device for producing the actinic ray-sensitive or radiation-sensitive resin composition to gas replacement with inert gas such as nitrogen, whereby it is possible to suppress an active gas such as oxygen from being dissolved in the composition.

After being filtered by a filter, the actinic ray-sensitive or radiation-sensitive resin composition is charged into a clean container. It is preferable that the actinic ray-sensitive or radiation-sensitive resin composition charged in the container is subjected to cold storage, whereby performance degradation over time can be suppressed. A shorter time from completion of the charge of the composition into the container to initiation of refrigeration storage is preferable, and the time is generally within 24 hours, preferably within 16 hours, more preferably within 12 hours, and still more preferably 10 hours. The storage temperature is preferably 0° C. to 15° C., more preferably 0° C. to 10° C., and still more preferably 0° C. to 5° C.

Moreover, examples of the method for reducing the impurities such as metals included in the various materials include a method involving selecting raw materials having a small content of metals as raw materials constituting various materials, a method involving subjecting raw materials constituting various materials to filtration using a filter, and a method involving performing distillation under the condition with contamination being suppressed to the largest degree by, for example, lining the inside of a device with TEFLON (registered trademark).

In addition to filtration using a filter, removal of impurities by an adsorbing material may be carried out, or a combination of filtration using a filter and an adsorbing material may be used. As the adsorbing material, known adsorbing materials may be used, and for example, inorganic adsorbing materials such as silica gel and zeolite, and organic adsorbing materials such as activated carbon can be used. It is necessary to prevent the incorporation of metal impurities in the production process in order to reduce the impurities such as metals included in the various materials. Sufficient removal of metal impurities from a production device can be checked by measuring the content of metal components included in a washing liquid used to wash the production device. The content of the metal components included in the washing liquid after the use is preferably 100 parts per trillion (ppt) or less, more preferably 10 ppt or less, and still more preferably 1 ppt or less.

An electrically conductive compound may be added to an organic treatment liquid such as a developer and a rinsing liquid in order to prevent failure of chemical liquid pipe and various parts (a filter, an O-ring, a tube, or the like) due to electrostatic charge, and subsequently generated electrostatic discharge. The electrically conductive compound is not particularly limited and examples thereof include methanol. The addition amount is not particularly limited, but from the viewpoint of maintaining preferred development characteristics or rinsing characteristics, it is preferably 10% by mass or less, and more preferably 5% by mass or less. For members of the chemical liquid pipe, various pipes coated with stainless steel (SUS), or a polyethylene, polypropylene, or fluorine resin (a polytetrafluoroethylene or perfluoroalkoxy resin, or the like) that has been subjected to an antistatic treatment can be used. In the same manner, for the filter or the O-ring, polyethylene, polypropylene, or fluorine resin (a polytetrafluoroethylene or perfluoroalkoxy resin, or the like) that has been subjected to an antistatic treatment can be used.

A method for improving the surface roughness of a pattern may be applied to the pattern formed by the method of the present invention. Examples of the method for improving the surface roughness of a pattern include the method of treating a resist pattern by a plasma of a hydrogen-containing gas disclosed in WO2014/002808A1. In addition, known methods as described in JP2004-235468A, US2010/0020297A, JP2009-19969A, JP2008-83384A, and Proc. of SPIE Vol. 832883280N-1 "EUV Resist Curing Technique for LWR Reduction and Etch Selectivity Enhancement" may be applied.

The pattern forming method of the present invention can be used for a guide pattern formation in a directed self-assembly (DSA) (see, for example, ACS Nano Vol. 4, No. 8, Pages 4815-4823).

In addition, a pattern formed by the method can be used as a core material (core) of the spacer process disclosed in JP1991-270227A (JP-H03-270227A) and JP2013-164509A.

In addition, the present invention further relates to a method for manufacturing an electronic device, including the above-described pattern forming method of the present invention, and an electronic device manufactured by the manufacturing method.

The electronic device of the present invention is suitably mounted on electric or electronic equipment (for example, home electronics, office automation (OA)-related equipment, media-related equipment, optical equipment, telecommunication equipment, and the like).

EXAMPLES

Examples will be described below, but the present invention is not limited thereto.

Hereinbelow, the compounds used in Examples will be firstly described in detail.

<Synthesis of Photoacid Generator (PAG)>

The structures of PAG1 to 13 and PAG-101 to 105 to be used are shown below. Further, a specific synthesis method for PAG-1 and PAG-2 is shown below. Other photoacid generators were also synthesized by the same method.

In addition, * in PAG-9 represents a binding position of the repeating unit.

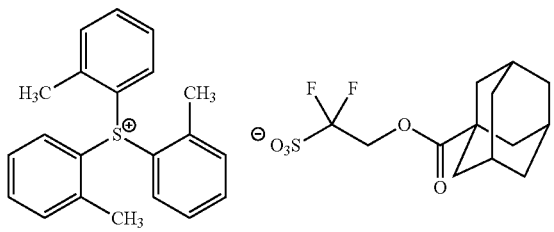

PAG-1

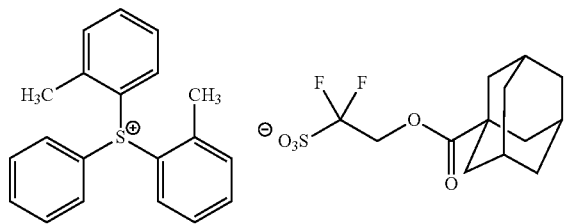

PAG-2

-continued
PAG-3
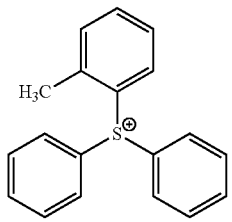 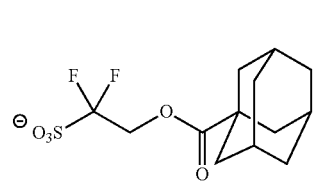
PAG-4
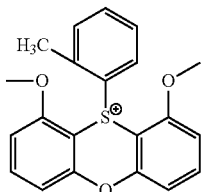 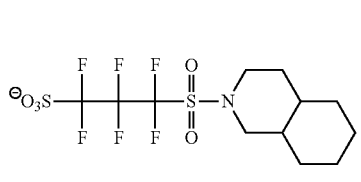
PAG-5
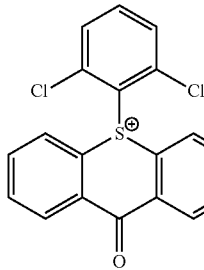 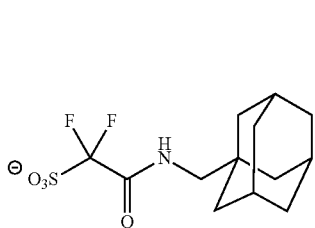
PAG-6
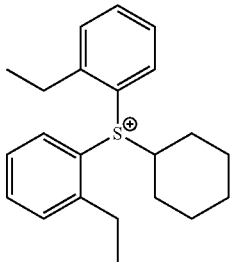 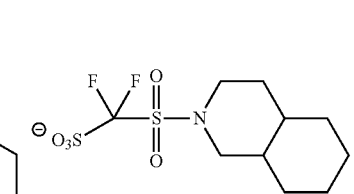
PAG-7
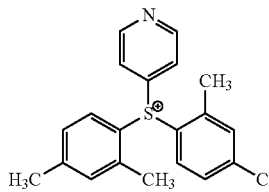 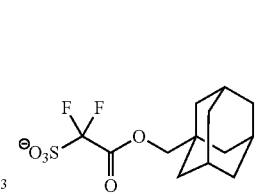
PAG-8
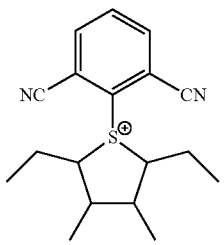 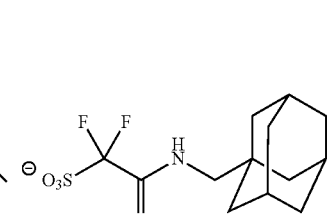
PAG-9
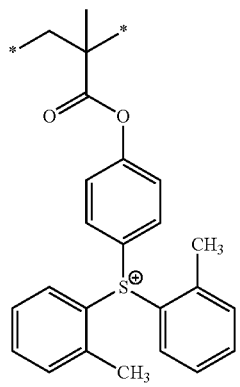 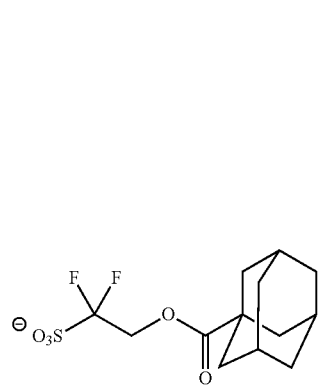
PAG-10
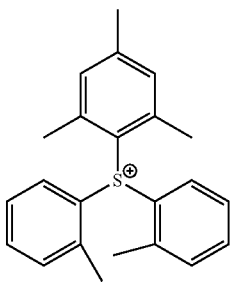 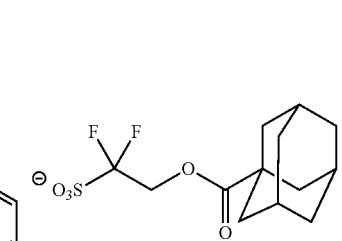
PAG-11
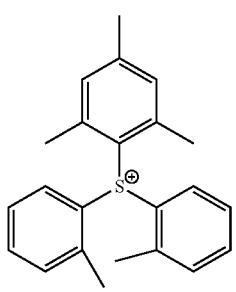 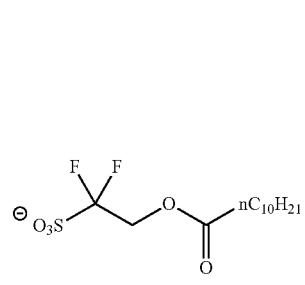

-continued

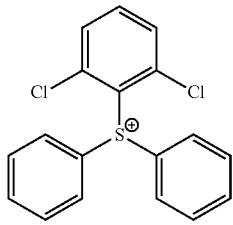
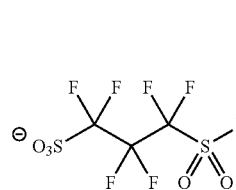
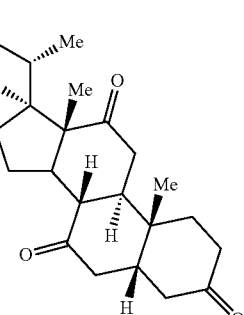

PAG-12

PAG-13     PAG-101

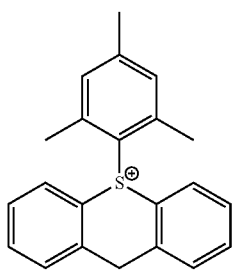
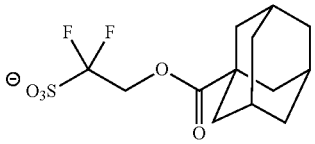
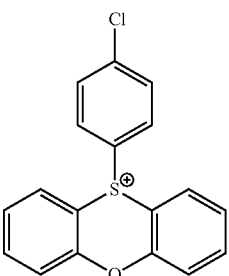
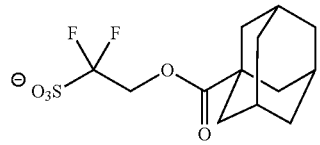

PAG-102     PAG-103

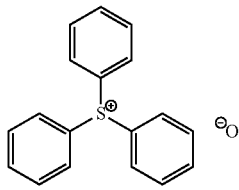
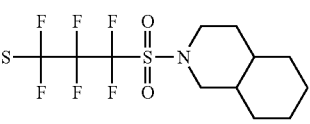
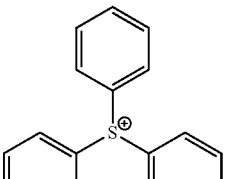
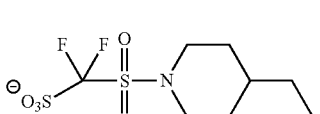

PAG-104     PAG-105

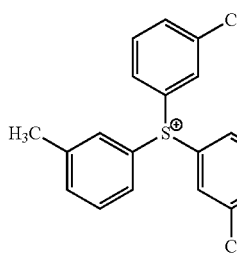
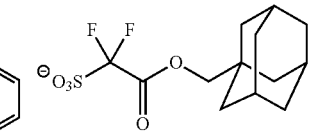
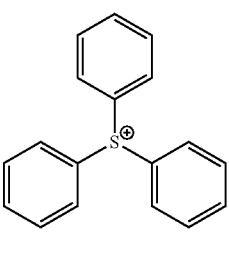
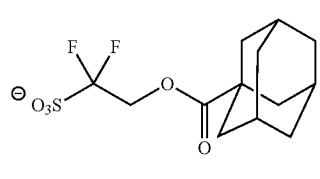

Synthesis Example: Synthesis of PAG-1

Under a nitrogen stream, thionyl chloride (2.4 g) was added dropwise to a mixed liquid (0° C.) of tetrahydrofiran (30 mL) and an orthotolylmagnesium bromide solution (1.0 mol/L) (100 mL) under stirring, and the obtained mixed liquid was stirred for 3 hours. Thereafter, this mixed liquid was set to 0° C. and chlorotrimethylsilane (5.4 g) was added dropwise to the mixed liquid. Then, the mixed liquid was stirred at room temperature for 2 hours, and the mixed liquid was further stirred at 60° C. for 6 hours. Thereafter, a 12% aqueous hydrogen bromide solution (45 mL) was added to the mixed liquid, and the mixed liquid was stirred at room temperature for 1 hour. Next, toluene (45 mL) was added to the mixed liquid, and the mixture was extracted twice with a 12% aqueous hydrogen bromide solution. The water phase of the obtained extract liquid was washed twice with toluene, and then extracted three times with chloroform. The solvent was removed by distillation from the obtained extract liquid using a rotary evaporator, and then the obtained oily mixture was purified by silica gel chromatography (ethyl acetate/ethanol=10/1) to obtain PAG-1A (a bromo salt of PAG-1) (1.2 g).

Dichloromethane (10 mL) and water (10 mL) were added to PAG-1A (1.0 g) obtained above and triethylammonium 2-(adamantane-1-carbonyloxy)-1,1-difluoro-ethanesulfonate (1.05 g), and the mixed liquid was stirred for 30 minutes. The mixed liquid was extracted with dichloromethane (20 mL), and the organic phase was collectively washed twice with 10%-by-weight aqueous potassium carbonate (20 mL) and washed five times with water (20 mL). The solvent was removed by distillation from the obtained solution, and the obtained solid content was recrystallized from isopropyl alcohol to obtain PAG-1 (1.4 g).

Synthesis Example: Synthesis of PAG-2

Under a nitrogen stream, while a mixed liquid of tetrahydrofuran (43 mL) and di-orthotolylsulfoxide (2.0 g) was stirred, a phenylmagnesium bromide solution (1.0 mol/L) (10.4 mL) was added dropwise thereto, and the obtained mixed liquid (0° C.) was stirred for 15 minutes. Thereafter, the mixed liquid was set to 0° C., and chlorotrimethylsilane (1.8 g) was added dropwise to the mixed liquid. Thereafter, the mixed liquid was stirred at room temperature for 2 hours, and the mixed liquid was further stirred at 60° C. for 4 hours. Then, a 12% aqueous hydrogen bromide solution (40 mL) was added to the mixed liquid, and the mixed liquid was stirred at room temperature for 1 hour. Thereafter, toluene (40 mL) was added to the mixed liquid, followed by performing extraction twice with a 12% aqueous hydrogen bromide solution. The water phase of the obtained extract was washed twice with toluene and then extracted four times with chloroform. The solvent was removed by distillation from the obtained extract liquid using a rotary evaporator, and then the obtained oily mixture was purified by silica gel chromatography (ethyl acetate/ethanol=10/1) to obtain PAG-2A (a bromo salt of PAG-2) (1.5 g).

Dichloromethane (10 mL) and water (10 mL) were added to PAG-2A (1.0 g) obtained above and triethylammonium 2-(adamantane-1-carbonyloxy)-1,1-difluoro-ethanesulfonate (1.15 g), and the mixed liquid was stirred for 30 minutes. The mixed liquid was extracted with dichloromethane (20 mL), and the organic phase was collectively washed twice with 10%-by-weight aqueous potassium carbonate (20 mL) and washed five times with water (20 mL). The solvent was removed by distillation from the obtained solution, and the obtained solid content was recrystallized from ethyl acetate/hexane (1/4) to obtain PAG-2 (1.4 g).

Synthesis of Resin

The structures of Polymers (1) to (9) to be used are shown below. Further, a specific synthesis method for Polymer (1) is shown below. Other polymers were also synthesized by the same method.

In addition, the synthesized polymer structures, and the compositional ratios (the molar ratios; corresponding in order from the left side), the weight-average molecular weight (Mw), and the dispersity (Mw/Mn) of the respective repeating units are shown below.

Synthesis Example: Synthesis of Polymer (1)

Under a nitrogen gas stream, cyclohexanone (102.3 parts by mass) was heated to 80° C. While stirring the liquid, a mixed solution of a monomer represented by Structural Formula M-1 (22.2 parts by mass), a monomer represented by Structural Formula M-2 (22.8 parts by mass), a monomer represented by Structural Formula M-3 (6.6 parts by mass), cyclohexanone (189.9 parts by mass), and dimethyl 2,2'-azobisiso butyrate [V-601, manufactured by Wako Pure Chemical Industries, Ltd.] (2.40 parts by mass) were added dropwise thereto for 5 hours. After completion of the dropwise addition, the reaction solution was further stirred at 80° C. for 2 hours. Thereafter, the reaction solution was left to be cooled and then subjected to a reprecipitation treatment with a large amount of hexane/ethyl acetate (mass ratio of 9:1). The solid content precipitated by the reprecipitation treatment was recovered by filtration, and the obtained solid fraction was dried in vacuo to obtain Polymer (1) (41.1 parts by mass).

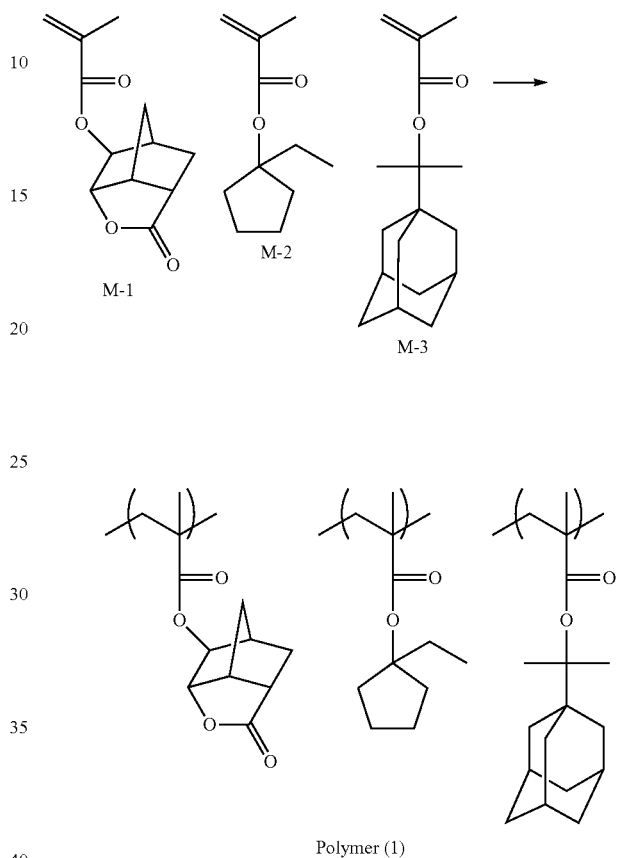

Polymer (1)

The weight-average molecular weight (Mw: in terms of polystyrene) as calculated from the GPC (carrier: tetrahydrofuran (THF)) and the dispersity of the obtained Polymer (1) were Mw=9,500 and Mw/Mn=1.60, respectively. The compositional ratio (% by mole) as measured by $^{13}$C-NMR was M-1/M-2/M-3=40/50/10.

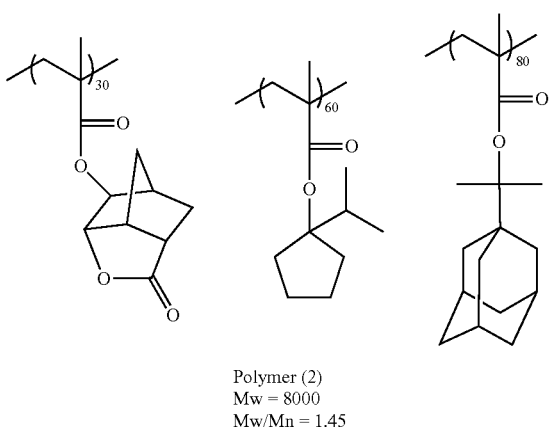

Polymer (2)
Mw = 8000
Mw/Mn = 1.45

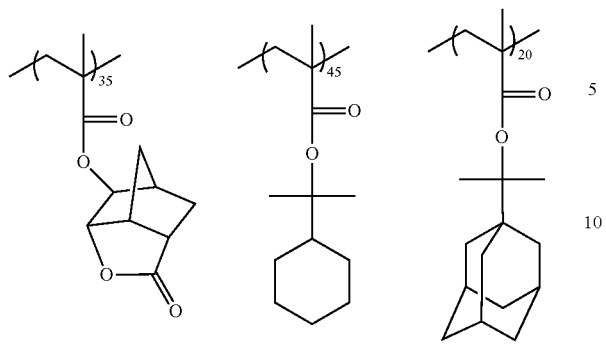

Polymer (3)
Mw = 16300
Mw/Mn = 1.65

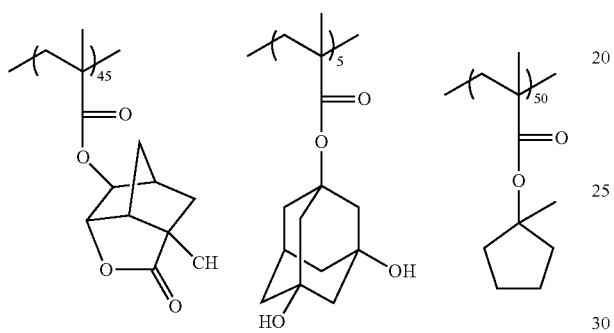

Polymer (4)
Mw = 1160
Mw/Mn = 1.63

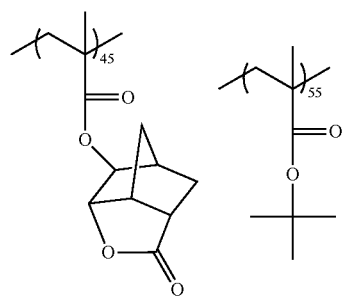

Polymer (5)
Mw = 1800
Mw/Mn = 1.70

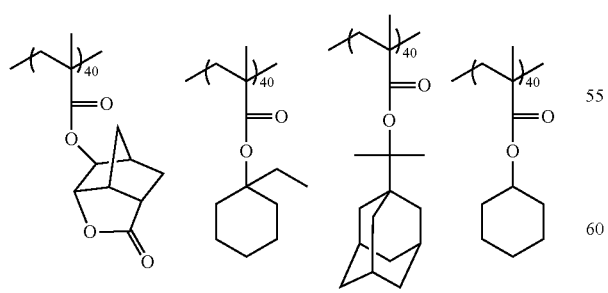

Polymer (6)
Mw = 13500
Mw/Mn = 1.65

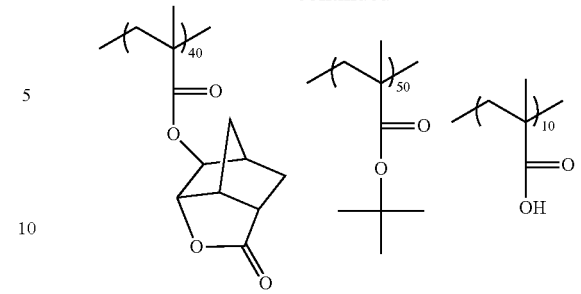

Polymer (7)
Mw = 15500
Mw/Mn = 1.75

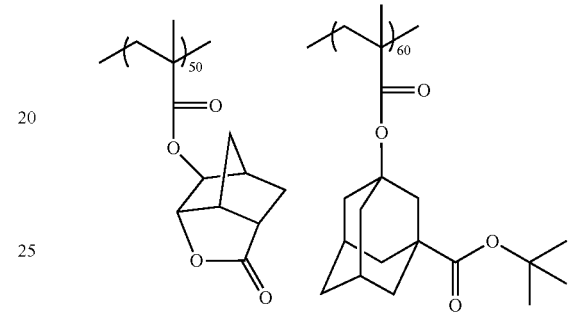

Polymer (8)
Mw = 21000
Mw/Mn = 1.75

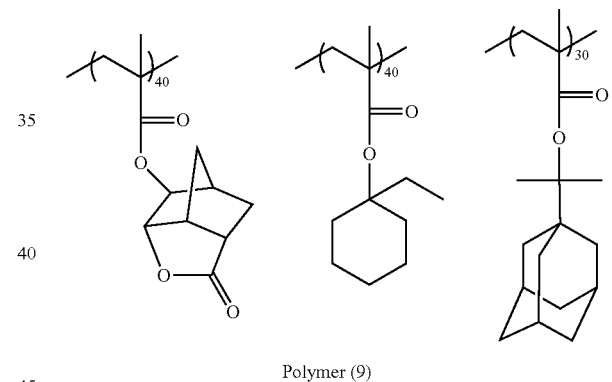

Polymer (9)
Mw = 15000
Mw/Mn = 1.60

<Acid Diffusion Control Agent>
DIA: 2,6-Diisopropylaniline
TEA: Triethanolamine
DBA: N,N-Dibutylaniline
PBI: 2-Phenylbenzimidazole
PEA: N-Phenyldiethanolamine Furthermore, the following compounds (N-1) to (N-5) were also used as the acid diffusion control agent.

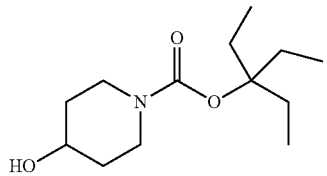

(N-1)

-continued

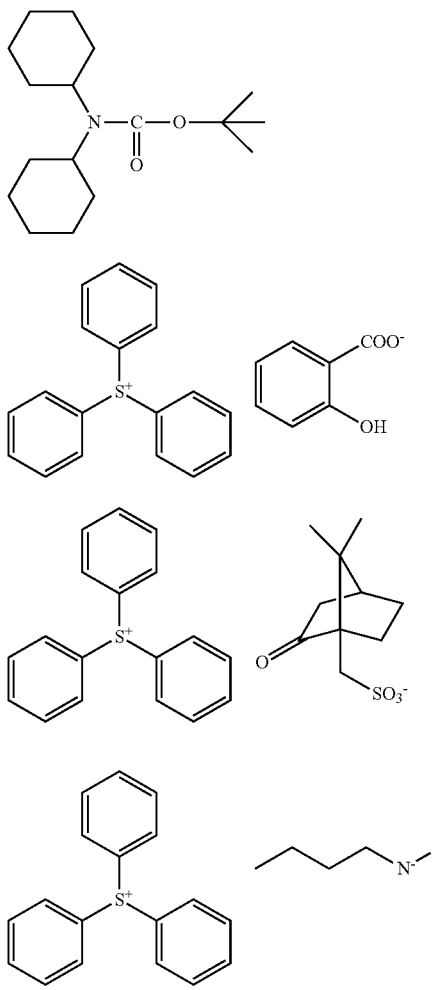

<Hydrophobic Resin (D)>

As the hydrophobic resin (D), any resin can be appropriately selected from the resins (HR-1) to (HR-65), and (C-1) to (C-28) exemplified above, and used.

<Surfactant>

W-1: MEGAFACE F176 (manufactured by DIC Corporation) (fluorine-based)

W-2: MEGAFACE R08 (manufactured by DIC Corporation) (fluorine- and silicon-based)

W-3: PF6320 (manufactured by OMNOVA Solutions Inc.) (fluorine-based)

W-4: TROYSOL S-366 (manufactured by Troy Chemical Corporation)

<Solvent>

A1: Propylene glycol monomethyl ether acetate (PGMEA)

A2: Cyclohexanone

A3: γ-Butyrolactone

B1: Propylene glycol monomethyl ether (PGME)

B2: Ethyl lactate

<Developer>

SG-1: Butyl acetate

SG-2: Methyl amyl ketone

SG-3: Ethyl-3-ethoxypropionate

SG-4: Pentyl acetate

SG-5: Isopentyl acetate

SG-6: Propylene glycol monomethyl ether acetate (PGMEA)

SG-7: Cyclohexanone

<Rinsing Liquid>

SR-1: 4-Methyl-2-pentanol

SR-2: 1-Hexanol

SR-3: Butyl acetate

SR-4: Methyl amyl ketone

SR-5: Ethyl-3-ethoxypropionate

Examples 1 to 15 and Comparative Examples 1 to 6

An actinic ray-sensitive or radiation-sensitive resin composition (resist composition) was prepared by dissolving 3.5% by mass in terms of solid contents of components shown in Table 3 in a solvent shown in the same table, and filtering each of the components using a polyethylene filter with a pore size of 0.03 μm.

A composition for forming an organic antireflection film, ARC29SR (manufactured by Nissan Chemical Industries, Ltd.), was applied onto a silicon wafer, and the silicon wafer having the composition for forming an organic antireflection film applied thereon was baked at 205° C. for 60 seconds to form an antireflection film with a film thickness of 100 nm. A resist composition was applied onto the antireflection film and the resist composition applied on the antireflection film was baked (PB: Prebake) at 100° C. for 60 seconds to form a resist film with a film thickness of 80 nm.

Next, the resist film on the silicon wafer was subjected to pattern exposure using an ArF excimer laser liquid immersion scanner (manufactured by ASML; XTI700i, NA1.20, C-Quad, outer sigma 0.981, inner sigma 0.895, and XY inclination) via an exposure mask (line/space=binary mask 44 nm/44 nm). Ultrapure water was used as the liquid immersion liquid. Thereafter, the pattern-exposed resist film was heated (PEB: Post Exposure Bake) at 85° C. for 60 seconds.

Subsequently, the pattern-exposed resist film was developed by paddling a developer shown in Table 3 for 30 seconds. Next, paddling was performed with a rinsing liquid shown in Table 3 for 30 seconds while shaking off the developer, and the developed resist film was rinsed. Subsequently, the obtained silicon wafer was rotated at a rotation speed of 4,000 rpm for 30 seconds, and then baked at 90° C. for 60 seconds. In this manner, a resist pattern of a 1:1 line and space pattern with a line width of 44 nm was obtained.

TABLE 3

| | Photoacid generator (A) (2.1 g) | Resin (B) (10 g) | Acid diffusion inhibitor (C) (g) | Hydrophobic resin (D) (35 mg) | Solvent (mass ratio) | Surfactant (10 mg) | Developer (mass ratio) | Rinsing liquid (mass ratio) |
|---|---|---|---|---|---|---|---|---|
| Example 1 | PAG-1 | Polymer (1) | DIA (0.29) | C-2 | A1/B1 (80/20) | W-1 | SG-1 | SR-1 |

TABLE 3-continued

| | Photoacid generator (A) (2.1 g) | Resin (B) (10 g) | Acid diffusion inhibitor (C) (g) | Hydrophobic resin (D) (35 mg) | Solvent (mass ratio) | Surfactant (10 mg) | Developer (mass ratio) | Rinsing liquid (mass ratio) |
|---|---|---|---|---|---|---|---|---|
| Example 2 | PAG-1 | Polymer (2) | TEA (0.31) | C-3 | A1/B1 (60/40) | W-3 | SG-1/SG-4 (50/50) | SR-1/SR-4 (90/10) |
| Example 3 | PAG-1 | Polymer (2) + Polymer (3) (5 g/5 g) | PBI (0.31) | HR-12 | B2 | W-4 | SG-1/SG-7 (95/5) | SR-1 |
| Example 4 | PAG-2 | Polymer (1) | DBA (0.41) | C-8 | A1 | W-4 | SG-2 | SR-1/SR-3 (90/10) |
| Example 5 | PAG-3 | Polymer (3) | N-1 (0.3) | C-4 | A1/B1 (90/10) | W-2 | SG-1/SG-5 (90/10) | SR-1/SR-2 (90/10) |
| Example 6 | PAG-4 | Polymer (6) | PEA (0.4) | HR-18 | A2 | W-1 | SG-1/SG-3 (90/10) | SR-1 |
| Example 7 | PAG-5 | Polymer (7) | N-1/PBI (0.15/0.1) | HR-56 | A1/A2 (50/50) | W-2 | SG-1/SG-6 (95/5) | SR-5 |
| Example 8 | PAG-6 | Polymer (5) | N-4 (0.32) | C-5 | A1/A2/B2 (40/40/20) | W-1 | SG-1 | SR-1 |
| Example 9 | PAG-7 | Polymer (4) | N-5 (0.29) | HR-32 | A1/A2 (60/40) | W-1 | SG-1 | SR-1 |
| Example 10 | PAG-8 | Polymer (9) | N-2 (0.31) | HR-19 | A1/A3 (70/30) | W-1 | SG-1 | SR-1 |
| Example 11 | PAG-9 | Polymer (8) | N-3 (0.41) | C-1 | A1/A2 (60/40) | W-1 | SG-1 | SR-1 |
| Example 12 | PAG-10 | Polymer (1) | N-3 (0.41) | C-1 | A1/A2 (60/40) | W-1 | SG-1 | SR-1 |
| Example 13 | PAG-11 | Polymer (1) | N-3 (0.41) | C-1 | A1/A2 (60/40) | W-1 | SG-1 | SR-1 |
| Example 14 | PAG-12 | Polymer (8) | N-3 (0.41) | C-1 | A1/A2 (60/40) | W-1 | SG-1 | SR-1 |
| Example 15 | PAG-13/PAG-105 (1.5 g/0.6 g) | Polymer (8) | N-3 (0.41) | C-1 | A1/A2 (60/40) | W-1 | SG-1 | SR-1 |
| Comparative Example 1 | PAG-101 | Polymer (1) | DIA (0.29) | C-2 | A1/A2 (60/40) | W-1 | SG-1 | SR-1 |
| Comparative Example 2 | PAG-102 | Polymer (2) | TEA (0.31) | C-3 | A1/A2 (60/40) | W-1 | SG-1/SG-4 (50/50) | SR-1 |
| Comparative Example 3 | PAG-103 | Polymer (5) | PBI (0.31) | HR-12 | A1/A3 (70/30) | W-1 | SG-1/SG-7 (95/5) | SR-1 |
| Comparative Example 4 | PAG-104 | Polymer (2) + Polymer (3) (5 g/5 g) | DBA (0.41) | C-4 | A1/A2 (70/30) | W-1 | SG-1 | SR-1 |
| Comparative Example 5 | PAG-104 | Polymer (6) | DBA (0.41) | C-4 | A1/A2 (70/30) | W-1 | SG-1 | SR-1 |
| Comparative Example 6 | PAG-104 | Polymer (1) | DBA (0.41) | C-4 | A1/A2 (60/40) | W-1 | SG-1 | SR-1 |

<Storage Stability (Sensitivity)>

In the obtained resist film, an exposure dose (mJ/cm$^2$) at a time when the resist pattern of the 1:1 line and space pattern with a line width of 44 nm was formed was set as an optimal exposure dose. The smaller the value is, the higher the sensitivity is, which is thus preferable. Changes in sensitivity were evaluated using the ratio (S1/S2) of an optimal exposure dose S1 obtained in a case of using the resist composition immediately after preparation and a suitable exposure dose S2 obtained in a case using the resist composition left to stand at 4° C. for 1 week after preparation. In a case where the value of S1/S2 is closer to 1, the change in sensitivity is smaller, which is thus preferable.

<Storage Stability (Particles)>

The number of particles (a particle initial value) in the resist composition immediately after preparation and the number of particles (the number of particles after the passing of time) in the resist composition after being left to stand at 4° C. for 3 months were counted using a particle counter manufactured by Rion Co., Ltd., and the number of increased particles calculated by (the number of particles after passing of time)−(particle initial value) was calculated. Incidentally, here, particles with a particle diameter of 0.25 μm or more included in 1 mL of the resist composition were counted. A case where the number of increased particles is equal to 0.2/ml or less is taken as "A", a case of more than 0.2/ml and 1/ml or less is taken as "B", a case of more than 1/ml and 5/ml or less is taken as "C", and a case of more than 5/ml is taken as "D".

<Pattern Shape>

A cross-sectional shape of the line pattern of a 1:1 line and space pattern with a line width of 44 nm, which was obtained by the minimum exposure dose for reproducing the mask pattern of a 1:1 line and space pattern with a line width of 44 nm, was observed using a scanning electron microscope. The pattern shape was evaluated using a ratio (a/b) of a length a (nm) of the upper side of the pattern and a length b (nm) of the lower side of the pattern. A case where (a/b) is 1.0 or more and less than 1.1 is taken as "A", a case of 1.1 or more and less than 1.3 is taken as "B", and a case of 1.3 or more is taken as "C". In a case where the ratio (a/b) is closer to 1, the pattern shape is closer to a rectangle, which is thus preferable.

<Line Width Roughness (LWR)>

An exposure dose for reproducing the mask pattern of a 1:1 line and space pattern with a line width of 44 nm was taken as an optimal exposure dose, and in the measurement of the line and space resist pattern of the 1:1 line and space pattern with a line width of 44 nm, observation of the line width was carried out at arbitrary points, as observed from the upper part of the pattern using a length measurement scanning electron microscope (SEM (S-8840, Hitachi, Ltd.)), and the measurement variations thereof were evaluated at 3σ. A smaller value shown in the section of "LWR (nm)" in Table 4 indicates better performance.

<Pattern Collapse>

An exposure dose for reproducing the mask pattern of a 1:1 line and space pattern with a line width of 44 nm was taken as an optimal exposure dose, and in a further reduction in the exposure dose from the optimal exposure dose, the pattern collapse was evaluated using a space width with which resolution was observed without the collapse of the pattern. A higher value of the space width shown in the section of "Pattern collapse (nm)" shown in Table 4 indicates that a finer pattern is resolved without collapse, and indicates that it is difficult for pattern collapse to occur.

The evaluation results are shown in Table 4.

TABLE 4

|  | Evaluation item 1 Sensitivity ratio | Evaluation item 2 Particle | Evaluation item 3 Pattern shape | Evaluation item 4 LWR (nm) | Evaluation item 5 Pattern collapse (nm) |
|---|---|---|---|---|---|
| Example 1 | 0.92 | A | A | 3.35 | 57.6 |
| Example 2 | 0.9 | A | A | 3.31 | 57.4 |
| Example 3 | 0.94 | A | A | 3.39 | 57.1 |
| Example 4 | 0.88 | A | A | 3.58 | 54.1 |
| Example 5 | 0.87 | A | A | 3.82 | 51 |
| Example 6 | 0.91 | A | A | 3.55 | 54.2 |
| Example 7 | 0.89 | A | A | 3.24 | 58.8 |
| Example 8 | 0.92 | A | A | 3.71 | 52.3 |
| Example 9 | 0.93 | A | A | 3.57 | 54.7 |
| Example 10 | 0.91 | A | A | 3.96 | 50.1 |
| Example 11 | 0.9 | A | A | 3.52 | 54.2 |
| Example 12 | 0.92 | A | A | 3.17 | 59 |
| Example 13 | 0.91 | A | A | 3.97 | 50.3 |
| Example 14 | 0.93 | A | A | 3.4 | 55.8 |
| Example 15 | 0.91 | A | A | 3.23 | 58.6 |
| Comparative Example 1 | 0.77 | B | C | 4.75 | 39.7 |
| Comparative Example 2 | 0.78 | C | B | 4.8 | 43.2 |
| Comparative Example 3 | 0.74 | B | C | 5.11 | 40.8 |
| Comparative Example 4 | 0.68 | B | B | 4.79 | 38.4 |
| Comparative Example 5 | 0.74 | C | C | 4.98 | 34.9 |
| Comparative Example 6 | 0.74 | B | B | 5.04 | 37.7 |

From the results in the above table, it was found that the resist composition of the present invention has a small LWR and a further suppression of pattern collapse, as compared in Comparative Examples 1 to 6 in which a predetermined photoacid generator was not used. Further, it was further found that the resist composition of the present invention satisfies excellent storage stability (in particular, sensitivity and generation of particles) and a good shape simultaneously.

Among those, from the comparison of Examples 3 to 5, in a case of using the photoacid generator represented by General Formula (1-A) and the photoacid generator represented by General Formula (1-B), excellent effects were obtained, and in a case of using the photoacid generator represented by General Formula (1-B), superior effects were obtained.

Furthermore, from the comparison between Example 10 and other Examples, superior effects were obtained in a case where in General Formula (1), $X_1$ and $X_2$ each independently represent an aromatic group or an alicyclic group.

Incidentally, from the comparison between Example 12 and Example 13, superior effects were obtained in a case where the anion represented by General Formula (2) was used as an anion of the photoacid generator.

In addition, from the comparison between Example 9 and Example 15, superior effects were obtained in a case where the low molecular photoacid generator represented by General Formula (1) was used as the photoacid generator.

<Calculation of Relative Absorbance ($\varepsilon_r$)>

Firstly, a molar absorbance coefficient (E) was calculated for each of a photoacid generator to be targeted and triphenylsulfonium nonaflate. The UV spectrum of a measurement solution in which a compound to be measured was dissolved in acetonitrile, by using a cell with 1 cm² square was measured, and the relative absorbance (ε) was calculated according to a Lambert-Beer equation from an absorbance (A) for light at a wavelength of 193 nm and a measurement solvent density (C). The relative absorbance $\varepsilon_r$ of the photoacid generator to be targeted is a value which is normalized, taking the absorbance coefficient of triphenylsulfonium nonaflate as 1.

$$\varepsilon_r = \varepsilon_z / \varepsilon_{TPS}$$

$\varepsilon_r$: Relative absorbance of a photoacid generator to be targeted $\varepsilon_z$: Molar absorbance coefficient of a photoacid generator to be targeted $\varepsilon_{TPS}$: Molar absorbance coefficient of triphenylsulfonium nonaflate <Calculation of Relative Quantum Efficiency ($\varphi_r$)>

The relative quantum efficiency ($\varphi_r$) is defined as $\varphi_r = (\varphi_{TPS} \times \varepsilon_{TPS} \times E_{TPS})/(\varepsilon_r \times E_r)$ in a case where the relative absorbance of the photoacid generator to be targeted is taken as $\varepsilon_r$, the relative quantum efficiency is taken as $\varepsilon_r$, the sensitivity is taken as $E_r$, the molar absorbance coefficient of triphenylsulfonium nonaflate is taken as $\varepsilon_{TPS}$, the relative quantum efficiency is taken as $\varphi_{TPS}$, and the sensitivity is taken as $E_{TPS}$. Here, $\varepsilon_{TPS}$ and $\varphi_{TPS}$ are 1, and $E_{TPS}$ and $E_r$ are obtained by the measuring method described above. In the measurement of $E_r$, the types and amounts of the resins, the basic compounds, and the solvents were set to the same measuring conditions as for $E_{TPS}$. The amount of the photoacid generator was set to be the same as the measuring conditions for $E_{TPS}$ with the amount of the substance (molar quantity) as a reference. The relative quantum efficiency $\varphi_r$ of the photoacid generator to be targeted was calculated by substituting the measured values of $\varepsilon_r$, $E_r$, and $E_{TPS}$ in the formula described below.

The relative absorbance ($\varepsilon_r$) and the relative quantum efficiency $\varphi_r$ of PAG-1 were measured to be 0.7 and 1.2, respectively.

<Calculation of Sensitivity $E_r$ and $E_{TPS}$>

A resist solution with a concentration of the solid content of 3.5% by mass was obtained by dissolving 10 g of Resin Polymer (1) used in Example 1, 0.3 g of a basic compound DIA, and 2.0 g of triphenylsulfonium nonaflate in a solvent (PGMEA). A resist composition was prepared by filtering the resultant using a polyethylene filter with a pore size of 0.03 μm.

A composition for forming an organic antireflection film, ARC29SR (manufactured by Nissan Chemical Industries, Ltd.), was applied onto a silicon wafer, and baking was performed at 205° C. for 60 seconds to form an antireflection film with a film thickness of 100 nm. A resist composition was applied on the antireflection film, and baking (PB: Prebake) was performed at 100° C. for 60 seconds to form a resist film with a film thickness of 100 nm.

The entire surface of the resist film on the obtained wafer was exposed using an ArF excimer laser scanner (manufactured by ASML; PAS5500/1100). Thereafter, the exposed resist film was heated (PEB: Post Exposure Bake) at 100° C. for 60 seconds. Subsequently, development was performed by paddling using an organic-based developer (butyl acetate) for 30 seconds and rinsing was carried out by paddling using a rinsing liquid (methyl isobutyl carbinol (MIBC)) for 30 seconds while shaking off the developer. Subsequently, after rotating the wafer at a rotation speed of 4,000 rpm for 30 seconds, baking was performed at 90° C. for 60 seconds. Thereafter, the film thickness after baking was measured.

By increasing the exposure dose from 1 mJ/cm² by 0.3 mJ/cm² increments, the exposure dose when the film thickness after baking exceeded 10 nm was defined as the sensitivity $E_{TPS}$ of triphenylsulfonium nonaflate.

The photoacid generator was changed from triphenylsulfonium nonaflate to an acid generator to be targeted and the sensitivity $E_r$ of the photoacid generator to be targeted was measured with the same steps.

What is claimed is:

1. An actinic ray-sensitive or radiation-sensitive resin composition comprising a photoacid generator represented by General Formula (1-A),

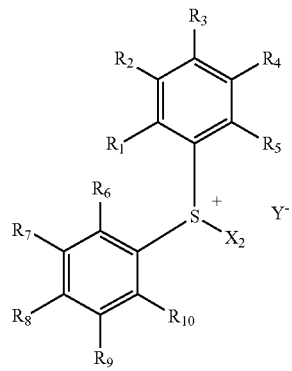

in General Formula (1-A), $R_1$ and $R_6$ each independently represent an alkyl group, an alkylthio group, a halogen atom, or a cyano group;

$R_2$ to $R_5$ and $R_7$ to $R_{10}$ each independently represent a hydrogen atom, an alkyl group, a cycloalkyl group, an aryl group, an acyl group, an alkyloxycarbonyl group, a cycloalkyloxycarbonyl group, an alkylthio group, an aryloxy group, an arylthio group, an aryloxycarbonyl group, an alkylaminocarbonyl group, a cycloalkylaminocarbonyl group, an arylaminocarbonyl group, a cyano group, a halogen atom, an amino group, a nitro group, a carboxyl group, or a hydroxyl group;

$X_2$ represents an aromatic group or an alicyclic group, $R_5$ and $X_2$ may be bonded to each other directly or via a linking group to form a ring, and $Y^-$ represents an anion represented by General Formula (2),

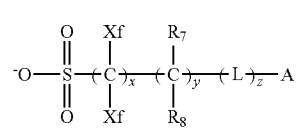

in General Formula (2), Xf's each independently represent a fluorine atom or an alkyl group substituted with at least one fluorine atom;

$R_7$ and $R_8$ each independently represent a hydrogen atom, a fluorine atom, an alkyl group, or an alkyl group substituted with at least one fluorine atom;

L represents a divalent linking group;

A represents a cyclic organic group;

x represents an integer of 1 to 20, y represents an integer of 0 to 10, z represents an integer of 0 to 10, in a case where y is 2 or more, a plurality of $R_7$'s and $R_8$'s may be the same as or different from each other, respectively, and in a case where z is 2 or more, a plurality of L's may be the same as or different from each other.

2. The actinic ray-sensitive or radiation-sensitive resin composition according to claim 1, wherein the photoacid generator represented by General Formula (1-A) is a photoacid generator represented by General Formula (1-B),

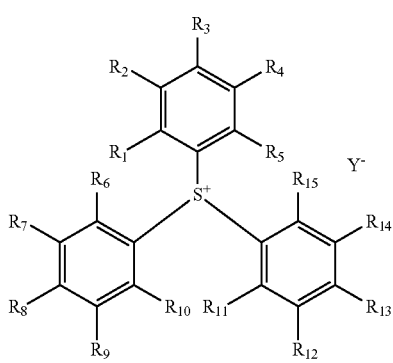

(1-B)

in General Formula (1-B), $R_1$, $R_6$, and $R_{11}$ each independently represent an alkyl group, an alkylthio group, a halogen atom, or a cyano group;

$R_2$ to $R_5$, $R_7$ to $R_{10}$, and $R_{12}$ to $R_{15}$ each independently represent a hydrogen atom, an alkyl group, a cycloalkyl group, an aryl group, an acyl group, an alkyloxycarbonyl group, a cycloalkyloxycarbonyl group, an alkylthio group, an aryloxy group, an arylthio group, an aryloxycarbonyl group, an alkylaminocarbonyl group, a cycloalkylaminocarbonyl group, an arylaminocarbonyl group, a cyano group, a halogen atom, an amino group, a nitro group, a carboxyl group, or a hydroxyl group, $R_5$ and $R_{15}$ may be bonded to each other directly or via a linking group to form a ring, and $Y^-$ represents the anion represented by General Formula (2).

3. The actinic ray-sensitive or radiation-sensitive resin composition according to claim 2,
wherein $R_1$ represents an alkylthio group, a halogen atom, or a cyano group.

4. The actinic ray-sensitive or radiation-sensitive resin composition according to claim 2, further comprising a resin including a repeating unit having a group that decomposes by the action of an acid to generate an alkali-soluble group.

5. The actinic ray-sensitive or radiation-sensitive resin composition according to claim 1,
wherein $R_1$ represents an alkylthio group, a halogen atom, or a cyano group.

6. The actinic ray-sensitive or radiation-sensitive resin composition according to claim 5, further comprising a resin including a repeating unit having a group that decomposes by the action of an acid to generate an alkali-soluble group.

7. The actinic ray-sensitive or radiation-sensitive resin composition according to claim 1, further comprising a resin including a repeating unit having a group that decomposes by the action of an acid to generate an alkali-soluble group.

8. The actinic ray-sensitive or radiation-sensitive resin composition according to claim 1, further comprising an acid diffusion control agent.

9. A resist film formed using the actinic ray-sensitive or radiation-sensitive resin composition according to claim 1.

10. A pattern forming method comprising:
a step of exposing the resist film according to claim 9; and
a step of developing the exposed resist film.

11. The pattern forming method according to claim 10, wherein the exposure is liquid immersion exposure.

12. A method for manufacturing an electronic device, comprising the pattern forming method according to claim 10.

13. An actinic ray-sensitive or radiation-sensitive resin composition comprising a photoacid generator represented by General Formula (1-B),

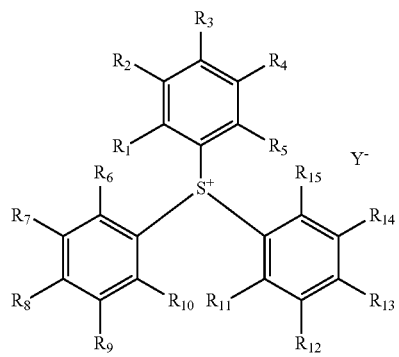

(1-B)

in General Formula (1-B), $R_1$, $R_6$, and $R_{11}$ each independently represent an alkyl group, an alkylthio group, or a cyano group;

$R_2$ to $R_5$, $R_7$ to $R_{10}$, and $R_{12}$ to $R_{15}$ each independently represent a hydrogen atom, an alkyl group, a cycloalkyl group, an aryl group, an acyl group, an alkyloxycarbonyl group, a cycloalkyloxycarbonyl group, an alkylthio group, an aryloxy group, an arylthio group, an aryloxycarbonyl group, an alkylaminocarbonyl group, a cycloalkylaminocarbonyl group, an arylaminocarbonyl group, a cyano group, a halogen atom, an amino group, a nitro group, a carboxyl group, or a hydroxyl group, $R_5$ and $R_{15}$ may be bonded to each other directly or via a linking group to form a ring, and $Y^-$ represents a non-nucleophilic anion.

14. The actinic ray-sensitive or radiation-sensitive resin composition according to claim 13, further comprising a resin including a repeating unit having a group that decomposes by the action of an acid to generate an alkali-soluble group.

15. A resist film formed using the actinic ray-sensitive or radiation-sensitive resin composition according to claim 13.

16. A pattern forming method comprising:
a step of exposing the resist film according to claim 15; and
a step of developing the exposed resist film.

17. An actinic ray-sensitive or radiation-sensitive resin composition comprising a resin having a repeating unit represented by General Formula (1-C),

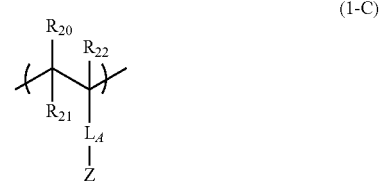

(1-C)

in General Formula (1-C), $R_{20}$ to $R_{22}$ each independently represents a hydrogen atom or a monovalent organic group, $L_A$ represents a single bond or a divalent linking group, and Z represents a group represented by General Formula (1-D),

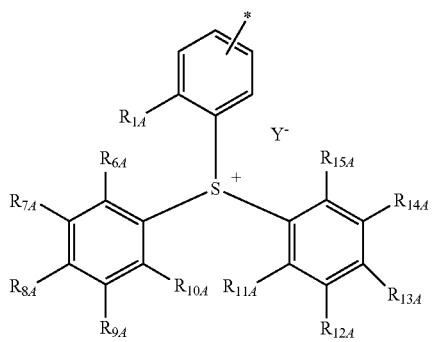

(1-D)

in General Formula (1-D), $R_{1A}$, $R_{6A}$, and $R_{11A}$ each independently represents a hydrogen atom, an alkyl group, an alkoxy group, an alkylthio group, a halogen atom, or a cyano group, at least one of $R_{1A}$, $R_{6A}$, and $R_{11A}$ represents a group other than a hydrogen atom, * represents a bonding position to $L_a$, and $R_{7A}$ to $R_{10A}$ and $R_{12A}$ to $R_{15A}$ each independently represents a hydrogen atom or a monovalent organic group, and $Y^-$ represents a non-nucleophilic anion.

18. The actinic ray-sensitive or radiation-sensitive resin composition according to claim 17, further comprising a resin including a repeating unit having a group that decomposes by the action of an acid to generate an alkali-soluble group.

19. A resist film formed using the actinic ray-sensitive or radiation-sensitive resin composition according to claim 17.

20. A pattern forming method comprising:
a step of exposing the resist film according to claim 19; and
a step of developing the exposed resist film.

* * * * *